US011459382B2

(12) United States Patent
Adiv et al.

(10) Patent No.: US 11,459,382 B2
(45) Date of Patent: Oct. 4, 2022

(54) DOSAGE AND ADMINISTRATION OF ANTI-C5 ANTIBODIES FOR TREATMENT OF PROTEIN-LOSING ENTEROPATHY IN PATIENTS

(71) Applicant: Alexion Pharmaceuticals, Inc., Boston, MA (US)

(72) Inventors: Orly Eshach Adiv, Atlit (IL); Camille Bedrosian, Woodbridge, CT (US); Hagit Baris Feldman, Kochav Yair (IL); Alina Kurolap, Haifa (IL); Susan Faas McKnight, Old Lyme, CT (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 244 days.

(21) Appl. No.: 16/614,582

(22) PCT Filed: May 21, 2018

(86) PCT No.: PCT/US2018/033678
§ 371 (c)(1),
(2) Date: Nov. 18, 2019

(87) PCT Pub. No.: WO2018/217638
PCT Pub. Date: Nov. 29, 2018

(65) Prior Publication Data
US 2020/0172603 A1 Jun. 4, 2020

Related U.S. Application Data

(60) Provisional application No. 62/509,576, filed on May 22, 2017.

(51) Int. Cl.
*C07K 16/18* (2006.01)
*A61P 1/00* (2006.01)
*A61K 39/00* (2006.01)

(52) U.S. Cl.
CPC .......... *C07K 16/18* (2013.01); *A61P 1/00* (2018.01); *A61K 2039/505* (2013.01); *A61K 2039/54* (2013.01); *A61K 2039/545* (2013.01); *C07K 2317/24* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | |
|---|---|---|
| 6,355,245 B1 | 3/2002 | Evans et al. |
| 9,718,880 B2 | 8/2017 | Bell et al. |
| 9,725,504 B2 | 8/2017 | Bell et al. |
| 9,732,149 B2 | 8/2017 | Bell et al. |
| 10,590,189 B2 | 3/2020 | Bell et al. |
| 10,703,809 B1 | 7/2020 | Bell et al. |
| 2012/0225056 A1* | 9/2012 | Rother ............... A61K 39/3955 424/133.1 |
| 2012/0237515 A1 | 9/2012 | Bell et al. |
| 2016/0244516 A1 | 8/2016 | Bell et al. |
| 2016/0376355 A1 | 12/2016 | Bell et al. |
| 2017/0015741 A1 | 1/2017 | Bell et al. |
| 2017/0349652 A1 | 12/2017 | Bell et al. |
| 2019/0256915 A1* | 8/2019 | Lenardo ............... C12Q 1/6851 |
| 2020/0199211 A1 | 6/2020 | Bell et al. |
| 2020/0392216 A1 | 12/2020 | Bell et al. |

FOREIGN PATENT DOCUMENTS

WO 2018/053039 A1 3/2018
WO 2018217638 A1 11/2018

OTHER PUBLICATIONS

Alexander J S et al., "Gastrointestinal lymphatics in health and disease," Pathophysiology, vol. 17(4):315-335 (2010).
Braamskamp, M. et al., "Clinical practice; Protein-losing enteropathy in children," European Journal of Pediatrics, vol. 169(10):1179-1185 (2010).
Cavero, T. et al., "Eculizumab in secondary atypical haemolytic uraemic syndrome," Nephrology Dialysis Transplantation, vol. 32(3): 466-474 (2017).
Comrie W. et al., "Inherited CD55 Deficiency in Patients with Early Onset Protein-Losing Enteropathy and Thrombosis," The Journal of Immunology, vol. 198(1):Suppl. S:1 page (2017).
Copland, A. et al., "Protein Losing Enteropathy: Diagnosis and Management," Practical Gastroenterology, Pediatric Allergy and Immunology, Nutrirtion Issues in Gastroenterology, Series #162 22-37 (2017).
Dezern, A. et al., "Paroxysmal Nocturnal Hemoglobinuria: A complement-mediated hemolytic anemia," Complement-Mediated Hemolytic Anemias, 479-494 (2015).
International Preliminary Report on Patentability, PCT/US2018/033678, dated Nov. 26, 2019, 10 pages.
International Search Report and Written Opinion, PCT/US2018/033678, dated Jul. 31, 2018, 17 pages.
Itoi, K., et al., "Protein-losing gastroenteropathy in association with immune deposits in gastrointestinal mucosal capillaries," The American Journal of Gastroenterology, vol. 84(2): 187-191 (1989).
Kurolap, A. et al., "Loss of CD55 in Eculizumab-Responsive Protein-Losing Enteropathy," New England Journal of Medicine, vol. 377(1):87-89 (2017).
Nih/national Institute Of Allergy And Infectious Diseases Featured: "Scientists identify cause, possible treatment for life-threatening gut condition," (2017)Retrieved from the Internet: <URL:https://medicalxpress.com/news/2017-06-scientists-treatment-life-threatening-gut> -condition.html [retrieved on Jul. 11, 2018].

(Continued)

Primary Examiner — Phillip Gambel
(74) Attorney, Agent, or Firm — Nelson Mullins Riley & Scarborough LLP; Jane E. Remillard, Esq.; Jill Gorny Sloper, Esq.

(57) ABSTRACT

Provided are methods for clinical treatment of a protein-losing enteropathy, such as lymphangiectasia, using an anti-C5 antibody, or antigen binding fragment thereof, in patients (e.g., pediatric patients).

17 Claims, 35 Drawing Sheets
Specification includes a Sequence Listing.

(56) References Cited

OTHER PUBLICATIONS

Ozen, A., et al., "CD55 Deficiency, Early-Onset Protein-Losing Enteropathy, and Thrombosis," New England Journal of Medicine, vol. 377(1):52-61 (2017).
Pu, J. et al., "Paroxysmal Nocturnal Hemoglobinuria from Bench to Bedside," Clinical and Translational Science, vol. 4(3): 219-224 (2011).
Vignes S. et al.,"Primary intestinal lymphangiectasia (Waldmann's disease)," Orphanet Journal of Rare Diseases, vol. 3(1): 8 pages (2008).
Wood, M.L. et al., "Protein losing enteropathy due to systemic lupus erythematosus," GUT, vol. 25(9):1013-1015 (1984).
Yokose, N. et al., "Protein-losing gastroenteropathy: unusual presentation of multiple myeloma," Annals of Hematology, vol. 88(7):705-707 (2018).

\* cited by examiner

| | | Disease onset | Critical state prior treatment | | | Eculizumab treatment | | | | |
|---|---|---|---|---|---|---|---|---|---|---|
| Week | | | | | 1 | | 2 | | 3 | 4 | 5 |
| Day | Low | | | 1 | 4 | 8 | 11 | 15 | 22 | 29 |
| | High | | | | | | | | | | |
| Date | | | | 12.02.17 | 15.02.17 | 19.02.17 | 22.02.17 | 26.02.17 | 05.03.17 | 12.03.17 |
| Time | | | | 10:30 | 9:35 | 10:40 | 10:30 | 11:10 | 10:00 | 10:45 |
| Dose (mg) | | | | 1200 | 1200 | 1200 | 1200 | 1200 | 1200 | 1200 |
| Blood pressure | | | | 107/67 | 115/73 | 113/74 | 115/65 | 110/61 | 121/72 | 120/69 |
| Pulse (bpm) | | | | 65 | 89 | 98 | 77 | 93 | 74 | 88 |
| Temp (°C) PO | | | | 36.1 | 36.5 | 36.5 | 36.9 | 36.6 | 36.6 | 37.1 |
| SO2 (%) | | | | 100 | 100 | 100 | 100 | 100 | 100 | 100 |
| Oxygen source | | | | None | None | None | None | None | None | None |
| Stomach perimeter (cm) | | | | 81/88 | 79/87 | 86/91 | 83.5/88.5 | 85/89 | 83/86 | 82/85 |
| Weight (Kg) | | | | 44.4 | 45 | 51.8 | 51.4 | 51.2 | 52.906 | 53.7 |
| Height (cm) | | | | 167 | X | X | X | 169 | 169 | X |
| BMI | | | | 15.9 | X | X | X | 17.9 | | X |
| #stool/day (approx.) | | | | >10 | 10 | 9-10 | 8 | 5 | 5 | 5 |
| Stool consistency | | | | Liquid | Liquid-soft | Liquid-soft | Soft-normal | Normal | Normal | Normal |
| Nutrition | | | | PO | PO | PO | PO | PO | PO | PO |
| Before treatment | Norm | | | 9:55 | 9:00 | 10:05 | 9:10 | 9:55 | 9:10 | 9:10 |
| Eculizumab level (PK) | | | | | | | | | | |
| Free C5 (PD) | | | | 3.2 | 3.2 | 3.1 | 3.3 | 3.6 | 3.8 | 4 |
| Albumin | 3.5-5.2 | | | | | | | | | |

| | | | | | | | |
|---|---|---|---|---|---|---|---|
| Total protein | 6.4–8.3 | 6.07 | 6.16 | 6.13 | 6.5 | 6.89 | 7 | 7.3 |
| Createnine | 0.7–1.3 | 0.57 | 0.5 | 0.49 | 0.53 | 0.53 | 0.61 | 0.68 |
| BUN | 8–26 | 7 | 8 | 5 | 6 | 7 | 7 | 10 |
| LDH | 125–220 | X | 239 | 271 | 294 | 276 | 287 | 347 |
| CRP | 0–0.5 | X | 0.45 | 0.81 | 0.77 | X | 0.35 | 0.23 |
| Hb | 13–17 | 13.6 | 12 | 10.7 | 11.5 | 11.3 | 10.9 | 11 |
| HCT | 39–49.5 | 40.9 | 37.7 | 34.9 | 35.8 | 36 | 35.3 | 35.8 |
| PLT | 130–350 | 39.3 | 351 | 329 | 268 | 334 | 259 | 308 |
| WBC | 4–10.8 | 8.42 | 7.89 | 7.11 | 5.55 | 6.76 | 6.52 | 5.49 |
| Lymphocytes | 1–3 | 1.86 | 0.72 | 1.44 | 1.3 | 1.55 | 1.52 | 1.25 |
| Reticulocytes | 0.03–0.08 | X | 0.11 | 0.1 | 0.09 | X | 0.13 | X |
| Schistocytes | smear | X | X | X | None | X | X | X |
| IgA | 70–350 | 250 | 242 | 251 | 273 | 281 | 289 | |
| IgM | 40–280 | 64 | 121 | 124 | 125 | 118 | 123 | |
| IgG | 680–1560 | 977 | 1030 | 1080 | 1270 | 1350 | 1400 | |
| IgE | 0–32 | X | 8.71 | X | 5.25 | 6.48 | 5.77 | |
| C3 | 72–156 | 140 | 132 | 136 | 131 | 122 | 117 | |
| C4 | 13–37 | 27.5 | 25.9 | 25.6 | 25.9 | 22.7 | 21.3 | |
| Fibrinogen | 160–400 | 400 | 391 | 309.3 | 309.3 | 305 | 267.8 | 244 |
| D–dimers | 0–0.5 | 0.51 | 0.57 | 1.86 | 1.72 | 0.71 | 0.64 | 0.54 |
| Haptoglobin | 30–200 | 171.2 | 167.6 | 158.2 | 163.8 | 147.9 | | |
| sTNFR1 | | | | | | | | |

From FIG.1A

From FIG.1B

| After treatment | | 12:40 | 11:50 | 12:50 | 12:50 | 13:15 | 12:00 | 13:00 |
|---|---|---|---|---|---|---|---|---|
| Eculizumab level (PK) | | | | | | | | |
| Free C5 (PD) | | | | | | | | |
| Other | Norm | 9:55 | 9:00 | 10:05 | 9:10 | 9:55 | 9:10 | 9:10 |
| PH | 7.35-7.45 | 7.3 | X | X | X | X | X | X |
| PCO2 | 35-45 | 57 | X | X | X | X | X | X |
| HCO3 | 22-26 | 28 | X | X | X | X | X | X |
| Lactate | 0-1.3 | 2 | X | X | X | X | X | X |
| Na | 133-145 | 136 | 137 | 141 | 140 | 140 | 141 | 139 |
| K | 3.5-5.3 | 3.8 | 4.3 | 4.2 | 5 | 4.7 | 4.4 | 5 |
| Ca | 8.4-10.2 | 8.4 | 8.5 | 8.3 | 8.2 | 8.9 | 8.9 | 9 |
| Inorganic phos | 2.3-4.7 | 4.11 | 3.29 | 3.7 | 4.81 | 4.22 | 4.93 | 4.89 |
| Mg | 1.6-2.6 | 1.59 | 1.65 | 1.53 | 1.46 | 1.85 | 1.97 | 1.91 |
| Iron | 65-175 | 22 | 43 | 21 | 44 | 29 | 21 | 38 |
| Ferritin | 30-300 | 16 | 70 | 39 | 24 | 23 | 19 | 23 |
| Transferrin | 175-380 | 302 | 289 | 307 | 309 | 329 | 335 | 322 |
| Total bilirubin | 0.2-1.2 | 0.2 | 0.15 | 0.15 | 0.28 | 0.28 | 0.49 | 0.47 |
| Direct bilirubin | 0-0.5 | 0.11 | <0.1 | <0.1 | 0.11 | 0.14 | 0.23 | 0.17 |
| ALP | 40-150 | 152 | 131 | 139 | 145 | 144 | 134 | 165 |
| ALT (GPT) | 0-55 | 41 | 36 | 40 | 36 | 32 | 30 | 23 |
| AST (GOT) | 5-34 | 43 | 35 | 34 | 37 | 30 | 27 | 35 |
| GGT | 12-64 | 53 | 53 | 81 | 66 | 62 | 46 | 31 |

From FIG.1C

| | | | | | | | |
|---|---|---|---|---|---|---|---|
| Amylase | 25–125 | | X | 191 | 169 | 113 | 149 | 127 | 150 |
| Total cholesterol | 140–200 | | X | 187 | 166 | 163 | 146 | 130 | 119 |
| HDL cholesterol | 30–65 | | X | 47.1 | 42.8 | 40.6 | 40.3 | 34.9 | 31.7 |
| Triglycerides | 30–170 | | X | 136 | 109 | 53 | 63 | 69 | 98 |
| Additional treatment | Dose | | | | | | | | |
| Albumin | 10 gr | | | | | | | | |
| Packed cells | | 13.02.17 | | | | | | | |
| Ferrlecit | 62.5 mg | | | | | | v | | |
| IV Vitamins | | | | | | | | | |
| Adverse reactions | | | | | | | | | |
| Meningococcal infection | | | | | | | | | |
| Thrombotic events | | | | | | | | | |
| Allergic reaction | | | | v | | | | | |
| Headache | | | | | | | | | |
| Hypertension | | | | | | | | | |
| Nausea/vomiting | | | | | | | | | |
| Cold symptoms | | | | | | | | | |
| Other | | | | | | | | | |
| Comments | | | | | | | | | |
| Infections | | | | | | | | | |

FIG.1D

| | Norm | Disease onset | Critical state prior treatment | Eculizumab treatment | | | | | | | |
|---|---|---|---|---|---|---|---|---|---|---|---|
| Week | Low / High | | | 1 | | 2 | | 3 | 4 | 5 | 7 |
| Day | | | | 1 | 4 | 8 | 11 | 15 | 22 | 29 | 43 |
| Date | | | | 29.01.17 | 01.02.17 | 05.02.17 | 08.02.17 | 12.02.17 | 19.02.17 | 26.02.17 | 12.03.17 |
| Time | | | | 14:25 | 10:25 | 10:30 | 10:20 | 10:20 | 11:05 | 11:40 | 11:30 |
| Dose (mg) | | | | 600 | 600 | 600 | 600 | 600 | 600 | 600 | 600 |
| Blood pressure | | | | 134/55 | 98/46 | 82/45 | 95/48 | 82/69 | 97/47 | 104/51 | 102/41 |
| Pulse (bpm) | | | | 134 | 98 | 83 | 65 | 110 | 100 | 101 | 102 |
| Temp (°C) AX | | | | 37.1 | 36.7 | 36.7 | 36.3 | 37.3 | 36.4 | 36.9 | 36.5 |
| SO2 (%) | | | | 99 | 100 | 100 | 100 | 100 | 96 | 100 | 100 |
| Oxygen source | | | | None | None | None | None | None | None | None | None |
| Weight (kg) | | | | 29 | 31.2 | 30 | 30.35 | 30.8 | 32 | 31 | 34 |
| Height (cm) | | | | X | X | X | X | X | X | X | X |
| BMI | | | | X | X | X | X | X | X | X | X |
| #stool/day (approx.) | | | | None | 1 | 2 | 1 | 0 | 1 | 1 | 2 |
| Stool consistency | | | | N/A | Soft | Normal | Soft | N/A | Soft-normal | | Normal |
| Nutrition | | | | TPN+PO liquids | TPN+PO | TPN+PO | TPN+PO | TPN+PO | TPN+PO | TPN+PO | TPN+PO |
| Before treatment | | | | 13:55 | 10:20 | 10:25 | 10:15 | 10:00 | 11:00 | 11:30 | 11:25 |
| Eculizumab level (PK) | | | | 1.5 | 1.3 | 1.8 | 2.1 | 2.2 | 2.3 | 2.7 | 3 |
| Free C5 (PD) | | | | | | | | | | | |
| Albumin | 3.8–5.4 | | | | | | | | | | |

From FIG.2A

| | | | | | | | | | |
|---|---|---|---|---|---|---|---|---|---|
| Total protein | 6.4–8.3 | 3.8 | 3.79 | 5.16 | 5.79 | 5.62 | 6.1 | 6.69 | 6.87 |
| Createnine | 0.57–1.11 | 0.37 | 0.57 | 0.42 | 0.4 | 0.73 | 0.42 | 0.42 | 0.49 |
| BUN | 7–20 | 29 | 23 | 12 | 19 | 18 | 16 | 20 | 19 |
| LDH | 125–220 | 121 | 113 | 125 | 122 | 112 | 113 | 128 | 151 |
| CRP | 0–0.5 | 10.14 | 2.7 | 3.14 | x | 4.21 | x | 13.94 | 3.76 |
| Hb | 12–14 | 9.2 | 6.7 | 7.3 | 7.5 | 8 | 7.9 | 7.9 | 8.6 |
| HCT | 35–45 | 30.9 | 22.8 | 23.8 | 25.1 | 23.2 | 25.8 | 26.2 | 28.6 |
| PLT | 200–370 | 224 | 175 | 170 | 215 | 228 | 220 | 246 | 229 |
| WBC | 5–13 | 13.76 | 4.35 | 4.95 | 4.89 | 6.22 | 5.98 | 6.08 | 5.44 |
| Lymphocytes | 1.16–4.28 | 2.26 | 1.35 | 1.87 | 1.63 | 1.76 | 1.83 | 1.85 | 2.01 |
| Reticulocytes | 0.01–0.05 | x | x | 0.15 | 0.13 | 0.08 | 0.01 | x | x |
| Schistocytes | smear | x | x | None | x | x | x | x | x |
| IgA | 70–350 | 221 | 228 | 311 | 328 | 292 | 314 | x | 315 |
| IgM | 40–280 | 143 | 113 | 124 | 124 | 106 | 119 | x | 141 |
| IgG | 680–1560 | 796 | 844 | 1330 | 1600 | 1640 | 1720 | x | 2000 |
| IgE | 1.4–300 | 91.6 | 77.2 | 81.5 | 104 | 113 | 178 | x | 96.4 |
| C3 | 72–156 | 118 | 109 | 134 | 144 | 136 | 146 | x | 149 |
| C4 | 13–37 | 24.6 | 20.6 | 25.1 | 27.4 | 24.6 | 28.2 | x | 24.8 |
| Fibrinogen | 160–400 | 400 | 348.6 | 451.3 | x | 451.3 | 419.2 | 475.2 | 419.2 |
| D–dimers | 0–0.5 | 1.96 | 1.04 | 0.72 | 0.19 | 1.01 | x | 1.52 | 1.49 |
| Haptoglobin | 30–200 | 200.4 | 155.2 | 165.2 | 185.3 | 170 | 287.4 | 280.7 | x |
| sTNFR1 | | | | | | | | | |

From FIG.2B

| After treatment | | 16:30 | 12:30 | 12:30 | 12:35 | 12:45 | 13:20 | 13:45 | 13:30 |
|---|---|---|---|---|---|---|---|---|---|
| Eculizumab level (PK) | | | | | | | | | |
| Free C5 (PD) | | | | | | | | | |
| Other | Norm | 13:55 | 10:20 | 10:25 | 10:15 | 10:00 | 11:00 | 11:30 | 11:25 |
| pH | 7.35–7.45 | x | x | x | x | x | x | x | x |
| PCO2 | 35–45 | x | x | x | x | x | x | x | x |
| HCO3 | 22–26 | x | x | x | x | x | x | x | x |
| Lactate | 0–1.3 | x | x | x | x | x | x | x | x |
| Na | 133–145 | 140 | 136 | 133 | 136 | 128 | 134 | 135 | 135 |
| K | 3.5–5.3 | 3.3 | 5.5 | 4.1 | 3.9 | 5.9 | 4.1 | 4.2 | 4.9 |
| Ca | 8.8–11 | 8.2 | 8.4 | 8.4 | 9.6 | 9.7 | 8.6 | 8.9 | 9.1 |
| Inorganic phos | 3.5–6.5 | 5.29 | 5.39 | 6.5 | 7.16 | 6.59 | 5.64 | 5.49 | 6.65 |
| Mg | 1.6–2.6 | x | 1.81 | 1.35 | 1.74 | 2.32 | 1.62 | 1.65 | 1.9 |
| Iron | 50–170 | 8 | 13 | 15 | 21 | x | 10 | x | 29 |
| Ferritin | 15–300 | 220 | 159 | 168 | 159 | x | 308 | x | 136 |
| Transferrin | 180–390 | 97 | 108 | 179 | 184 | x | 162 | x | 212 |
| Total bilirubin | 0.2–1.2 | 0.88 | 0.38 | 0.56 | 0.59 | 0.64 | 0.77 | 0.92 | 1.49 |
| Direct bilirubin | 0–0.5 | 0.66 | 0.16 | 0.24 | 0.34 | 0.42 | 0.53 | 0.64 | 0.92 |
| ALP | 62–280 | 643 | 384 | 608 | 413 | 363 | 311 | 395 | 432 |
| ALT (GPT) | 0–55 | 70 | 38 | 93 | 36 | 20 | 29 | 27 | 27 |
| AST (GOT) | 5–34 | 54 | 29 | 31 | 18 | 20 | 25 | 20 | 27 |
| GGT | 9–36 | 377 | 221 | 229 | 157 | 154 | 168 | 258 | 227 |

From FIG.2C

| | | | | | | | | | | |
|---|---|---|---|---|---|---|---|---|---|---|
| Amylase | 25-125 | | 22 | 47 | 65 | 81 | 94 | 63 | 70 | 71 |
| Total cholesterol | 140-200 | | 97 | 103 | 160 | 150 | 127 | 103 | 121 | 141 |
| HDL cholesterol | 35-80 | | 6 | 10 | 18.1 | 16.3 | 15.8 | 7.1 | 8.2 | 15 |
| Triglycerides | 0-150 | | 213 | 237 | 175 | 115 | 115 | 179 | 178 | 116 |
| Additional treatment | Dose | | | | | | | | | |
| Albumin | 10 gr | | | | | | | | | |
| Packed cells | | | | | | | 17.02.17 | | | |
| Ferrlecit (IV Iron) | 31.125 mg | | | 02.02.17 | | | | | | |
| Adverse reactions | | | | | | | | | | |
| Meningococcal infection | | | | | | | | | | |
| Thrombotic events | | | | | | | | | | |
| Allergic reaction | | | | | | | | | | |
| Headache | | | | | | | | | | |
| Hypertension | | | | | | | | | | |
| Nausea/vomiting | | | | | | | | | | |
| Cold symptoms | | | | | | | | | | |
| Other | | | | | | | | | | |
| Comments | | | Angry at staff over checkups | | | | | | | |
| Infections | | | Peritonitis | | | | | | Operation wound infection | |

FIG.2D

Albumin

| Treatment day | Low norm | High norm | Albumin (g/dL) |
|---|---|---|---|
| 0 | 3.8 | 5.4 | 1.3 |
| 1 | 3.8 | 5.4 | 1.5 |
| 4 | 3.8 | 5.4 | 1.3 |
| 8 | 3.8 | 5.4 | 1.8 |
| 11 | 3.8 | 5.4 | 2.1 |
| 15 | 3.8 | 5.4 | 2.2 |
| 22 | 3.8 | 5.4 | 2.3 |
| 29 | 3.8 | 5.4 | |
| 43 | 3.8 | 5.4 | |
| 57 | 3.8 | 5.4 | |
| 71 | 3.8 | 5.4 | |
| 85 | 3.8 | 5.4 | |
| 99 | 3.8 | 5.4 | |
| 113 | 3.8 | 5.4 | |
| 127 | 3.8 | 5.4 | |
| 141 | 3.8 | 5.4 | |
| 155 | 3.8 | 5.4 | |
| 169 | 3.8 | 5.4 | |
| 183 | 3.8 | 5.4 | |

Total protein

| Treatment day | Low norm | High norm | Total protein (g/dL) |
|---|---|---|---|
| 0 | 6.4 | 8.3 | 3.79 |
| 1 | 6.4 | 8.3 | 3.8 |
| 4 | 6.4 | 8.3 | 3.79 |
| 8 | 6.4 | 8.3 | 5.16 |
| 11 | 6.4 | 8.3 | 5.79 |
| 15 | 6.4 | 8.3 | 5.62 |
| 22 | 6.4 | 8.3 | 6.1 |
| 29 | 6.4 | 8.3 | |
| 43 | 6.4 | 8.3 | |
| 57 | 6.4 | 8.3 | |
| 71 | 6.4 | 8.3 | |
| 85 | 6.4 | 8.3 | |
| 99 | 6.4 | 8.3 | |
| 113 | 6.4 | 8.3 | |
| 127 | 6.4 | 8.3 | |
| 141 | 6.4 | 8.3 | |
| 155 | 6.4 | 8.3 | |
| 169 | 6.4 | 8.3 | |
| 183 | 6.4 | 8.3 | |

Weight

| Treatment day | Weight (kg) |
|---|---|
| 1 | 29 |
| 4 | 31.2 |
| 8 | 30 |
| 11 | 30.35 |
| 15 | 30.8 |
| 22 | |
| 29 | |
| 43 | |
| 57 | |
| 71 | |
| 85 | |
| 99 | |
| 113 | |
| 127 | |
| 141 | |
| 155 | |
| 169 | |
| 183 | |

|  |  | Disease onset | Critical state prior treatment | Eculizumab treatment | | | | | |
|---|---|---|---|---|---|---|---|---|---|
| Week |  |  |  |  | 1 | | 2 | | 3 |
| Day | Low |  | X | X | 1 | 4 | 8 | 11 | 15 |
|  | High |  | X | X |  |  |  |  |  |
| Date |  | Jun/Jul 2016 | Nov-16 | 20.11.16 | 23.11.16 | 27.11.16 | 30.11.16 | 4.12.16 |
| Time |  | X | X | 20:10 | 10:50 | 11:00 | 9:55 | 10:00 |
| Dose (mg) |  | X | X | 600 | 600 | 600 | 600 | 600 |
| Blood pressure |  | 100/70 | 88/55 | 97/60 | 112/82 | 115/76 | 114/78 | 113/76 |
| Pulse (bpm) |  | 138 | 123 | 100 | 112 | 109 | 95 | 102 |
| Temp (°C) PR |  | 36.1 | 36.5 | 34.8 | 36.6 | 36 | 36.4 | 36.4 |
| SO2 (%) |  | 100 | 100 | 100 | 100 | 100 | 100 | 100 |
| Oxygen source |  | NC | NRB | NRB | NC | NC | NC | NC |
| Weight (Kg) |  | 10.2 | 10.2 | 10.26 | 10.1 | 10.26 | 10.25 | 9.5 |
| Height (cm) |  | X | X | X | X | X | X | X |
| BMI |  | X | X | X | X | X | X | X |
| #stool/day (approx.) |  | 10 | 10 | 10 | 5 | 4 | 3-4 | 3-4 |
| Stool consistency |  | Watery | Watery | Watery | Watery | Soft | Soft | Soft |
| Nutrition |  | PO+PG | Fasting | Fasting | PG | PG | PG | PG |
| Before treatment | Norm |  |  | 13:40 | 9:20 | 9:40 | 9:45 | 9:35 |
| Eculizumab level (PK) |  | X | X | 0 | 481 | 705 | 1030 | 1180 |
| Free C5 (PD) |  | X | X | 110 | 0 | 0 | 0 | 0 |
| Albumin | 3.4-5 | 1.1 | 0.8 | 1.6 | 1.8 | 1.8 | 1.7 | 1.8 |
| Total protein | 6-8.2 | 3.3 | 3.2 | 3.7 | 4 | 4.1 | 4.2 | 4.8 |

From FIG.7A

| | | | | | | |
|---|---|---|---|---|---|---|
| Createnine | 0.7–1.3 | 0.09 | X | 0.29 | 0.32 | 0.22 | 0.14 | 0.23 |
| BUN | 5–20 | 8 | 4 | 6 | 5 | 4 | 3 | 3 |
| LDH | 60–225 | 187 | X | 367 | 294 | 301 | 380 | 298 |
| CRP | 0–5 | 6.74 | X | X | 33 | 12.7 | X | 2.34 |
| Hb | 11–14 | 13.2 | 8.8 | 8.4 | 6.9 | 9.2 | 8.1 | 7.5 |
| HCT | 34–40 | 39.3 | 26.5 | 26.6 | 21.8 | 28.1 | 26.8 | 23.9 |
| PLT | 200–450 | 815 | 354 | 68 | 109 | 95 | 189 | 356 |
| WBC | 5–14 | 15.94 | 15.59 | 15.06 | 9.34 | 10.91 | 10.56 | 14.16 |
| Lymphocytes | 1.13–5.52 | 3.83 | 5.16 | 2.93 | 3.69 | 2.68 | 3.01 | 4.25 |
| Reticulocytes | 0.03–0.08 | X | X | 0.06 | 0.03 | 0.03 | X | 0.04 |
| Schistocytes | smear | X | X | None | None | None | X | None |
| IgA | 70–350 | 88.8 | X | X | 185 | 174 | X | 240 |
| IgM | 40–280 | 32.3 | X | X | 48.5 | 47.9 | X | 69 |
| IgG | 680–1560 | 225 | X | X | 410 | 475 | X | 680 |
| IgE | 0–32 | X | X | X | 155 | 141 | X | 1.39 |
| C3 | 72–156 | 88 | X | X | 60 | 61 | X | 94 |
| C4 | 13–37 | 33.9 | X | X | 62.9 | 48.3 | X | 56.5 |
| Fibrinogen | 160–400 | 272.9 | X | X | 95.2 | 153.1 | X | 244 |
| D–dimers | 0–0.5 | X | X | X | X | 3.01 | X | 2.31 |
| Haptoglobin | 30–200 | X | X | X | 77.4 | 96.7 | X | X |
| sTNFR1 | | | X | | | | | |
| After treatment | | | | 22:30 | 13:20 | 13:10 | 12:00 | 12:10 |

| | Norm | | | 942 | 1440 | 1670 | 2420 | 1750 |
|---|---|---|---|---|---|---|---|---|
| Eculizumab level (PK) | | x | x | 942 | 1440 | 1670 | 2420 | 1750 |
| Free C5 (PD) | | x | x | 0 | 0 | 0 | 0 | 0 |
| Other | Norm | | | 13:40 | 9:20 | 9:40 | 9:45 | 9:35 |
| PH | 7.35–7.45 | 7.53 | | 7.17 | 7.46 | x | x | 7.39 |
| PCO2 | 35–45 | 38 | | 88 | 47 | x | x | 59 |
| HCO3 | 22–26 | 31.8 | | 32.1 | 33.4 | x | x | 35.7 |
| Lactate | 0–1.3 | 1.1 | | 2.8 | 2.2 | x | x | 0.9 |
| Na | 133–145 | 136 | 130 | 143 | 144 | 143 | 148 | 142 |
| K | 3.5–5.3 | 5.1 | 4.1 | 4.2 | 4.4 | 4.2 | 4.1 | 4.1 |
| Ca | 8.5–10.8 | 8.2 | 7 | 6.9 | 7.4 | 7.3 | 7.7 | 7.9 |
| Inorganic phos | 3.5–6.5 | 6.2 | 4 | 3.5 | 3.2 | 3.6 | 3.7 | 3.3 |
| Mg | 1.3–2.4 | 1.61 | 1.32 | 1.4 | 1.61 | 1.23 | 1.51 | 1.35 |
| Iron | 50–150 | 111 | 35 | x | 38 | 33 | x | x |
| Ferritin | 15–300 | 20 | 41 | x | 66 | 83 | x | x |
| Transferrin | 210–390 | 118 | 98 | x | 34 | 43 | x | x |
| Total bilirubin | 0.2–1 | 0.1 | x | 0.1 | 0.09 | 0.2 | 0.12 | 0.1 |
| Direct bilirubin | 0–0.2 | <0.05 | x | <0.05 | <0.05 | 0.07 | <0.05 | <0.05 |
| ALP | 50–160 | 67 | 92 | 181 | 155 | 146 | 130 | 164 |
| ALT (GPT) | 14–63 | 22 | 17 | 30 | 38 | 33 | 95 | 38 |
| AST (GOT) | 5–40 | 32 | 22 | 31 | 28 | 27 | 33 | 68 |
| GGT | 5–60 | 9 | 115 | 52 | 52 | 55 | 54 | 104 |
| Amylase | 30–140 | 6 | x | 3 | 2 | 3 | 2 | 4 |

From FIG.7B

| | | | | | | | |
|---|---|---|---|---|---|---|---|
| Total cholesterol | 140-200 | 152 | | x | 57 | 72 | 90 | 122 |
| HDL cholesterol | 30-65 | 22 | | x | 5 | 28 | 50 | 60 |
| Triglycerides | 30-170 | 492 | | x | 145 | 115 | 121 | 166 |
| Zinc | 60-120 | x | | x | x | x | x | x |
| Vitamin A | 20-43 | x | | x | x | x | x | x |
| Vitamin E | 0.5-1 | x | | x | x | x | | x |
| Additional treatment | Dose | | | | | | | |
| Albumin | 10 gr | | | v | v | | | |
| Packed cells | | | | | 24.11.16 | | | |
| IV Vitamins | | | | | | Yes (daily, when IV access available) | | |
| Adverse reactions | | | | | | | | |
| Meningococcal infection | | | | | | | | |
| Thrombotic events | | Sinus vein thrombosis | | | | | | |
| Allergic reaction | | | | | | | | |
| Headache | | | | | | | | |
| Hypertension | | | | | Mild | Mild | Mild | Mild |
| Nausea/vomiting | | | | | | | | |
| Cold symptoms | | | | | | | | |
| Other | | | | | | | | |
| Comments | | | | | "White coat syndrome": mild HTN prior treatment (post blood draw), with normal measurements during the day. | | | |
| Infections | | | | | | | | |

From FIG.7A

| | 4 | 5 | New lab norms | 7 | 9 | 11 | 13 | 15 | 17 |
|---|---|---|---|---|---|---|---|---|---|
| | 22 | 29 | | 43 | 57 | 71 | 85 | 99 | 114 |
| | 11.12.16 | 18.12.16 | | 01.01.17 | 15.01.17 | 29.01.17 | 12.02.17 | 26.02.17 | 13.03.17 |
| | 9:10 | 11:25 | | 10:35 | 10:40 | 11:05 | 10:20 | 11:10 | 10:00 |
| | | | | Eculizumab treatment | | | | | |
| | 600 | 600 | | 600 | 600 | 600 | 600 | 600 | 600 |
| | 119/66 | 116/68 | | 108/58 | 94/69 | 102/66 | 94/54 | 122/75 | 115/60 |
| | 116 | 93 | | 91 | 112 | 105 | 125 | 120 | 110 |
| | 36.4 | 36.1 | | 37.2 | 37.1 | 36.9 | 37.3 | 36.7 | 37.1 |
| | 100 | X | | 99 | 97 | 98 | 98 | 100 | 98 |
| | NC | NC | | NC | NC | NC | NC | NC | NC |
| | 8.454 | 8.53 | | 8.5 | 9.14 | 9.835 | 10.35 | 10.75 | 10.76 |
| | X | X | | X | 83 | X | 84 | 84.5 | X |
| | X | X | | X | 13.27 | X | 14.7 | 15.1 | X |
| | 3-4 | 4-5 | | 3-4 | 3-4 | 3-4 | 3-4 | 3-4 | 3-4 |
| | Soft | Soft-Normal | | Soft-Normal | Soft-Normal | Soft-Normal | Soft-Normal | Soft | Soft |
| | PO+PG | PO+PG | | PO+PG | PO+PG | PO+PG | PO+PG | PG | PG |
| | 8:50 | 10:30 | New Norms | 10:15 | 9:25 | 10:20 | 9:40 | 10:45 | 9:55 |
| | 1.9 | 2.3 | 3.8-5.4 | 3.5 | 4.3 | 4.2 | 4 | 4.2 | 3.9 |
| | 5.6 | 6.3 | 6.4-8.3 | 6.25 | 7.32 | 7.15 | 6.85 | 7.12 | 6.65 |

From FIG.7A

| | | 0.7-1.3 | 0.37 | 0.4 | 0.41 | 0.39 | 0.42 | 0.36 |
|---|---|---|---|---|---|---|---|---|
| 0.22 | X | 8-26 | 8 | 12 | 11 | 11 | 8 | 7 |
| 271 | X | 125-220 | X | 222 | 311 | 236 | 228 | 260 |
| 1.64 | X | 0-0.5 | 0.06 | X | 0.06 | X | 0.63 | 10.09 |
| 7.6 | 8.4 | 11-14 | 8.2 | 9.6 | 8.9 | 8.5 | 9 | 8.9 |
| 23.6 | 27.1 | 34-40 | 26.3 | 31 | 28.2 | 27.6 | 30.6 | 29.2 |
| 689 | 646 | 200-450 | 673 | 541 | 505 | 504 | 528 | 303 |
| 16.54 | 13.49 | 5-14 | 8.64 | 7.03 | 11.25 | 9.54 | 12.61 | 10.3 |
| 2.81 | 3.28 | 1.13-5.52 | 3.38 | 1.83 | 3.1 | 2.88 | 1.7 | 2.01 |
| X | X | 0.03-0.08 | 0.05 | X | X | 0.03 | 0.06 | X |
| X | X | smear | X | X | None | X | X | X |
| 276 | X | 70-350 | 277 | 222 | X | X | 195 | 163 |
| 99.4 | X | 40-280 | 160 | 158 | X | X | 138 | 112 |
| 824 | X | 680-1560 | 859 | 768 | X | X | 708 | 635 |
| 128 | X | 0-32 | 91.5 | 63 | X | X | 62.6 | 72.2 |
| 108 | X | 72-156 | 116 | 124 | X | X | 127 | 119 |
| 67.9 | X | 13-37 | 60.5 | 53.8 | X | X | 56.5 | 55.1 |
| 288.8 | X | 160-400 | 249.5 | 244 | X | 343.1 | 292.8 | 451.3 |
| 2.17 | X | 0-0.5 | 2.39 | 0.54 | X | X | 0.5 | 0.35 |
| 137.3 | X | 30-200 | X | X | 175.7 | X | X | X |
| | | | X | X | X | X | X | |
| 11:15 | 13:45 | | 12:45 | 12:50 | 13:10 | 12:50 | 14:10 | 12:10 |

FIG. 7F

| 8:50 | 10:30 | New Norms | 10:15 | 9:25 | 10:20 | 9:40 | 10:45 | 9:55 |
|---|---|---|---|---|---|---|---|---|
| X | X | 7.35–7.45 | X | 7.37 | X | X | X | X |
| X | X | 35–45 | X | 61 | X | X | X | X |
| X | X | 22–26 | X | 35.3 | X | X | X | X |
| X | X | 0–1.3 | X | 1.2 | X | X | X | X |
| 140 | 140 | 133–145 | 140 | 137 | 140 | 141 | 142 | 138 |
| 4.8 | 4.3 | 3.5–5.3 | 4.6 | 4.9 | 4.9 | 4.7 | 4.2 | 4.3 |
| 8.2 | 8.7 | 8.8–11 | 9.6 | 10 | 9.7 | 9.8 | 10 | 9.5 |
| 4.9 | 5.9 | 3.5–6.5 | 5.53 | 5.66 | 6.24 | 5.76 | 5.58 | 5.28 |
| 1.52 | 1.45 | 1.6–2.6 | 2.22 | 2.24 | 2.53 | 2.33 | 2.1 | 2.13 |
| 51 | X | 50–150 | X | X | 65 | X | X | 21 |
| 69 | X | 15–300 | X | X | 23 | X | X | 61 |
| 115 | X | 210–390 | X | X | 310 | X | X | 291 |
| 0.1 | X | 0.2–1 | X | <0.1 | 0.11 | <0.1 | <0.1 | <0.1 |
| <0.05 | X | 0–0.5 | <0.1 | <0.1 | <0.1 | <0.1 | <0.1 | <0.1 |
| 163 | 148 | 127–517 | 138 | 144 | 165 | 174 | 193 | 176 |
| 44 | 29 | 0–55 | 8 | 26 | 31 | 11 | 14 | 14 |
| 27 | 23 | 5–34 | 19 | 35 | 30 | 21 | 21 | 24 |
| 147 | 101 | 12–64 | 36 | 37 | 46 | 30 | 25 | 29 |
| 4 | X | 30–140 | X | 15 | 17 | 14 | 14 | 11 |

FIG. 7G

| | | 142 | X | 140–200 | X | 193 | 165 | 166 | 169 | 146 |
|---|---|---|---|---|---|---|---|---|---|---|
| | | 77 | X | 30–65 | X | 59.1 | 53.5 | 60 | 64.6 | 58.8 |
| | | 180 | X | 30–170 | X | 197 | 121 | 73 | 61 | 78 |
| | | X | X | 60–120 | X | X | X | 110 | X | X |
| | | X | X | 20–43 | X | X | X | 62 | X | X |
| | | X | X | 0.5–1 | X | X | X | 1.9 | X | X |
| | | | | | | | | | | |
| | | | | | | | | | | |
| | | | | | | | | SVC syndrome | | |
| | | Mild | | | | | | | | |
| | | | | Pneumonia 25.12.16 | | | | | | |
| | | | | | | | | | | Viral UI |

FIG. 7H

Albumin

| Treatment day | Low norm | High norm | Albumin (g/dL) |
|---|---|---|---|
| 0 | 3.4 | 5 | 0.8 |
| 1 | 3.4 | 5 | 1.6 |
| 4 | 3.4 | 5 | 1.8 |
| 8 | 3.4 | 5 | 1.8 |
| 11 | 3.4 | 5 | 1.7 |
| 15 | 3.4 | 5 | 1.8 |
| 22 | 3.4 | 5 | 1.9 |
| 29 | 3.4 | 5 | 2.3 |
| 43 | 3.8 | 5.4 | 3.5 |
| 57 | 3.8 | 5.4 | 4.3 |
| 71 | 3.8 | 5.4 | 4.2 |
| 85 | 3.8 | 5.4 | 4 |
| 99 | 3.8 | 5.4 | |
| 113 | 3.8 | 5.4 | |
| 127 | 3.8 | 5.4 | |
| 141 | 3.8 | 5.4 | |
| 155 | 3.8 | 5.4 | |
| 169 | 3.8 | 5.4 | |
| 183 | 3.8 | 5.4 | |

Total protein

| Treatment day | Low norm | High norm | Total protein (g/dL) |
|---|---|---|---|
| 0 | 6 | 8.2 | 3.2 |
| 1 | 6 | 8.2 | 3.7 |
| 4 | 6 | 8.2 | 4 |
| 8 | 6 | 8.2 | 4.1 |
| 11 | 6 | 8.2 | 4.2 |
| 15 | 6 | 8.2 | 4.8 |
| 22 | 6 | 8.2 | 5.6 |
| 29 | 6 | 8.2 | 6.3 |
| 43 | 6 | 8.2 | 6.25 |
| 57 | 6.4 | 8.3 | 7.32 |
| 71 | 6.4 | 8.3 | 7.15 |
| 85 | 6.4 | 8.3 | 6.85 |
| 99 | 6.4 | 8.3 | |
| 113 | 6.4 | 8.3 | |
| 127 | 6.4 | 8.3 | |
| 141 | 6.4 | 8.3 | |
| 155 | 6.4 | 8.3 | |
| 169 | 6.4 | 8.3 | |
| 183 | 6.4 | 8.3 | |

PK/PD

| Treatment day | BK Baseline/Trough | PK Peak | PD Baseline/Trough | PD Peak |
|---|---|---|---|---|
| 1 | 0 | 942 | 110 | 0 |
| 4 | 481 | 1440 | 0 | 0 |
| 8 | 705 | 1670 | 0 | 0 |
| 11 | 1030 | 2420 | 0 | 0 |
| 15 | 1180 | 1750 | 0 | 0 |
| 57 | | | | |
| 71 | | | | |
| 85 | | | | |
| 99 | | | | |
| 113 | | | | |
| 127 | | | | |
| 141 | | | | |
| 155 | | | | |
| 169 | | | | |
| 183 | | | | |

Weight

| Treatment day | Weight (kg) |
|---|---|
| 1 | 10.26 |
| 4 | 10.1 |
| 8 | 10.26 |
| 11 | 10.25 |
| 15 | 9.5 |
| 22 | 8.454 |
| 29 | 8.53 |
| 43 | 8.5 |
| 57 | 9.14 |
| 71 | 9.835 |
| 85 | 10.35 |
| 99 | |
| 113 | |
| 127 | |
| 141 | |
| 155 | |
| 169 | |
| 183 | |

* Baseline time point sample required repeat analysis at 1:20 dilution for sTNFR1 quantitation because the initial analysis at a 1:10 dilution (assay MRD) was ALQ.
Note: HV = Healthy Volunteer range of values.

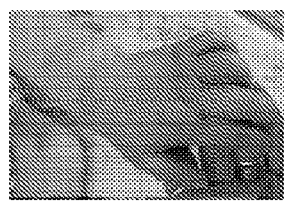
FIG.17E Eculizumab day 71
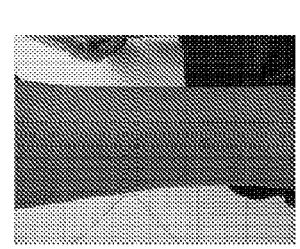
FIG.17J Eculizumab day —
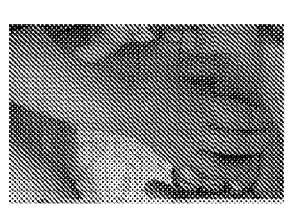
FIG.17D Eculizumab day 71
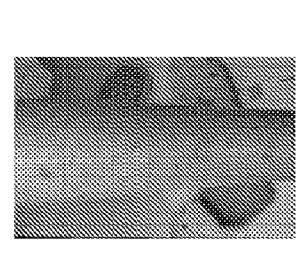
FIG.17I Eculizumab day 11
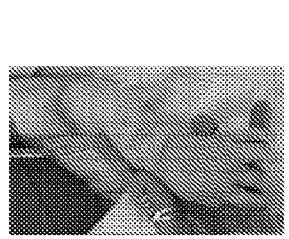
FIG.17C Eculizumab day 15
FIG.17H Pre-treatment
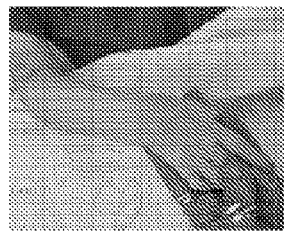
FIG.17B Eculizumab day 15
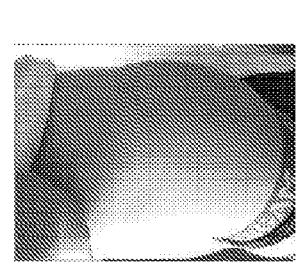
FIG.17G Eculizumab day 57
FIG.17A Pre-treatment
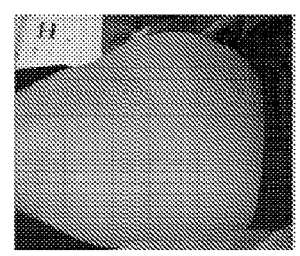
FIG.17F Pre-treatment Pre-treatment Eculizumab day 66

DOSAGE AND ADMINISTRATION OF ANTI-C5 ANTIBODIES FOR TREATMENT OF PROTEIN-LOSING ENTEROPATHY IN PATIENTS

CROSS-REFERENCE TO RELATED APPLICATIONS

This application is a 35 U.S.C. 371 national stage filing of International Application No. PCT/US2018/033678, filed on May 21, 2018, which claims the benefit of U.S. Provisional Application Ser. No. 62/509,576, filed on May 22, 2017, each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Nov. 15, 2019, is named AXJ-240US_Sequence_Listing.txt and is 25,205 bytes in size.

BACKGROUND

Protein-losing enteropathy (PLE) is a rare condition that is characterized by loss of protein and other nutrients through the intestinal tract. Patients with PLE may suffer from a variety of symptoms including edema, ascites, pleural effusion, pericarditis, lymphedema, diarrhea, abdominal pain, fatigue, weight loss and vitamin deficiency. PLE diagnosis is commonly based on clearance of fecal α-1 antitrypsin and treatment included management of symptoms and dietary modification.

PLE is not a single disease, but a complication that arises as a result of mucosal injury or an intestinal disorder. One such disorder is primary intestinal lymphangiectasia (also known as "intestinal lymphangiectasia," "primary intestinal lymphangiectasia" and "PIL"). Though adults may be diagnosed with lymphangiectasia, it is most commonly reported in children and young adults. Diagnosis is based on endoscopic evaluation and histopathological examination of tissue biopsy specimens. Current treatments include low-fat diet plans supplemented with medium-chain triglycerides (MCT), administration of octreotide, and serum albumin transfusions.

Patients with PLE (e.g., lymphangiectasia), are at risk of substantial morbidity and mortality. Accordingly, it is an object herein to provide methods for treating human patients (e.g., pediatric patients) with PLE (e.g., lymphangiectasia).

SUMMARY

Provided herein are compositions and methods for treating protein-losing enteropathy (e.g., lymphangiectasia) in a patient (e.g., a pediatric patient <18 years of age), comprising administering to the patient an anti-C5 antibody, or antigen binding fragment thereof, wherein the anti-C5 antibody, or antigen binding fragment thereof, is administered (or is for administration) according to a particular clinical dosage regimen (i.e., according to an initial high and frequent dosing regimen, followed by regular maintenance dosing as albumin levels normalize). In one embodiment, the patient has not previously been treated with a complement inhibitor (e.g., the patient is a complement inhibitor treatment-naïve patient).

An exemplary anti-C5 antibody is eculizumab (Soliris®). In other embodiments, the antibody comprises the heavy and light chain CDRs or variable regions of eculizumab. Accordingly, in one embodiment, the antibody comprises the CDR1, CDR2 and CDR3 domains of the VH region of eculizumab having the sequence set forth in SEQ ID NO:7, and the CDR1, CDR2 and CDR3 domains of the VL region of eculizumab having the sequence set forth in SEQ ID NO:8. In another embodiment, the antibody comprises heavy chain CDR1, CDR2 and CDR3 domains having the sequences set forth in SEQ ID NOs:1, 2 and 3, respectively, and light chain CDR1, CDR2 and CDR3 domains having the sequences set forth in SEQ ID NOs:4, 5 and 6, respectively. In another embodiment, the antibody comprises a VH region having the amino acid sequence set forth in SEQ ID NO:7. In another embodiment, the antibody comprises a VL region having the amino acid sequence set forth in SEQ ID NO:8. In another embodiment, the antibody comprises VH and VL regions having the amino acid sequences set forth in SEQ ID NO:7 and SEQ ID NO:8, respectively. In another embodiment, the antibody comprises the heavy chain constant region of eculizumab having the sequence set forth in SEQ ID NO:9. In another embodiment, the antibody comprises a heavy chain having the amino acid sequence set forth in SEQ ID NO:10. In another embodiment, the antibody comprises a light chain having the amino acid sequence set forth in SEQ ID NO:11. In another embodiment, the antibody comprises heavy and light chains having the amino acid sequences set forth in SEQ ID NO:10 and SEQ ID NO:11, respectively.

In another embodiment, the antibody competes for binding with, and/or binds to the same epitope on C5 as, the above-mentioned antibodies. In another embodiment, the antibody has at least about 90% variable region amino acid sequence identity with the above-mentioned antibodies (e.g., at least about 90%, 95% or 99% variable region identity with SEQ ID NO:7 and SEQ ID NO:8).

In one embodiment, the patient treated according to the methods described herein is an adult who is 18 years or older (≥18 years of age). In another embodiment, the patient treated according to the methods described herein is a pediatric patient who is less than 18 years of age (<18 years). In one embodiment, the pediatric patient is less than 12 years of age (<12 years). In another embodiment, the pediatric patient is less than 6 years of age (<6 years). In another embodiment, the pediatric patient is less than 2 years of age (<2 years). In another embodiment, the pediatric patient is less than 1, 2, 3, 4, 5, 6, 7, 8, 9, 10, 11, 12, 13, 14, 15, 16, 17 or 18 years of age.

In one embodiment, the dose of the anti-C5 antibody, or antigen binding fragment thereof, is based on the weight of the patient. For example, in one embodiment, about 300 mg, about 600 mg, about 900 mg, and/or about 1200 mg of the anti-C5 antibody, or antigen binding fragment thereof, is administered to a patient based on the patient's weight. In one embodiment, 300 mg or 600 mg of the anti-C5 antibody, or antigen binding fragment thereof, is administered to a patient weighing 10 kg to <20 kg. In another embodiment, 600 mg of the anti-C5 antibody, or antigen binding fragment thereof, is administered to a patient weighing 10 kg to <30 kg. In another embodiment, 600 mg of the anti-C5 antibody, or antigen binding fragment thereof, is administered to a patient weighing 20 kg to <30 kg. In another embodiment, 900 mg of the anti-C5 antibody, or antigen binding fragment thereof, is administered to a patient weighing 30 kg to <40 kg. In another embodiment, 1200 mg of the anti-C5 antibody, or antigen binding fragment thereof, is administered to a patient weighing ≥40 kg. In certain embodiments, dosage regimens are adjusted to provide the optimum desired response (e.g., an effective response).

In another embodiment, the anti-C5 antibody, or antigen binding fragment thereof, is administered for one or more administration cycles. In one embodiment, the administration cycle is 27 weeks.

In one embodiment, the treatment comprises an induction phase, wherein the anti-C5 antibody, or antigen binding fragment thereof, is administered twice per week for two weeks, followed by three weekly doses. In another embodiment, the induction phase is followed by a maintenance phase, wherein the anti-C5 antibody, or antigen binding fragment thereof, is administered every two weeks. In another embodiment, the anti-C5 antibody, or antigen binding fragment thereof, is administered twice per week during weeks 1 and 2 of the administration cycle, followed by once per week during weeks 3, 4 and 5 and every two weeks thereafter.

In another embodiment, a method of treating a human patient with protein-losing enteropathy (PLE) is provided, the method comprising administering to the patient during an administration cycle an effective amount of an anti-C5 antibody, or antigen binding fragment thereof, comprising CDR1, CDR2 and CDR3 heavy chain sequences as set forth in SEQ ID NOs:1, 2 and 3, respectively, and CDR1, CDR2 and CDR3 light chain sequences as set forth in SEQ ID NOs:4, 5 and 6, respectively, wherein the anti-C5 antibody, or antigen binding fragment thereof, is administered at a dose of: i) 600 mg to a patient weighing 10 kg to <20 kg twice per week during weeks 1 and 2 of the administration cycle and once during week 3, followed by 300 mg or 600 mg once per week during weeks 4 and 5 and every two weeks thereafter; ii) 600 mg to a patient weighing 20 kg to <30 kg twice per week during weeks 1 and 2 of the administration cycle, followed by 600 mg once per week during weeks 3, 4 and 5 and every two weeks thereafter; iii) 900 mg to a patient weighing 30 kg to <40 kg twice per week during weeks 1 and 2 of the administration cycle, followed by 900 mg once per week during weeks 3, 4 and 5 and every two weeks thereafter; or iv) 1200 mg to a patient weighing ≥40 kg twice per week during weeks 1 and 2 of the administration cycle, followed by 1200 mg once per week during weeks 3, 4 and 5 and every two weeks thereafter.

In another embodiment, a method of treating a human pediatric patient with lymphangiectasia is provided, the method comprising administering to the patient during an administration cycle an effective amount of an anti-C5 antibody, or antigen binding fragment thereof, comprising CDR1, CDR2 and CDR3 heavy chain sequences as set forth in SEQ ID NOs:1, 2 and 3, respectively, and CDR1, CDR2 and CDR3 light chain sequences as set forth in SEQ ID NOs:4, 5 and 6, respectively, wherein the anti-C5 antibody, or antigen binding fragment thereof, is administered at a dose of: i) 600 mg to a patient weighing 10 kg to <20 kg twice per week during weeks 1 and 2 of the administration cycle and once during week 3, followed by 300 mg or 600 mg once per week during weeks 4 and 5 and every two weeks thereafter; ii) 600 mg to a patient weighing 20 kg to <30 kg twice per week during weeks 1 and 2 of the administration cycle, followed by 600 mg once per week during weeks 3, 4 and 5 and every two weeks thereafter; iii) 900 mg to a patient weighing 30 kg to <40 kg twice per week during weeks 1 and 2 of the administration cycle, followed by 900 mg once per week during weeks 3, 4 and 5 and every two weeks thereafter; or iv) 1200 mg to a patient weighing ≥40 kg twice per week during weeks 1 and 2 of the administration cycle, followed by 1200 mg once per week during weeks 3, 4 and 5 and every two weeks thereafter.

In another embodiment, 600 mg of the anti-C5 antibody, or antigen binding fragment thereof, is administered to a patient weighing 10 kg to <30 kg.

In another embodiment, the anti-C5 antibody, or antigen binding fragment thereof, is administered to a patient weighing 10 kg to <20 kg at a dose of 600 mg twice per week during weeks 1 and 2 of the administration cycle and once during week 3, followed by 300 mg or 600 mg once per week during weeks 4 and 5 and every two weeks thereafter.

In another embodiment, the anti-C5 antibody, or antigen binding fragment thereof, is administered to a patient weighing 20 kg to <30 kg at a dose of 600 mg twice per week during weeks 1 and 2 of the administration cycle, followed by 600 mg once per week during weeks 3, 4 and 5 and every two weeks thereafter.

In another embodiment, the anti-C5 antibody, or antigen binding fragment thereof, is administered to a patient weighing 30 kg to <40 kg at a dose of 900 mg twice per week during weeks 1 and 2 of the administration cycle, followed by 900 mg once per week during weeks 3, 4 and 5 and every two weeks thereafter.

In another embodiment, the anti-C5 antibody, or antigen binding fragment thereof, is administered to a patient weighing ≥40 kg at a dose of 1200 mg twice per week during weeks 1 and 2 of the administration cycle, followed by 1200 mg once per week during weeks 3, 4 and 5 and every two weeks thereafter.

In another embodiment, the anti-C5 antibody, or antigen binding fragment thereof, is administered every two weeks after completion of the administration cycle. In another embodiment, the anti-C5 antibody, or antigen binding fragment thereof, is administered on a monthly basis (e.g., every four weeks) or every other month basis (e.g., every eight weeks) after completion of the administration cycle. In another embodiment, the anti-C5 antibody, or antigen binding fragment thereof, is administered on a monthly basis or every other month basis for a year after completion of the administration cycle. In another embodiment, the anti-C5 antibody, or antigen binding fragment thereof, is administered on a monthly basis or every other month basis for two, three, four or five years after completion of the administration cycle. In a particular embodiment, the anti-C5 antibody, or antigen binding fragment thereof, is administered on a monthly basis or every other month basis for up to two years after completion of the administration cycle.

In another aspect, the treatment regimens described are sufficient to maintain particular serum trough concentrations of the anti-C5 antibody, or antigen binding fragment thereof. For example, in one embodiment, the treatment maintains a serum trough concentration of the anti-C5 antibody, or antigen binding fragment thereof, of 50, 55, 60, 65, 70, 75, 80, 85, 90, 95, 100, 105, 110, 115, 120, 125, 130, 135, 140, 145, 150, 155, 160, 165, 170, 175, 180, 185, 190, 200, 205, 210, 215, 220, 225, 230, 240, 245, 250, 255, 260, 265, 270, 280, 290, 300, 305, 310, 315, 320, 325, 330, 335, 340, 345, 350, 355, 360, 365, 370, 375, 380, 385, 390, 395 or 400 µg/mL or greater. In one embodiment, the treatment maintains a serum trough concentration of the anti-C5 antibody, or antigen binding fragment thereof, of 100 µg/mL or greater. In another embodiment, the treatment maintains a serum trough concentration of the anti-C5 antibody, or antigen binding fragment thereof, of 150 µg/mL or greater. In another embodiment, the treatment maintains a serum trough concentration of the anti-C5 antibody, or antigen binding fragment thereof, of 200 µg/mL or greater. In another embodiment, the treatment maintains a serum trough concentration of the anti-C5 antibody, or antigen binding fragment thereof, of 250 µg/mL or greater. In another embodiment, the treatment maintains a serum trough concentration of the anti-C5 antibody, or antigen binding fragment thereof, of 300 µg/mL or greater. In another embodiment, the treatment maintains a serum trough concentration of the anti-C5 antibody, or antigen binding fragment thereof, of between 100 µg/mL and 200 µg/mL. In another embodiment, the treatment maintains a serum trough concentration of the anti-C5 antibody, or antigen binding fragment thereof, of about 175 µg/mL.

In another embodiment, to obtain an effective response, the anti-C5 antibody is administered to the patient in an amount and with a frequency to maintain at least 50 µg, 55 µg, 60 µg, 65 µg, 70 µg, 75 µg, 80 µs, 85 µs, 90 µs, 95 µg, 100 µg, 105 µs, 110 µs, 115 µg, 120 µg, 125 µg, 130 µs, 135 µg, 140 µg, 145 µs, 150 µg, 155 µg, 160 µs, 165 µg, 170 µs, 175 µg, 180 µs, 185 µg, 190 µg, 195 µg, 200 µs, 205 µg, 210 µg, 215 µg, 220 µg, 225 µs, 230 µg, 235 µs, 240 µg, 245 µg, 250 µg, 255 µg or 260 µg of antibody per milliliter of the patient's blood. In another embodiment, the anti-C5 antibody is administered to the patient in an amount and with a frequency to maintain between 50 µs and 250 µs of antibody per milliliter of the patient's blood. In another embodiment, the anti-C5 antibody is administered to the patient in an amount and with a frequency to maintain between 100 µg and 200 µg of antibody per milliliter of the patient's blood. In another embodiment, the anti-C5 antibody is administered to the patient in an amount and with a frequency to maintain about 175 µg of antibody per milliliter of the patient's blood.

In another embodiment, to obtain an effective response, the anti-C5 antibody is administered to the patient in an amount and with a frequency to maintain a minimum free C5 concentration. For example, in one embodiment, the anti-C5 antibody is administered to the patient in an amount and with a frequency to maintain a free C5 concentration of 0.2 µg/mL, 0.3 µg/mL, 0.4 µg/mL, 0.5 µg/mL or below.

The anti-C5 antibodies, or antigen binding fragments thereof, can be administered to a patient by any suitable means. In one embodiment, the antibodies are formulated for intravenous administration.

In one embodiment, the patient has been vaccinated with a *Neisseria* meningococcal vaccine prior to receiving the treatment methods described herein. Patients who receive treatment less than two weeks after receiving a meningococcal vaccine can receive treatment with appropriate prophylactic antibiotics until two weeks after vaccination. Vaccines against serotypes A, C, Y, W 135, and B, where available, are recommended to prevent common pathogenic meningococcal serotypes.

The efficacy of the treatment methods provided herein can be assessed using any suitable means. In one embodiment, for a patient with PLE (e.g., lymphangiectasia), the treatment produces at least one therapeutic effect selected from the group consisting of: a reduction or cessation in protein loss, edema, diarrhea, ascites, pleural effusion, pericarditis, lymphedema, abdominal pain, fatigue, weight loss and vitamin deficiency.

In another embodiment, the treatment produces a shift toward normal levels of total protein (e.g., total serum protein). For example, in one embodiment, patients treated according to the disclosed methods experience an increase in total protein serum levels to near normal levels or to within about 10% or within about 20% above or below what is considered the normal level of total protein. In another embodiment, the treatment results in at least a 1.0-fold, 1.1-fold, 1.2-fold, 1.3-fold, 1.4-fold, 1.5-fold, 1.6-fold, 1.7-fold, 1.8-fold, 1.9-fold or 2.0-fold increase in total protein serum levels from baseline within 20 days. In a particular embodiment, the treatment results in at least a 1.5-fold increase in total protein serum levels from baseline within 20 days. In another embodiment, the treatment results in at least a 1.5-fold, 1.6-fold, 1.7-fold, 1.8-fold, 1.9-fold, 2.0-fold, 2.1-fold, 2.2-fold, 2.3-fold, 2.4-fold, 2.5-fold, 2.6-fold, 2.7-fold, 2.8-fold, 2.9-fold or 3.0-fold increase in total protein serum levels from baseline within 80 days. In a particular embodiment, the treatment results in at least about a 2.3-fold (e.g., 2.26-fold) increase in total protein serum levels from baseline within 80 days.

In another embodiment, the treatment produces a shift toward normal serum albumin levels. For example, in one embodiment, patients treated according to the disclosed methods experience an increase in serum albumin levels to near normal levels or to within about 10% or within about 20% above or below what is considered the normal level of serum albumin. In another embodiment, the treatment results in at least a 1.0-fold, 1.1-fold, 1.2-fold, 1.3-fold, 1.4-fold, 1.5-fold, 1.6-fold, 1.7-fold, 1.8-fold, 1.9-fold or 2.0-fold increase in serum albumin levels from baseline within 20 days. In a particular embodiment, the treatment results in at least a 1.7-fold increase in serum albumin levels from baseline within 20 days. In another embodiment, the treatment results in at least a 2.0-fold, 2.1-fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold, 3.5-fold, 3.6-fold, 3.7-fold, 3.8-fold, 3.9-fold, 4.0-fold, 4.1-fold, 4.2-fold, 4.3-fold, 4.4-fold, 4.5-fold, 4.6-fold, 4.7-fold, 4.8-fold, 4.9-fold, 5.0-fold, 5.1-fold, 5.2-fold, 5.3-fold, 5.4-fold, 5.5-fold, 5.6-fold, 5.7-fold, 5.8-fold, 5.9-fold, 6.0-fold, 6.1-fold, 6.2-fold, 6.3-fold, 6.4-fold, 6.5-fold, 6.6-fold, 6.7-fold, 6.8-fold, 6.9-fold or 7.0-fold increase in serum albumin levels from baseline within 80 days. In another embodiment, the treatment results in at least a 5.0-fold increase in serum albumin levels from baseline within 80 days.

In another embodiment, the treatment produces a shift toward normal serum TNFR1 levels. For example, in one embodiment, patients treated according to the disclosed methods experience a decrease in serum TNFR1 levels to near normal levels or to within about 10%, or within about 20% above or below what is considered the normal level of serum TNFR1. In another embodiment, the treatment results in at least a 1.0-fold, 1.1-fold, 1.2-fold, 1.3-fold, 1.4-fold, 1.5-fold, 1.6-fold, 1.7-fold, 1.8-fold, 1.9-fold, 2.0-fold, 2.1-fold, 2.2-fold or 2.3-fold decrease in serum TNFR1 levels from baseline within 8 days. In a particular embodiment, the treatment results in at least a 1.8-fold decrease in serum TNFR1 levels from baseline within 8 days. In another embodiment, the treatment results in at least a 2.0-fold, 2.1-fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold, 3.5-fold, 3.6-fold, 3.7-fold, 3.8-fold, 3.9-fold, 4.0-fold, 4.1-fold, 4.2-fold, 4.3-fold, 4.4-fold, 4.5-fold, 4.6-fold, 4.7-fold, 4.8-fold, 4.9-fold, 5.0-fold, 5.1-fold, 5.2-fold, 5.3-fold, 5.4-fold, 5.5-fold, 5.6-fold, 5.7-fold, 5.8-fold, 5.9-fold, 6.0-fold, 6.1-fold, 6.2-fold, 6.3-fold, 6.4-fold, 6.5-fold, 6.6-fold, 6.7-fold, 6.8-fold, 6.9-fold or 7.0-fold decrease in serum TNFR1 levels from baseline within 43 days. In a particular embodiment, the treatment results in at least about a 3.3-fold (e.g., 3.25-fold) decrease in serum TNFR1 levels from baseline within 43 days.

In another embodiment, the treatment produces a shift toward normal free C5 levels. In one embodiment, the free C5 levels are decreased to below the limit of detection. In another embodiment, the free C5 levels are decreased to below the limit of detection following the first treatment dose.

In another embodiment, the treatment produces a shift toward normal membrane attack complex (MAC) deposition on white blood cells (WBCs), including granulocytes and monocytes. For example, in one embodiment, patients treated according to the methods described herein experience about a 60% reduction in MAC deposition on white bloods cells (WBCs) from baseline after 59 days. In another embodiment, the treatment results in a least about a 40%, 50%, 60%, 70% or 80% reduction in MAC deposition on white blood cells (WBCs) from baseline. In another embodiment, the treatment results in at least a 1.0-fold, 1.1-fold, 1.2-fold, 1.3-fold, 1.4-fold, 1.5-fold, 1.6-fold, 1.7-fold, 1.8-fold, 1.9-fold, 2.0-fold, 2.1-fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold, 3.5-fold, 3.6-fold, 3.7-fold, 3.8-fold, 3.9-fold, 4.0-fold, 4.1-fold, 4.2-fold, 4.3-fold, 4.4-fold, 4.5-fold, 4.6-fold, 4.7-fold, 4.8-fold, 4.9-fold, 5.0-fold, 5.1-fold, 5.2-fold, 5.3-fold, 5.4-fold, 5.5-fold, 5.6-fold, 5.7-fold, 5.8-fold, 5.9-fold, 6.0-fold, 6.1-fold, 6.2-fold, 6.3-fold, 6.4-fold, 6.5-fold, 6.6-fold, 6.7-fold, 6.8-fold, 6.9-fold or 7.0-fold decrease in MAC deposition on white blood cells (WBCs) compared to baseline.

In another embodiment, total protein levels, serum albumin levels, serum TNFR1 levels, free C5 levels, and/or MAC deposition on white blood cells (WBCs) are used to evaluate responsiveness to a therapy (e.g., an increase in total serum protein and/or serum albumin levels and/or a decrease in serum TNFR1 levels is indicative of an improvement in at least one sign of PLE (e.g., lymphangiectasia).

In another aspect, an anti-C5 antibody, or antigen binding fragment thereof, is provided, comprising CDR1, CDR2 and CDR3 domains of the heavy chain variable region having the sequence set forth in SEQ ID NO:7, and CDR1, CDR2 and CDR3 domains of the light chain variable region having the sequence set forth in SEQ ID NO:8, for administration to a patient (e.g., a patient having a PLE, such as, for example, lymphangiectasia), wherein the anti-C5 antibody, or antigen binding fragment thereof, is administered at a dose of: i) 600 mg to a patient weighing 10 kg to <20 kg twice per week during weeks 1 and 2 of the administration cycle and once during week 3, followed by 300 mg or 600 mg once per week during weeks 4 and 5 and every two weeks thereafter; ii) 600 mg to a patient weighing 20 kg to <30 kg twice per week during weeks 1 and 2 of the administration cycle, followed by 600 mg once per week during weeks 3, 4 and 5 and every two weeks thereafter; iii) 900 mg to a patient weighing 30 kg to <40 kg twice per week during weeks 1 and 2 of the administration cycle, followed by 900 mg once per week during weeks 3, 4 and 5 and every two weeks thereafter; or iv) 1200 mg to a patient weighing ≥40 kg twice per week during weeks 1 and 2 of the administration cycle, followed by 1200 mg once per week during weeks 3, 4 and 5 and every two weeks thereafter.

In one embodiment, the antibody is determined to be safe, tolerable and sufficiently non-immunogenic after multiple IV doses for use in patients with PLE (e.g., lymphangiectasia).

Further provided are kits that include a pharmaceutical composition containing an anti-C5 antibody, or antigen binding fragment thereof, such as eculizumab, and a pharmaceutically acceptable carrier, in a therapeutically effective amount adapted for use in the methods described herein. In one embodiment, the kit comprises: a) a dose of an anti-C5 antibody, or antigen binding fragment thereof, comprising CDR1, CDR2 and CDR3 domains of the heavy chain variable region having the sequence set forth in SEQ ID NO:7, and CDR1, CDR2 and CDR3 domains of the light chain variable region having the sequence set forth in SEQ ID NO:8; and b) instructions for using the anti-C5 antibody, or antigen binding fragment thereof, according to any of the methods described herein.

In another embodiment, the kit comprises a dose of an anti-C5 antibody, or antigen binding fragment thereof, wherein the anti-C5 antibody, or antigen binding fragment thereof, is administered to a patient weighing 10 kg to <20 kg at a dose of 600 mg twice per week during weeks 1 and 2 of the administration cycle and once during week 3, followed by 300 mg or 600 mg once per week during weeks 4 and 5 and every two weeks thereafter.

In another embodiment, the kit comprises a dose of an anti-C5 antibody, or antigen binding fragment thereof, wherein the anti-C5 antibody, or antigen binding fragment thereof, is administered to a patient weighing 20 kg to <30 kg at a dose of 600 mg twice per week during weeks 1 and 2 of the administration cycle, followed by 600 mg once per week during weeks 3, 4 and 5 and every two weeks thereafter.

In another embodiment, the kit comprises a dose of an anti-C5 antibody, or antigen binding fragment thereof, wherein the anti-C5 antibody, or antigen binding fragment thereof, is administered to a patient weighing 30 kg to <40 kg at a dose of 900 mg twice per week during weeks 1 and 2 of the administration cycle, followed by 900 mg once per week during weeks 3, 4 and 5 and every two weeks thereafter.

In another embodiment, the kit comprises a dose of an anti-C5 antibody, or antigen binding fragment thereof, is administered to a patient weighing ≥40 kg at a dose of 1200 mg twice per week during weeks 1 and 2 of the administration cycle, followed by 1200 mg once per week during weeks 3, 4 and 5 and every two weeks thereafter.

BRIEF DESCRIPTION OF THE DRAWINGS

FIGS. 1A-1D set forth laboratory and related parameters for "Patient A" for treatment weeks 1-5.

FIGS. 2A-2D set forth laboratory and related parameters for "Patient B" for treatment weeks 1-5.

FIGS. 7A-7H set forth laboratory and related parameters for "Patient C" for treatment weeks 1-17.

FIG. 13B depicts evidence of caviar-like villi (indicated by arrows) in the terminal ileum, and FIG. 13C shows dilated intestinal lymphatics (indicated by arrow), i.e., lymphangiectasia, in duodenal mucosa.

FIGS. 17A-L are pre- and post-treatment photographs of patients. Panels A-E illustrate resolution of acrodermatitis enteroepathica-like rash in Patient 6. Panels F-G reveal reduction in abdominal distension and panels H-J show improvement in acquired ichthyosis in Patient 3. Panels K-L depict abdominal imagine with contrast media in Patient 4 following intestinal obstruction surgery. Panel K fails to depict vast parts of the patient's intestines before eculizumab treatment, while panel L, imaged after 66 days on eculizumab, shows improvement in bowel integrity.

DETAILED DESCRIPTION

I. Definitions

Figures 3A, 3B:
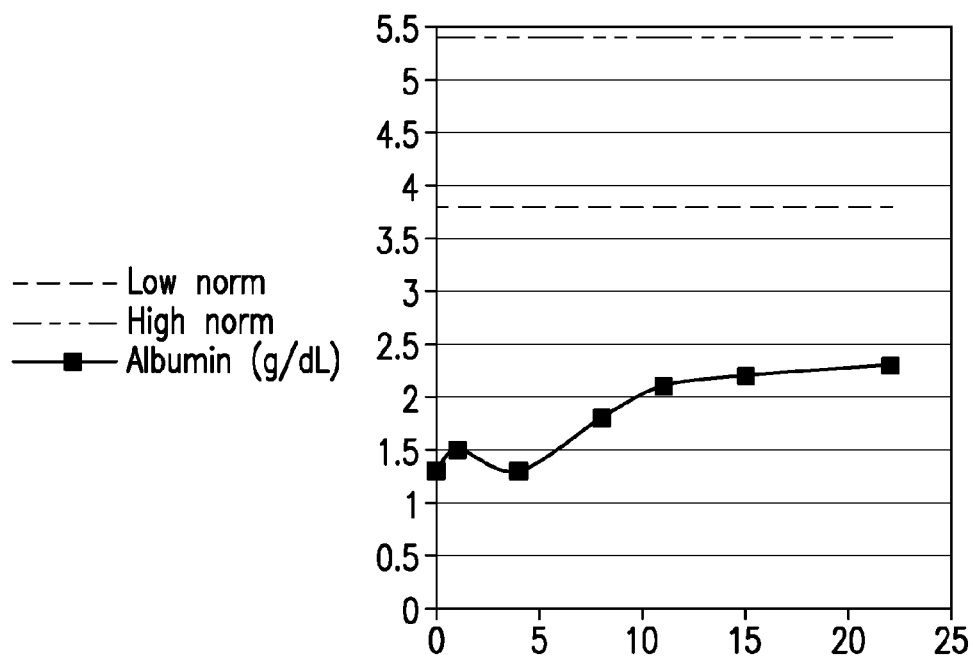
FIG. 3A is graph depicting serum albumin levels of "Patient B" (compared to low and high normal values) through treatment day 22.
FIG. 3B sets forth the raw serum albumin levels for "Patient B" (compared to low and high normal values) through treatment day 22.

As used herein, the term "subject" or "patient" is a human patient (e.g., a patient having a PLE, such as lymphangiectasia).

PLE is a condition that results from lymphatic or intestinal disruption leading to enteric protein loss, usually manifesting as peripheral edema due to hypoalbuminemia (Braamskamp, M. et al., *Eur. J. Pediatr.*, 169:1179-85, 2010). Diagnosis is often confirmed based on fecal α-1-antitrypsin clearance and symptoms can include edema, ascites, pleural effusion, pericarditis, lymphedema, diarrhea, abdominal pain, fatigue, weight loss and vitamin deficiency (Umar, S. & DiBaise, J., *Am. J. Gastroenterol.*, 105:43-9, 2010). Genetic factors may contribute to the development of PLE, including genes associated with the complement pathway. For the purposes herein, CD55 has been shown to play a role in PLE. CD55 (also knowns as decay-accelerating factor or DAF) regulates complement activity by inhibiting the formation and stability of C3/C5 convertases and accelerating their degradation (Lublin, D., *Immunohematology*, 21:39-47, 2005; Kim, D. & Song, W., *Clin. Immunol.*, 118:127-36, 2006). Inflammatory bowel disease and primary intestinal lymphangiectasia (PIL) are among the primary causes of PLE (Alexander, J. et al., *Pathophysiology*, 17:315-35, 2010).

Lymphangiectasia (also known as "intestinal lymphangiectasia," "primary intestinal lymphangiectasia" and "PIL") is a rare PLE that was first described in 1961 (Waldmann, T. et al., *Gastroenterology*, 41:197-207, 1961). Since its first documentation, fewer than 200 cases have been reported globally (Alshikho, M et al., *Am. J. Case Rep.*, 17:512-22, 2016). Due to the rarity of lymphangiectasia, its prevalence and etiology are not known. It seldom affects multiple family members and therefore does not appear to be an inherited disease. However, genetics may still play a role in disease onset, as some studies have shown changes in the regulation of genes associated with lymphangiogenesis in patients with lymphangiectasia (Hokari, R. et al., *J. Gastroenterol. Hepatol.*, 23:e88-95, 2008).

Lymphangiectasia is characterized by the dilation of vessels in the mucosa, submucosa, or subserosa of the intestines, leading to leakage of lymphatic fluid into the gastrointestinal tract. It is typically diagnosed in children, often before the age of three, and afflicts males and females equally. Patients present a range of symptoms, with edema due to protein loss being the most common. Other symptoms may include diarrhea, ascites, pleural effusion, pericarditis, lymphedema, abdominal pain, fatigue, weight loss and/or vitamin deficiency. Laboratory analyses frequently reveal hypoalbuminemia, lymphopenia and/or hypogammaglobulinemia due to the loss of lymph. Diagnosis is confirmed using endoscopy and by histopathological analysis of biopsied tissue. Additional testing may include albumin scintigraphy, ultrasound, computed tomography (CT) scans and lymphoscintigraphy (Vignes, S. & Bellanger, J., *Orphanet J. Rare Dis.*, 3:5, 2008).

There is currently no cure for lymphangiectasia and patients are treated by management of their symptoms. The most successful intervention is the implementation of a low-fat diet supplemented with medium-chain triglycerides (MCT) (Jeffries, G. et al., *N. Engl. J. Med.*, 270:761-6, 1964; Alfano, V. et al., *Nutrition*, 16:303-4, 2000). Other treatments include the administration of octreotide (experimental) or infusion with albumin (Ballinger, A. & Farthing, M.,

*Eur. J. Gastroenterol. Hepatol.,* 10:699-702, 1998). In rare cases, surgery may be required to remove afflicted tissue. Without long-term treatment, lymphangiectasia patients may suffer from severe complications from the disease, including death.

As used herein, "effective treatment" refers to treatment producing a beneficial effect, e.g., amelioration of at least one symptom of a disease or disorder. A beneficial effect can take the form of an improvement over baseline, e.g., an improvement over a measurement or observation made prior to initiation of therapy according to the method. Effective treatment may refer to alleviation of at least one symptom of a PLE, such as lymphangiectasia (e.g., protein loss, edema, diarrhea, ascites, pleural effusion, pericarditis, lymphedema, abdominal pain, fatigue, weight loss and/or vitamin deficiency).

The term "effective amount" refers to an amount of an agent that provides the desired biological, therapeutic and/or prophylactic result. That result can be reduction, amelioration, palliation, lessening, delaying and/or alleviation of one or more of the signs, symptoms, or causes of a disease, or any other desired alteration of a biological system. In one example, an "effective amount" is the amount of anti-C5 antibody, or antigen binding fragment thereof, clinically proven to alleviate at least one symptom of a PLE, such as lymphangiectasia (e.g., protein loss, edema, diarrhea, ascites, pleural effusion, pericarditis, lymphedema, abdominal pain, fatigue, weight loss and/or vitamin deficiency). An effective amount can be administered in one or more administrations.

As used herein, the terms "induction" and "induction phase" are used interchangeably and refer to the first phase of treatment.

As used herein, the terms "maintenance" and "maintenance phase" are used interchangeably and refer to the second phase of treatment. In certain embodiments, treatment is continued as long as clinical benefit is observed or until unmanageable toxicity or disease progression occurs.

As used herein, the term "serum trough level" refers to the lowest level that the agent (e.g., the anti-C5 antibody, or antigen binding fragment thereof) or medicine is present in the serum. In contrast, a "peak serum level", refers to the highest level of the agent in the serum. The "average serum level", refers to the mean level of the agent in the serum over time.

The term "antibody" describes polypeptides comprising at least one antibody-derived antigen binding site (e.g., VH/VL region or Fv, or CDR). Antibodies include known forms of antibodies. For example, the antibody can be a human antibody, a humanized antibody, a camelid antibody, a bispecific antibody, or a chimeric antibody. The antibody also can be a Fab, Fab'2, ScFv, SMIP, Affibody®, nanobody, or a domain antibody. The antibody also can be of any of the following isotypes: IgG1, IgG2, IgG3, IgG4, IgM, IgA1, IgA2, IgAsec, IgD, and IgE. The antibody can be a naturally occurring antibody or an antibody that has been altered by a protein engineering technique (e.g., by mutation, deletion, substitution, conjugation to a non-antibody moiety). For example, an antibody can include one or more variant amino acids (compared to a naturally occurring antibody) that changes a property (e.g., a functional property) of the antibody. For example, numerous such alterations are known in the art that affect, e.g., half-life, effector function, and/or immune responses to the antibody in a patient. The term antibody also includes artificial or engineered polypeptide constructs that comprise at least one antibody-derived antigen binding site.

II. Anti-C5 Antibodies

The anti-C5 antibodies described herein bind to complement component C5 (e.g., human C5) and inhibit the cleavage of C5 into fragments C5a and C5b.

Anti-C5 antibodies (or VH/VL domains derived therefrom) suitable for use in the compositions and methods described herein can be generated using methods known in the art. Alternatively, art-recognized anti-C5 antibodies can be used. Antibodies that compete with any of these art-recognized antibodies for binding to C5 also can be used.

An exemplary anti-C5 antibody is eculizumab (Soliris®). Eculizumab is a humanized monoclonal antibody (h5G1.1-mAb solution for infusion) with binding specificity uniquely specific for the human complement C5 protein. Eculizumab is described in U.S. Pat. No. 6,355,245, the entire teachings of which are hereby expressly incorporated by reference. Comprised of 1324 amino acids with a molecular mass of approximately 148 kDa, eculizumab was derived from a murine monoclonal antibody (m5G1.1-mAb) that recognizes the human complement component C5.

In other embodiments, the antibody comprises the heavy and light chain CDRs or variable regions of eculizumab. Accordingly, in one embodiment, the antibody comprises the CDR1, CDR2 and CDR3 domains of the VH region of eculizumab having the sequence set forth in SEQ ID NO:7, and the CDR1, CDR2 and CDR3 domains of the VL region of eculizumab having the sequence set forth in SEQ ID NO:8. In another embodiment, the antibody comprises heavy chain CDR1, CDR2 and CDR3 domains having the sequences set forth in SEQ ID NOs:1, 2 and 3, respectively, and light chain CDR1, CDR2 and CDR3 domains having the sequences set forth in SEQ ID NOs:4, 5 and 6, respectively. In another embodiment, the antibody comprises a VH region having the amino acid sequence set forth in SEQ ID NO:7. In another embodiment, the antibody comprises a VL region having the amino acid sequence set forth in SEQ ID NO:8. In another embodiment, the antibody comprises VH and VL regions having the amino acid sequences set forth in SEQ ID NO:7 and SEQ ID NO:8, respectively. In another embodiment, the antibody comprises the heavy chain constant region of eculizumab having the sequence set forth in SEQ ID NO:9. In another embodiment, the antibody comprises a heavy chain having the amino acid sequence set forth in SEQ ID NO:10. In another embodiment, the antibody comprises a light chain having the amino acid sequence set forth in SEQ ID NO:11. In another embodiment, the antibody comprises heavy and light chains having the amino acid sequences set forth in SEQ ID NO:10 and SEQ ID NO:11, respectively.

Another exemplary anti-C5 antibody is the 7086 antibody described in U.S. Pat. Nos. 8,241,628 and 8,883,158. In one embodiment, the antibody comprises the heavy and light chain CDRs or variable regions of the 7086 antibody (see U.S. Pat. Nos. 8,241,628 and 8,883,158). In another embodiment, the antibody, or antigen binding fragment thereof, comprises heavy chain CDR1, CDR2 and CDR3 domains having the sequences set forth in SEQ ID NOs:12, 13 and 14, respectively, and light chain CDR1, CDR2 and CDR3 domains having the sequences set forth in SEQ ID NOs:15, 16 and 17, respectively. In another embodiment, the antibody, or antigen binding fragment thereof, comprises the VH region of the 7086 antibody having the sequence set forth in SEQ ID NO:18 and the VL region of the 7086 antibody having the sequence set forth in SEQ ID NO:19.

Another exemplary anti-C5 antibody is the 8110 antibody also described in U.S. Pat. Nos. 8,241,628 and 8,883,158. In one embodiment, the antibody comprises the heavy and light chain CDRs or variable regions of the 8110 antibody. In another embodiment, the antibody, or antigen binding fragment thereof, comprises heavy chain CDR1, CDR2 and CDR3 domains having the sequences set forth in SEQ ID NOs:20, 21 and 22, respectively, and light chain CDR1, CDR2 and CDR3 domains having the sequences set forth in SEQ ID NOs:23, 24 and 25, respectively. In another embodiment, the antibody comprises the VH region of the 8110 antibody having the sequence set forth in SEQ ID NO:26, and the VL region of the 8110 antibody having the sequence set forth in SEQ ID NO:27.

Another exemplary anti-C5 antibody is the 305LO5 antibody described in US2016/0176954A1. In one embodiment, the antibody comprises the heavy and light chain CDRs or variable regions of the 305LO5 antibody. In another embodiment, the antibody, or antigen binding fragment thereof, comprises heavy chain CDR1, CDR2 and CDR3 domains having the sequences set forth in SEQ ID NOs:28, 29 and 30, respectively, and light chain CDR1, CDR2 and CDR3 domains having the sequences set forth in SEQ ID NOs:31, 32 and 33, respectively. In another embodiment, the antibody comprises the VH region of the 305LO5 antibody having the sequence set forth in SEQ ID NO:34, and the VL region of the 305LO5 antibody having the sequence set forth in SEQ ID NO:35.

The exact boundaries of CDRs have been defined differently according to different methods. In some embodiments, the positions of the CDRs or framework regions within a light or heavy chain variable domain can be as defined by Kabat et al. [(1991) "Sequences of Proteins of Immunological Interest." NIH Publication No. 91-3242, U.S. Department of Health and Human Services, Bethesda, Md.]. In such cases, the CDRs can be referred to as "Kabat CDRs" (e.g., "Kabat LCDR2" or "Kabat HCDR1"). In some embodiments, the positions of the CDRs of a light or heavy chain variable region can be as defined by Chothia et al. (*Nature*, 342:877-83, 1989). Accordingly, these regions can be referred to as "Chothia CDRs" (e.g., "Chothia LCDR2" or "Chothia HCDR3"). In some embodiments, the positions of the CDRs of the light and heavy chain variable regions can be as defined by a Kabat-Chothia combined definition. In such embodiments, these regions can be referred to as "combined Kabat-Chothia CDRs". Thomas et al. (*Mol. Immunol.*, 33:1389-1401, 1996) exemplifies the identification of CDR boundaries according to Kabat and Chothia definitions.

In one embodiment, the antibody competes for binding with, and/or binds to the same epitope on C5 as, the antibodies described herein. The term "binds to the same epitope" with reference to two or more antibodies means that the antibodies bind to the same segment of amino acid residues, as determined by a given method. Techniques for determining whether antibodies bind to the "same epitope on C5" with the antibodies described herein include, for example, epitope mapping methods, such as, for example, X-ray analyses of crystals of antigen-antibody complexes (which provides atomic resolution of the epitope) and hydrogen/deuterium exchange mass spectrometry (HDX-MS). Other methods monitor the binding of the antibody to peptide antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. Antibodies having the same VH and VL or the same CDR1, 2 and 3 sequences are expected to bind to the same epitope.

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, may be determined using known competition experiments. In certain embodiments, an antibody competes with, and inhibits binding of another antibody to a target by at least 10%, 20%, 30%, 40%, 50%, 60%, 70%, 80%, 90% or 100%. The level of inhibition or competition may be different depending on which antibody is the "blocking antibody" (i.e., the antibody that is incubated first with the target). Competing antibodies bind to the same epitope, an overlapping epitope or to adjacent epitopes (e.g., as evidenced by steric hindrance).

Methods for determining whether an antibody binds to a protein antigen and/or the affinity for an antibody to a protein antigen are known in the art. For example, the binding of an antibody to a protein antigen can be detected and/or quantified using a variety of techniques such as, but not limited to, Western blot, dot blot, surface plasmon resonance (SPR) methods (e.g., BIAcore system), or enzyme-linked immunosorbent assay (ELISA) (Benny K. C. Lo (2004) "Antibody Engineering: Methods and Protocols," Humana Press (ISBN: 1588290921); Johne, B. et al., *J. Immunol. Meth.*, 160:191-8, 1993; Jönsson, U. et al., *Ann. Biol. Clin.*, 51:19-26, 1993; Jönsson, U. et al., *Biotechniques*, 11:620-7, 1991). In addition, methods for measuring the binding affinity (e.g., dissociation and association constants) are known in the art and set forth in the working examples.

As used herein, the term "$k_a$" refers to the rate constant for association of, for example, an antibody to an antigen. The term "$k_d$" refers to the rate constant for dissociation of, for example, an antibody from the antibody/antigen complex. And the term "$K_D$" refers to the equilibrium dissociation constant of, for example, an antibody-antigen interaction. The equilibrium dissociation constant is deduced from the ratio of the kinetic rate constants, $K_D=k_d/k_a$. Such determinations can be measured, for example, at 25 C or 37 C. The kinetics of antibody binding to human C5 can be determined, for example, at pH 8.0, 7.4, 7.0, 6.5 or 6.0 via SPR on a BIAcore 3000 instrument using an anti-Fc capture method to immobilize the antibody.

In one embodiment, the anti-C5 antibody, or antigen binding fragment thereof, blocks the generation or activity of the C5a and/or C5b active fragments of a C5 protein (e.g., a human C5 protein). Through this blocking effect, the antibodies inhibit, for example, the pro-inflammatory effects of C5a and the generation of the C5b-9 MAC at the surface of a cell.

Methods for determining whether a particular antibody described herein inhibits C5 cleavage are known in the art. Inhibition of human complement component C5 can reduce the cell lysing ability of complement in a subject's body fluids. Such reductions of the cell lysing ability of complement present in the body fluid(s) can be measured by methods known in the art such as, for example, by a conventional hemolytic assay (Kabat and Mayer (eds.), "Experimental Immunochemistry, $2^{nd}$ Edition," 135-240, Springfield, Ill., CC Thomas (1961), pages 135-9), or a conventional variation of that assay such as the chicken erythrocyte hemolysis method (Hillmen, P. et al., *N. Engl. J. Med.*, 350:552, 2004). Methods for determining whether a candidate compound inhibits the cleavage of human C5 into forms C5a and C5b are known in the art (Evans, M. et al., *Mol. Immunol.*, 32:1183-95, 1995). The concentration and/or physiologic activity of C5a and C5b in a body fluid can be measured, for example, by methods known in the art. For C5b, hemolytic assays or assays for soluble C5b-9 as discussed herein can be used. Other assays known in the art can also be used. Using assays of these or other suitable types, candidate agents capable of inhibiting human complement component C5 can be screened.

Immunological techniques such as, but not limited to, ELISA can be used to measure the protein concentration of C5 and/or its split products to determine the ability of an anti-C5 antibody, or antigen binding fragment thereof, to inhibit conversion of C5 into biologically active products. In some embodiments, C5a generation is measured. In some embodiments, C5b-9 neoepitope-specific antibodies are used to detect the formation of terminal complement.

Hemolytic assays can be used to determine the inhibitory activity of an anti-C5 antibody, or antigen binding fragment thereof, on complement activation. To determine the effect of an anti-C5 antibody, or antigen binding fragment thereof, on classical complement pathway-mediated hemolysis in a serum test solution in vitro, for example, sheep erythrocytes coated with hemolysin or chicken erythrocytes sensitized with anti-chicken erythrocyte antibody are used as target cells. The percentage of lysis is normalized by considering 100% lysis equal to the lysis occurring in the absence of the inhibitor. In some embodiments, the classical complement pathway is activated by a human IgM antibody, for example, as utilized in the Wieslab® Classical Pathway Complement Kit (Wieslab® COMPL CP310, Euro-Diagnostica, Sweden). Briefly, the test serum is incubated with an anti-C5 antibody, or antigen binding fragment thereof, in the presence of a human IgM antibody. The amount of C5b-9 that is generated is measured by contacting the mixture with an enzyme conjugated anti-C5b-9 antibody and a fluorogenic substrate and measuring the absorbance at the appropriate wavelength. As a control, the test serum is incubated in the absence of the anti-C5 antibody, or antigen binding fragment thereof. In some embodiments, the test serum is a C5-deficient serum reconstituted with a C5 polypeptide.

To determine the effect of an anti-C5 antibody, or antigen binding fragment thereof, on alternative pathway-mediated hemolysis, unsensitized rabbit or guinea pig erythrocytes can be used as the target cells. In some embodiments, the serum test solution is a C5-deficient serum reconstituted with a C5 polypeptide. The percentage of lysis is normalized by considering 100% lysis equal to the lysis occurring in the absence of the inhibitor. In some embodiments, the alternative complement pathway is activated by lipopolysaccharide molecules, for example, as utilized in the Wieslab® Alternative Pathway Complement Kit (Wieslab® COMPL AP330, Euro-Diagnostica, Sweden). Briefly, the test serum is incubated with an anti-C5 antibody, or antigen binding fragment thereof, in the presence of lipopolysaccharide. The amount of C5b-9 that is generated is measured by contacting the mixture with an enzyme conjugated anti-C5b-9 antibody and a fluorogenic substrate and measuring the fluorescence at the appropriate wavelength. As a control, the test serum is incubated in the absence of the anti-C5 antibody, or antigen binding fragment thereof.

In some embodiments, C5 activity, or inhibition thereof, is quantified using a CH50eq assay. The CH50eq assay is a method for measuring the total classical complement activity in serum. This is a lytic assay that uses antibody-sensitized erythrocytes as the activator of the classical complement pathway and various dilutions of the test serum to determine the amount required to give 50% lysis (CH50). The percent hemolysis can be determined, for example, using a spectrophotometer. The CH50eq assay provides an indirect measure of terminal complement complex (TCC) formation, since the TCC themselves are directly responsible for the hemolysis that is measured. The assay is known and commonly practiced by those of skill in the art. Briefly, to activate the classical complement pathway, undiluted serum samples (e.g., reconstituted human serum samples) are added to microassay wells containing the antibody-sensitized erythrocytes to thereby generate TCC. Next, activated sera are diluted in microassay wells, which are coated with a capture reagent (e.g., an antibody that binds to one or more components of the TCC). The TCC present in the activated samples bind to the monoclonal antibodies coating the surface of the microassay wells. The wells are washed and to each well is added a detection reagent that is detectably labeled and recognizes the bound TCC. The detectable label can be, for example, a fluorescent label or an enzymatic label. The assay results are expressed in CH50 unit equivalents per milliliter (CH50 U Eq/mL).

Inhibition, e.g., as it pertains to terminal complement activity, includes at least a 5 (e.g., at least a 6, 7, 8, 9, 10, 15, 20, 25, 30, 35, 40, 45, 50, 55, or 60) % decrease in the activity of terminal complement in, e.g., a hemolytic assay or CH50eq assay as compared to the effect of a control antibody (or antigen-binding fragment thereof) under similar conditions and at an equimolar concentration. Substantial inhibition, as used herein, refers to inhibition of a given activity (e.g., terminal complement activity) of at least 40 (e.g., at least 45, 50, 55, 60, 65, 70, 75, 80, 85, 90, or 95 or greater) %.

Anti-C5 antibodies, or antigen-binding fragments thereof described herein, used in the methods described herein can be generated using a variety of art-recognized techniques. Monoclonal antibodies can be obtained by various techniques familiar to those skilled in the art. Briefly, for example, spleen cells from an animal immunized with a desired antigen are immortalized, commonly by fusion with a myeloma cell (Köhler, G. & Milstein, C., *Eur. J. Immunol.*, 6:511-9, 1976). Alternative methods of immortalization include, but are not limited to, transformation with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells can be enhanced by various techniques, including injection into the peritoneal cavity of a vertebrate host. Alternatively, one can isolate DNA sequences that encode a monoclonal antibody or a binding fragment thereof by screening a DNA library from human B cells (Huse, W. et al., *Science*, 246:1275-81, 1989).

III. Compositions

Provided herein are compositions comprising an anti-C5 antibody, or antigen binding fragment thereof. In one embodiment, the composition comprises an antibody comprising the CDR1, CDR2 and CDR3 domains of the VH region of eculizumab having the sequence set forth in SEQ ID NO:7, and the CDR1, CDR2 and CDR3 domains of the VL region of eculizumab having the sequence set forth in SEQ ID NO:8. In another embodiment, the antibody comprises heavy chain CDR1, CDR2 and CDR3 domains having the sequences set forth in SEQ ID NOs:1, 2 and 3, respectively, and light chain CDR1, CDR2 and CDR3 domains having the sequences set forth in SEQ ID NOs:4, 5 and 6, respectively. In another embodiment, the antibody comprises a VH region having the amino acid sequence set forth in SEQ ID NO:7. In another embodiment, the antibody comprises a VL region having the amino acid sequence set forth in SEQ ID NO:8. In another embodiment, the antibody comprises VH and VL regions having the amino acid sequences set forth in SEQ ID NO:7 and SEQ ID NO:8, respectively. In another embodiment, the antibody comprises a heavy chain having the amino acid sequence set forth in SEQ ID NO:10. In another embodiment, the antibody comprises a light chain having the amino acid sequence set forth in SEQ ID NO:11. In another embodiment, the antibody comprises heavy and light chains having the amino acid sequences set forth in SEQ ID NO:10 and SEQ ID NO:11, respectively.

The compositions can be formulated as a pharmaceutical solution, e.g., for administration to a subject for the treatment or prevention of PLE (e.g., lymphangiectasia). The pharmaceutical compositions can include a pharmaceutically acceptable carrier. As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt, sugars, carbohydrates, polyols and/or tonicity modifiers.

The compositions can be formulated according to standard methods (Gennaro (2000) "Remington: The Science and Practice of Pharmacy," 20$^{th}$ Edition, Lippincott, Williams & Wilkins (ISBN: 0683306472); Ansel et al. (1999) "Pharmaceutical Dosage Forms and Drug Delivery Systems," 7$^{th}$ Edition, Lippincott Williams & Wilkins Publishers (ISBN: 0683305727); and Kibbe (2000) "Handbook of Pharmaceutical Excipients American Pharmaceutical Association," 3$^{rd}$ Edition (ISBN: 091733096X)). In some embodiments, a composition can be formulated, for example, as a buffered solution at a suitable concentration and suitable for storage at 2-8 C (e.g., 4 C). In some embodiments, a composition can be formulated for storage at a temperature below 0 C (e.g., −20 C or −80 C). In some embodiments, the composition can be formulated for storage for up to 2 years (e.g., 1 month, 2 months, 3 months, 4 months, 5 months, 6 months, 7 months, 8 months, 9 months, 10 months, 11 months, 1 year, 1½ years, or 2 years) at 2-8 C (e.g., 4 C). Thus, in some embodiments, the compositions described herein are stable in storage for at least 1 year at 2-8 C (e.g., 4 C).

The pharmaceutical compositions can be in a variety of forms. These forms include, e.g., liquid, semi-solid and solid dosage forms, such as liquid solutions (e.g., injectable and infusible solutions), dispersions or suspensions, tablets, pills, powders, liposomes and suppositories. The preferred form depends, in part, on the intended mode of administration and therapeutic application. For example, compositions containing a composition intended for systemic or local delivery can be in the form of injectable or infusible solutions. Accordingly, the compositions can be formulated for administration by a parenteral mode (e.g., intravenous, subcutaneous, intraperitoneal, or intramuscular injection). "Parenteral administration," "administered parenterally," and other grammatically equivalent phrases, as used herein, refer to modes of administration other than enteral and topical administration, usually by injection, and include, without limitation, intravenous, intranasal, intraocular, pulmonary, intramuscular, intraarterial, intrathecal, intracapsular, intraorbital, intracardiac, intradermal, intrapulmonary, intraperitoneal, transtracheal, subcutaneous, subcuticular, intraarticular, subcapsular, subarachnoid, intraspinal, epidural, intracerebral, intracranial, intracarotid and intrasternal injection and infusion.

IV. Patient Populations

Provided herein are compositions and methods for treating a PLE (e.g., lymphangiectasia) in a human patient. In one embodiment, the patient has a PLE. In another embodiment, the patient has lymphangiectasia. In another embodiment, the patient has protein loss, edema, ascites, pleural effusion, pericarditis, lymphedema, diarrhea, abdominal pain, fatigue, weight loss, and/or vitamin deficiency. In one embodiment, the patient is a pediatric patient (e.g., <18 years of age). In another embodiment, a pediatric patient is <12 years of age. In another embodiment, the pediatric patient is <6 years of age. In another embodiment, the pediatric patient is <2 years of age. In another embodiment, the pediatric patient is less than 1, 2, 3, 4, 5, 6, 7, 8, 9, 10, 11, 12, 13, 14, 15, 16, 17 or 18 years of age. In another embodiment, the patient is an adult patient. In another embodiment, an adult patient is ≥18 years of age.

In one embodiment, the patient weighs 10 kg to <20 kg. In another embodiment, the patient weighs 10 kg to <30 kg. In another embodiment, the patient weighs 20 kg to <30 kg. In another embodiment, the patient weighs 30 kg to <40 kg. In another embodiment, the patient weighs≥40 kg.

In one embodiment, the patient has a mutation in a gene involved in the complement pathway (e.g., a gene involved with regulating the complement pathway). In a particular embodiment, the patient has a mutation in the CD55 gene. In another embodiment, the patient does not express CD55. In another embodiment, the patient has the CD55 variant NM_001114752.1: c.43del (p.Leu15Serfs*46). In another embodiment, the patient has red blood cell type CROM:−1 [Cr(a−)]. In another embodiment, the patient has red blood cell type CROM:−5 [Dr(a−)]. In another embodiment, the patient has red blood cell type CROM:−6 [Es(a−)]. In another embodiment, the patient has CROK-negative red blood cells. In another embodiment, the patient has the Cromer Inab (CD55-null) phenotype.

V. Outcomes

Provided herein are methods for treating a PLE (e.g., lymphangiectasia) in a patient comprising administering to the patient an anti-C5 antibody. Symptoms of PLE include, but are not limited to, protein loss, edema, ascites, pleural effusion, pericarditis, lymphedema, diarrhea, abdominal pain, fatigue, weight loss and vitamin deficiency. Patients treated according to the methods disclosed herein experience improvement in at least one symptom of PLE. For example, the treatment may produce at least one therapeutic effect selected from the group consisting of a reduction or cessation in protein loss, edema, ascites, pleural effusion, pericarditis, lymphedema, diarrhea, abdominal pain, fatigue, weight loss or vitamin deficiency.

In another embodiment, the treatment produces a shift toward normal levels of total protein (e.g., total serum protein). For example, in on embodiment, patients treated according to the disclosed methods experience an increase in total protein serum levels to near normal levels or to within about 10% or within about 20% above or below what is considered the normal level of total protein. In another embodiment, the treatment results in at least a 1.0-fold, 1.1-fold, 1.2-fold, 1.3-fold, 1.4-fold, 1.5-fold, 1.6-fold, 1.7-fold, 1.8-fold, 1.9-fold or 2.0-fold increase in total protein serum levels from baseline within 20 days. In a particular embodiment, the treatment results in at least a 1.5-fold increase in total protein serum levels from baseline within 20 days. In another embodiment, the treatment results in at least a 1.5-fold, 1.6-fold, 1.7-fold, 1.8-fold, 1.9-fold, 2.0-fold, 2.1-fold, 2.2-fold, 2.3-fold, 2.4-fold, 2.5-fold, 2.6-fold, 2.7-fold, 2.8-fold, 2.9-fold, or 3.0-fold increase in total protein serum levels from baseline within 80 days. In a particular embodiment, the treatment results in at least a 2.3-fold (e.g., 2.26-fold) increase in total protein serum levels from baseline within 80 days.

In another embodiment, the treatment produces a shift toward normal serum albumin levels. For example, in on embodiment, patients treated according to the disclosed methods experience an increase in serum albumin levels to near normal levels or to within about 10% or within about 20% above or below what is considered the normal level of serum albumin. In another embodiment, the treatment results in at least a 1.0-fold, 1.1-fold, 1.2-fold, 1.3-fold, 1.4-fold, 1.5-fold, 1.6-fold, 1.7-fold, 1.8-fold, 1.9-fold or 2.0-fold increase in serum albumin levels from baseline within 20 days. In a particular embodiment, the treatment results in at least a 1.7-fold increase in serum albumin levels from baseline within 20 days. In another embodiment, the treatment results in at least a 2.0-fold, 2.1-fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold, 3.5-fold, 3.6-fold, 3.7-fold, 3.8-fold, 3.9-fold, 4.0-fold, 4.1-fold, 4.2-fold, 4.3-fold, 4.4-fold, 4.5-fold, 4.6-fold, 4.7-fold, 4.8-fold, 4.9-fold, 5.0-fold, 5.1-fold, 5.2-fold, 5.3-fold, 5.4-fold, 5.5-fold, 5.6-fold, 5.7-fold, 5.8-fold, 5.9-fold, 6.0-fold, 6.1-fold, 6.2-fold, 6.3-fold, 6.4-fold, 6.5-fold, 6.6-fold, 6.7-fold, 6.8-fold, 6.9-fold or 7.0-fold increase in serum albumin levels from baseline within 80 days. In another embodiment, the treatment results in at least a 5-fold increase in serum albumin levels from baseline within 80 days.

In another embodiment, the treatment produces a shift toward normal serum TNFR1 levels. For example, in on embodiment, patients treated according to the disclosed methods experience a decrease in serum TNFR1 levels to near normal levels or to within 10%, or within 20% above or below what is considered the normal level of serum TNFR1. In another embodiment, the treatment results in at least a 1.0-fold, 1.1-fold, 1.2-fold, 1.3-fold, 1.4-fold, 1.5-fold, 1.6-fold, 1.7-fold, 1.8-fold, 1.9-fold or 2.0-fold, 2.1-fold, 2.2-fold or 2.3-fold decrease in serum TNFR1 levels from baseline within 8 days. In a particular embodiment, the treatment results in at least a 1.8-fold decrease in serum TNFR1 levels from baseline within 8 days. In another embodiment, the treatment results in at least a 2.0-fold, 2.1-fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold, 3.5-fold, 3.6-fold, 3.7-fold, 3.8-fold, 3.9-fold, 4.0-fold, 4.1-fold, 4.2-fold, 4.3-fold, 4.4-fold, 4.5-fold, 4.6-fold, 4.7-fold, 4.8-fold, 4.9-fold, 5.0-fold, 5.1-fold, 5.2-fold, 5.3-fold, 5.4-fold, 5.5-fold, 5.6-fold, 5.7-fold, 5.8-fold, 5.9-fold, 6.0-fold, 6.1-fold, 6.2-fold, 6.3-fold, 6.4-fold, 6.5-fold, 6.6-fold, 6.7-fold, 6.8-fold, 6.9-fold or 7.0-fold decrease in serum TNFR1 levels from baseline within 43 days. In a particular embodiment, the treatment results in at least a 3.3-fold (e.g., 3.25-fold) decrease in serum TNFR1 levels from baseline within 43 days.

In another embodiment, the treatment produces a shift toward normal free C5 levels. In one embodiment, the free C5 levels are decreased to below the limit of detection. In another embodiment, the free C5 levels are decreased to below the limit of detection following the first treatment dose.

In another embodiment, the treatment produces a shift toward normal MAC deposition on WBCs, including granulocytes and WBCs. For example, in one embodiment, patients treated according to the methods disclosed herein experience about a 60% reduction in MAC deposition on WBCs from baseline after 59 days. In another embodiment, the treatment results in a least a 40%, 50%, 60%, 70% or 80% reduction in MAC deposition on WBCs from baseline. In another embodiment, the treatment results in at least a 1.0-fold, 1.1-fold, 1.2-fold, 1.3-fold, 1.4-fold, 1.5-fold, 1.6-fold, 1.7-fold, 1.8-fold, 1.9-fold, 2.0-fold, 2.1-fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold, 3.5-fold, 3.6-fold, 3.7-fold, 3.8-fold, 3.9-fold, 4.0-fold, 4.1-fold, 4.2-fold, 4.3-fold, 4.4-fold, 4.5-fold, 4.6-fold, 4.7-fold, 4.8-fold, 4.9-fold, 5.0-fold, 5.1-fold, 5.2-fold, 5.3-fold, 5.4-fold, 5.5-fold, 5.6-fold, 5.7-fold, 5.8-fold, 5.9-fold, 6.0-fold, 6.1-fold, 6.2-fold, 6.3-fold, 6.4-fold, 6.5-fold, 6.6-fold, 6.7-fold, 6.8-fold, 6.9-fold or 7.0-fold decrease in MAC deposition on WBCs compared to baseline.

In another embodiment, total protein levels, serum albumin levels, serum TNFR1 levels, free C5 levels, and/or MAC deposition on WBCs are used to evaluate responsiveness to a therapy (e.g., an increase in total serum protein and/or serum albumin levels and/or a decrease in serum TNFR1 levels is indicative of an improvement in at least one sign of a PLE (e.g., lymphangiectasia).

VI. Kits and Unit Dosage Forms

Also provided herein are kits which include a pharmaceutical composition containing an anti-C5 antibody, or antigen binding fragment thereof, such as eculizumab, and a pharmaceutically-acceptable carrier, in a therapeutically effective amount adapted for use in the preceding methods. The kits optionally also can include instructions, e.g., comprising administration schedules, to allow a practitioner (e.g., a physician, nurse or patient) to administer the composition contained therein to administer the composition to a patient having a PLE (e.g., lymphangiectasia). The kit also can include a syringe.

Optionally, the kits include multiple packages of the single-dose pharmaceutical compositions each containing an effective amount of the anti-C5 antibody, or antigen binding fragment thereof (e.g., eculizumab), for a single administration in accordance with the methods provided herein. Instruments or devices necessary for administering the pharmaceutical composition(s) also may be included in the kits. A kit can provide one or more pre-filled syringes containing an amount of the anti-C5 antibody, or antigen binding fragment thereof.

In one embodiment, the present invention provides a kit for treating a PLE (e.g., lymphangiectasia) in a human patient, the kit comprising: a) a dose of an anti-C5 antibody, or antigen binding fragment thereof, comprising CDR1, CDR2 and CDR3 domains of the heavy chain variable region having the sequence set forth in SEQ ID NO:7, and CDR1, CDR2 and CDR3 domains of the light chain variable region having the sequence set forth in SEQ ID NO:8; and b) instructions for using the anti-C5 antibody, or antigen binding fragment thereof, according to any of the methods described herein.

In another embodiment, the kit comprises a dose of an anti-C5 antibody, or antigen binding fragment thereof, wherein the anti-C5 antibody, or antigen binding fragment thereof, is administered to a patient weighing 10 to <20 kg at a dose of 600 mg twice per week during weeks 1 and 2 of the administration cycle and once during week 3, followed by 300 mg or 600 mg once per week during weeks 4 and 5 and every two weeks thereafter.

In another embodiment, the kit comprises a dose of an anti-C5 antibody, or antigen binding fragment thereof, wherein the anti-C5 antibody, or antigen binding fragment thereof, is administered to a patient weighing 20 kg to <30 kg at a dose of 600 mg twice per week during weeks 1 and 2 of the administration cycle, followed by 600 mg once per week during weeks 3, 4 and 5 and every two weeks thereafter.

In another embodiment, the kit comprises a dose of an anti-C5 antibody, or antigen binding fragment thereof, wherein the anti-C5 antibody, or antigen binding fragment thereof, is administered to a patient weighing 30 to <40 kg at a dose of 900 mg twice per week during weeks 1 and 2 of the administration cycle, followed by 900 mg once per week during weeks 3, 4 and 5 and every two weeks thereafter.

In another embodiment, the kit comprises a dose of an anti-C5 antibody, or antigen binding fragment thereof, is administered to a patient weighing ≥40 kg at a dose of 1200 mg twice per week during weeks 1 and 2 of the administration cycle, followed by 1200 mg once per week during weeks 3, 4 and 5 and every two weeks thereafter.

The following examples are merely illustrative and should not be construed as limiting the scope of this disclosure in any way as many variations and equivalents will become apparent to those skilled in the art upon reading the present disclosure. The contents of all references, Genbank entries, patents and published patent applications cited throughout this application are expressly incorporated herein by reference in their entireties.

EXAMPLES

Example 1: Overview of Study

A clinical study is conducted to explore the safety, tolerability and efficacy of eculizumab in pediatric patients with lymphangiectasia.

1. Dosing and Schedule of Assessments

Eculizumab for the treatment of aHUS is administered intravenously according to the dosing schedule set forth below in Table 1. The schedule of dosing and assessments is set forth below in Tables 2-5.

TABLE 1

Standard aHUS Dosing for patients <18 years of age

| Body weight | Induction phase | Maintenance phase |
|---|---|---|
| >40 kg | 900 mg weeklyX4 doses | 1200 mg at week 5; then 1200 mg every 2 weeks |
| 30-40 kg | 600 mg weeklyX2 doses | 900 mg at week 3; then 900 mg every 2 weeks |
| 20-30 kg | 600 mg weeklyX2 doses | 600 mg at week 3; then 600 mg every 2 weeks |
| 10-20 kg | 600 mg weeklyX1 doses | 300 mg at week 2; then 300 mg every 2 weeks |
| 5-10 kg | 300 mg weeklyX1 doses | 300 mg at week 2; then 300 mg every 3 weeks |

TABLE 2

Schedule of Dosing and Assessments for Patient Between 10 and <20 kg*

| | Prior to 1st Dose | 1 | 2 3 | 4 | 5 | 8 | 11 | 15 | 22 | 29 | 43 | 57 | 71 |
|---|---|---|---|---|---|---|---|---|---|---|---|---|---|
| | | | | | | | | Treatment Days / Weeks | | | | | |
| | | 1 | | 2 | | | | 3 | 4 | 5 | 7 | 9 | 11 |
| dd/mm/yy N. meningitides: vaccination and antibiotics[1] | X | | | | | | | | | | | | |
| Dosing eculizumab[2] | | 600 | | 600 | | 600 | 600 | 600 | 300 or 600 | 300 or 600 | 300 or 600 | 300 or 600 | 300 or 600 |
| PK and PD analysis[3] Two 2 mL tubes for pediatric patients | | Baseline & Peak | | Trough & Peak | | Trough & Peak | Trough & Peak | Trough & Peak | Trough & Peak | Trough & Peak | Trough & Peak | Trough & Peak | Trough & Peak |
| Clinical Lab (Hema, Chem. & UA) Tests[4] | | X | | X | | X | | X | X | X | X | X | X |
| Hemolytic Markers[5] | | X | | X | | X | | X | X | X | | X | |
| Prothrombotic Measures[6] | | X | | X | | X | | X | X | X | | X | |

TABLE 2-continued

Schedule of Dosing and Assessments for Patient Between 10 and <20 kg*

| | Prior to 1st Dose | 1 | 2 | 3 | 4 | 5 | 8 | 11 | 15 Weeks | 22 | 29 | 43 | 57 | 71 |
|---|---|---|---|---|---|---|---|---|---|---|---|---|---|---|
| | | 1 | | | | | 2 | | 3 | 4 | 5 | 7 | 9 | 11 |
| Pro-inflammatory Markers[7] | | X | | | X | | X | | X | X | X | | X | |
| Complement Markers[8] | | X | | | X | | X | | X | X | X | | X | |
| Systolic and Diastolic Blood Pressure | | X | | | X | | X | | X | X | X | X | X | X |
| Thrombo-embolic events[9] | | X | | | X | | X | | X | X | X | X | X | X |
| Assessment of outcomes such as stool volume, serum albumin and immuno-globulin levels, etc | colspan | | | | | - - - To be recorded and reported throughout - - - | | | | | | | | |
| Serious & non serious Adverse Events (AEs & SAEs)[10] | | | | | | - - - To be recorded and reported throughout - - - | | | | | | | | |
| Concomitant Medications | | | | | | - - - To be recorded throughout - - - | | | | | | | | |

TABLE 3

Schedule of Dosing and Assessments for Patient Between 20 and <30 kg*

| | Prior to 1st Dose | 1 | 2 | 3 | 4 | 5 | 8 | 11 | 15 Weeks | 22 | 29 | 43 | 57 | 71 |
|---|---|---|---|---|---|---|---|---|---|---|---|---|---|---|
| | | 1 | | | | | 2 | | 3 | 4 | 5 | 7 | 9 | 11 |
| dd/mm/yy N. meningitides: vaccination and antibiotics[1] | X | | | | | | | | | | | | | |
| Dosing eculizumab[2] | | 600 | | | 600 | | 600 | 600 | 600 | 600 | 600 | 600 | 600 | 600 |
| PK and PD analysis[3] Two 2 mL tubes for pediatric patients | | Baseline & Peak | | | Trough & Peak | | Trough & Peak | Trough & Peak | Trough & Peak | Trough & Peak | Trough & Peak | Trough & Peak | Trough & Peak | Trough & Peak |
| Clinical Lab (Hema, Chem. & UA) Tests[4] | | X | | | X | | X | | X | X | X | X | X | X |
| Hemolytic Markers[5] | | X | | | X | | X | | X | X | X | | X | |
| Prothrombotic Measures[6] | | X | | | X | | X | | X | X | X | | X | |
| Pro-inflammatory Markers[7] | | X | | | X | | X | | X | X | X | | X | |
| Complement Markers[8] | | X | | | X | | X | | X | X | X | | X | |

TABLE 3-continued

Schedule of Dosing and Assessments for Patient Between 20 and <30 kg*

| | Prior to 1st Dose | Treatment Days | | | | | | | | | | | |
|---|---|---|---|---|---|---|---|---|---|---|---|---|---|
| | | 1 | 2 3 | 4 | 5 | 8 | 11 | 15 | 22 | 29 | 43 | 57 | 71 |
| | | | | | | | | Weeks | | | | | |
| | | 1 | | | | 2 | | 3 | 4 | 5 | 7 | 9 | 11 |
| Systolic and Diastolic Blood Pressure | | X | | X | | X | | X | X | X | X | X | X |
| Thrombo-embolic events[9] | | X | | X | | X | | X | X | X | X | X | X |
| Assessment of outcomes such as stool volume, serum albumin and immuno-globulin levels, etc | | - - - To be recorded and reported throughout - - - | | | | | | | | | | | |
| Serious & non serious Adverse Events (AEs & SAEs)[10] | | - - - To be recorded and reported throughout - - - | | | | | | | | | | | |
| Concomitant Medications | | - - - To be recorded throughout - - - | | | | | | | | | | | |

TABLE 4

Schedule of Dosing and Assessments for Patient Between 30 and <40 kg*

| | Prior to 1st Dose | Treatment Days | | | | | | | | | | | |
|---|---|---|---|---|---|---|---|---|---|---|---|---|---|
| | | 1 | 2 3 | 4 | 5 | 8 | 11 | 15 | 22 | 29 | 43 | 57 | 71 |
| | | | | | | | | Weeks | | | | | |
| | | 1 | | | | 2 | | 3 | 4 | 5 | 7 | 9 | 11 |
| dd/mm/yy N. meningitides: vaccination and antibiotics[1] | X | | | | | | | | | | | | |
| Dosing eculizumab [2] | | 900 | | 900 | | 900 | | 900 | 900 | 900 | 900 | 900 | 900 |
| PK and PD analysis[3] Two 2 mL tubes for pediatric patients | | Baseline & Peak | | Trough & Peak | | Trough & Peak | | Trough & Peak | Trough & Peak | Trough & Peak | Trough & Peak | Trough & Peak | Trough & Peak |
| Clinical Lab (Hema, Chem. & UA) Tests[4] | | X | | X | | X | | X | X | X | X | X | X |
| Hemolytic Markers[5] | | X | | X | | X | | X | X | X | | X | |
| Prothrombotic Measures[6] | | X | | X | | X | | X | X | X | | X | |
| Pro-inflammatory Markers[7] | | X | | X | | X | | X | X | X | | X | |
| Complement Markers[8] | | X | | X | | X | | X | X | X | | X | |
| Systolic and Diastolic Blood Pressure | | X | | X | | X | | X | X | X | X | X | X |
| Thrombo-embolic events[9] | | X | | X | | X | | X | X | X | X | X | X |

TABLE 4-continued

Schedule of Dosing and Assessments for Patient Between 30 and <40 kg*

| | Prior to 1st | 1 | 2 | 3 | 4 | 5 | 8 | 11 | Treatment Days 15 Weeks | 22 | 29 | 43 | 57 | 71 |
|---|---|---|---|---|---|---|---|---|---|---|---|---|---|---|
| | Dose | 1 | | | | | 2 | | 3 | 4 | 5 | 7 | 9 | 11 |
| Assessment of outcomes such as stool volume, serum albumin and immuno-globulin levels, etc | X | X | | | | | - - - To be recorded and reported throughout - - - | | | | | | | |
| Serious & non serious Adverse Events (AEs & SAEs)[10] | | | | | | | - - - To be recorded and reported throughout - - - | | | | | | | |
| Concomitant Medications | | | | | | | - - - To be recorded throughout - - - | | | | | | | |

TABLE 5

Schedule of Dosing and Assessments for Patient ≥40 kg*

| | Prior to 1st | 1 | 2 | 3 | 4 | 5 | 8 | 11 | Treatment Days 15 Weeks | 22 | 29 | 43 | 57 | 71 |
|---|---|---|---|---|---|---|---|---|---|---|---|---|---|---|
| | Dose | 1 | | | | | 2 | | 3 | 4 | 5 | 7 | 9 | 11 |
| dd/mm/yy N. meningitides: vaccination and antibiotics[1] | X | | | | | | | | | | | | | |
| Dosing eculizumab[2] | | 1200 | | | | | 1200 | | 1200 | 1200 | 1200 | 1200 | 1200 | 1200 |
| PK and PD analysis[3] Two 2 mL tubes for pediatric patients | | Baseline & Peak | | | | | Trough & Peak | | Trough & Peak | Trough & Peak | Trough & Peak | Trough & Peak | Trough & Peak | Trough & Peak |
| Clinical Lab (Hema, Chem. & UA) Tests[4] | X | X | | | X | | X | | X | X | X | X | X | X |
| Hemolytic Markers[5] | X | X | | | X | | X | | X | X | X | | X | |
| Prothrombotic Measures[6] | X | X | | | X | | X | | X | X | X | | X | |
| Pro-inflammatory Markers[7] | X | X | | | X | | X | | X | X | X | | X | |
| Complement Markers[8] | X | X | | | X | | X | | X | X | X | | X | |
| Systolic and Diastolic Blood Pressure | X | X | | | X | | X | | X | X | X | X | X | X |
| Thrombo-embolic events[9] | X | X | | | X | | X | | X | X | X | X | X | X |
| Assessment of outcomes such as stool volume, serum albumin and immuno-globulin levels, etc | | | | | | | - - - To be recorded and reported throughout - - - | | | | | | | |

TABLE 5-continued

Schedule of Dosing and Assessments for Patient ≥40 kg*

| | Prior to 1st Dose | Treatment Days | | | | | | | | | | | |
|---|---|---|---|---|---|---|---|---|---|---|---|---|---|
| | | 1 | 2 3 | 4 | 5 | 8 | 11 | 15 | 22 | 29 | 43 | 57 | 71 |
| | | | | | | | | Weeks | | | | | |
| | | 1 | | | | 2 | | 3 | 4 | 5 | 7 | 9 | 11 |
| Serious & non serious Adverse Events (AEs & SAEs)[10] | | - - - To be recorded and reported throughout - - - | | | | | | | | | | | |
| Concomitant Medications | | - - - To be recorded throughout - - - | | | | | | | | | | | |

Footnotes to Tables 2, 3, 4 and 5

* Blood volumes drawn do not exceed recommendations for pediatric patients. For patients <2.7 kg, the maximum amounts of blood drawn are 0.8 mL at one time and 2.4 mL during one month. For patients 2.7-3.6 kg, the maximum amounts of blood drawn are 2.5 mL at one time and 23 mL during one month. For patients 3.6-4.5 kg, the maximum amounts of blood drawn are 3.5 mL at one time and 30 mL during one month. For patients 4.5-6.8 kg, the maximum amounts of blood drawn are 5 mL at one time and 40 mL during one month. For patients 7.3-18.2 kg, the maximum amounts of blood drawn are 10 mL at one time and 60-130 mL during one month. For patients 18.6-27.3 kg, the maximum amounts of blood drawn are 20 mL at one time and 140-200 mL during one month. For patients 27.7-29.5 kg, the maximum amounts of blood drawn are 25 mL at one time and 220 mL during one month. For patients 30.0-45.5 kg, the maximum amounts of blood drawn are 30 mL at one time and 240-350 mL during one month.

[1] Meningococcal infection: To reduce the risk of meningococcal infection, all patients are vaccinated at least 2 weeks prior to receiving Soliris® (eculizumab) and are re-vaccinated according to current medical guidelines for vaccination use. Tetravalent vaccines against serotypes A, C, Y and W135 and vaccination against serotype B (where available) are used, preferably conjugated ones. Vaccination may not be sufficient to prevent meningococcal infection. Consideration is given to official guidance on the appropriate use of antibacterial agents. If after assessment of the benefit risk balance the physician decides to start eculizumab therapy before 14 days, the physician gives careful consideration in the choice of prophylaxis method against *Neisseria* infection proposed to the patient until complete immunization (i.e., 14 days).

[2] The treatment schedule is as follows:
Day 1=First day of dosing.
Patients 10 kg to <20 kg or 20 kg to <30 kg receive 600 mg doses on days 1, 4, 8, 11 and 15, followed by 300 mg or 600 mg doses given either weekly or biweekly, beginning on day 22 for weight 10 kg to <20 kg, and 600 mg doses either weekly or biweekly, beginning day 22 for weight 20 kg to <30 kg.
Patients 30 kg to <40 kg receive 900 mg doses on days 1, 4, 8, 11 and 15, followed by 900 mg doses given either weekly or biweekly, beginning on day 22.
Patients≥40 kg receive 1200 mg doses on days 1, 4, 8, 11 and 15, followed by 1200 mg doses given either weekly or biweekly, beginning on day 22.

The dosing regimen is To Be Determined based on weight and clinical/laboratory assessments, in particular after Weeks 1 and 2.

[3] Baseline and trough serum samples for PK and PD (free C5 levels) testing are taken 5-90 minutes before eculizumab infusion. Peak samples for PK and PD (free C5 levels) testing are taken 60 minutes after the completion of eculizumab infusion.

[4] Suggested lab parameters: hemoglobin (Hb), hematocrit (HCT), platelet count, WBC count, creatinine, BUN, serum albumin, and serum immunoglobulins. Samples for laboratory tests are collected 5 to 90 minutes prior to administration of eculizumab.

[5] Suggested hemolytic markers: serum lactose dehydrogenase (LDH), plasma haptoglobin, and reticulocytes and schistocytes (blood smear). Blood samples for hemolytic markers are collected 5 to 90 minutes prior to administration of eculizumab.

[6] Suggested prothrombotic markers: plasma fibrinogen, serum fibrin split products, and plasma D-dimer. Blood samples for prothrombotic markers are collected 5 to 90 minutes prior to administration of eculizumab.

[7] Suggested pro-inflammatory markers: soluble TNFR1 (sTNFR1) and C-reactive protein (CRP). Blood samples for pro-inflammatory markers are collected 5 to 90 minutes prior to administration of eculizumab.

[8] Suggested serum complement marker: C3. Blood samples for complement marker are collected 5 to 90 minutes prior to administration of eculizumab.

[9] Suggested information on any clinical thromboembolic events including date, location and method of diagnosis.

[10] Adverse Reactions and Serious Adverse Reactions are documented in patient's chart.

2. Preparation and Administration of Eculizumab

Each vial of 30 mL contains 300 mg of eculizumab (10 mg/mL) for infusion. The solution is a clear, colorless, pH 7.0 solution. The product contains 5.00 mmol sodium per dose (1 vial), which should be taken into consideration by patients on a controlled sodium diet.

Reconstitution and dilution is performed in accordance with good practices rules, particularly for the respect of asepsis. The total amount of eculizumab is withdrawn from the vial(s) using a sterile syringe. The recommended dose is transferred to an infusion bag. Eculizumab is diluted to a final concentration of 5 mg/mL by addition to the infusion bag using 0.9% sodium chloride, 0.45% sodium chloride or 5% Dextrose in water. The final volume of a 5 mg/mL diluted solution is 120 mL for 600 mg doses, 180 mL for 900 mg doses, or 240 mL for 1200 mg doses, as set forth in Table 6.

TABLE 6

Eculizumab Reconstitution

| Eculizumab dose | Number of Eculizumab vials (10 mg/mL) | Volume of Eculizumab concentrate (10 mg/mL) | Volume of diluent: 0.9% NaCl Or 0.45% NaCl Or 5% dextrose in water | Total volume of administration (5 mg/mL) |
|---|---|---|---|---|
| n × 300 mg General Rule | n vials | n × 30 mL | n × 30 mL | 2n × 30 mL |
| 300 mg | 1 vial | 30 mL | 30 mL | 60 mL |
| 600 mg | 2 vials | 60 mL | 60 mL | 120 mL |
| 900 mg | 3 vials | 90 mL | 90 mL | 180 mL |
| 1200 mg | 4 vials | 120 mL | 120 mL | 240 mL |

The infusion bag containing the diluted solution is gently agitated to ensure thorough mixing of the product and diluents. The diluted solution is allowed to warm to room temperature prior to administration by exposure to ambient air. Any unused portion left in a vial is discarded, as the product contains no preservatives. Any unused medicinal product or waste material is disposed of in accordance with local requirements.

After dilution, the final concentration of the solution to be infused is 5 mg/mL. After dilution, the medicinal product should be used immediately. Chemical and physical stability has, however, been demonstrated for 24 hours at 2-8 C. Prior to administration, the eculizumab solution is visually inspected for particulate matter and discolouration.

Eculizumab is administered only via intravenous infusion. Eculizumab is not administered as an intravenous push or bolus injection. The diluted solution of eculizumab is administered by intravenous infusion over 1 to 4 hours via gravity feed, a syringe-type pump, or an infusion pump. It is not necessary to protect the diluted solution of eculizumab from light during administration to the patient.

Patients are monitored for one hour following infusion. If an adverse event occurs during the administration of eculizumab, the infusion is slowed or stopped at the discretion of the physician. If the infusion is slowed, the total infusion time may not exceed two hours.

As with all therapeutic proteins, administration of eculizumab may result in infusion reactions or immunogenicity that could cause allergic or hypersensitivity reactions (including anaphylaxis), although immune system disorders within 48 hours of eculizumab administration did not differ from placebo treatment in PNH and non-PNH studies conducted with eculizumab. In clinical trials, no PNH patients experienced an infusion reaction that required discontinuation of eculizumab. Eculizumab administration is interrupted in all patients experiencing severe infusion reactions and appropriate medical therapy administered.

1. Vaccination

Due to its mechanism of action, the use of Soliris® (eculizumab) increases the patient's susceptibility to meningococcal infection (*Neisseria meningitidis*). These patients might be at risk of disease by uncommon serogroups (such as X), although meningococcal disease due to any serogroup may occur. To reduce the risk of infection, all patients are vaccinated at least two weeks prior to receiving Soliris® (eculizumab) unless the risk of delaying Soliris® (eculizumab) therapy outweighs the risks of developing a meningococcal infection. Patients who are treated with Soliris® (eculizumab) less than two weeks after receiving a meningococcal vaccine receive treatment with appropriate prophylactic antibiotics until two weeks after vaccination. Vaccines against serotypes A, C, Y, W135 and B, where available, are recommended in preventing the commonly pathogenic meningococcal serotypes. Patients are vaccinated or revaccinated according to current national vaccination guidelines for vaccination use.

All patients are monitored for early signs of meningococcal infection, evaluated immediately if infection is suspected, and treated with antibiotics if necessary. Patients are informed of these signs and symptoms and steps taken to seek medical care immediately. Vaccination may not be sufficient to prevent meningococcal infection. Consideration should be given to official guidance on the appropriate use of antibacterial agents.

2. Complications

One complication includes increased susceptibility to infections with encapsulated bacteria. Accordingly, pneumococcal and meningococcal vaccination is verified prior to treatment. Alternatively, prophylactic Moxypen treatment is provided until vaccination and up to two weeks after vaccination. Patients receiving prophylactic Moxypen treatment are guided to consult a doctor if fever accompanied by headaches, vomiting, myalgia and photophobia arises. Prophylactic antibiotics can be given throughout the entire treatment.

An adverse reaction is a response that is noxious and unintended and occurs at doses normally used in human for the prophylaxis, diagnosis or therapy of disease or for restoration, correction or modification of physiological function or resulting from a misuse of the drug or product.

A serious adverse reaction is an adverse reaction that results in death or is life-threatening, results in persistent or significant disability or incapacity, requires inpatient hospitalization or prolongation of existing hospitalization or is a congenital anomaly/birth defect. Important medical events that may not result in death, be life-threatening, or require hospitalization may be considered a serious adverse reaction when, based upon appropriate medical judgment, they may jeopardize the patient and may require medical or surgical intervention to prevent one of the outcomes listed in this definition.

3. Long Term Follow-Up Recommendations

On each hospitalization for eculizumab treatment, vital signs are taken (including blood pressure, pulse, weight and height). Every two weeks, blood is drawn for CBC and differential, full chemistry (including kidney and liver function, electrolytes, blood proteins and lipids, and LDH, CRP). Once a month, blood is drawn for immunoglobulins, complement levels and vitamins A, D and E.

Example 2: Preliminary Results from Clinical Study in Pediatric Lymphangiectasia Patients The following is a summary of preliminary data from three patients in an ongoing study conducted substantially according to the protocol described above in Example 1.

Figure 5:
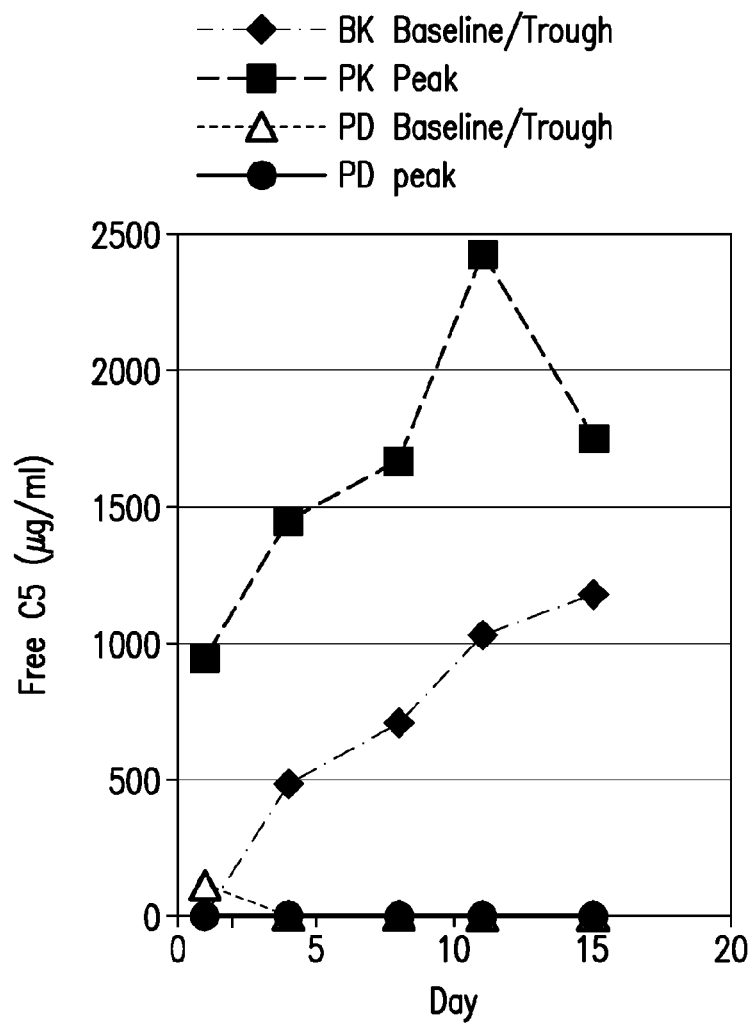
FIG. 5 is a graph depicting the pharmacokinetic (PK) and pharmacodynamic (PD) baseline/troughs in free C5 µg/mL and peaks for "Patient B" through treatment day 15.
Figures 6A, 6B:
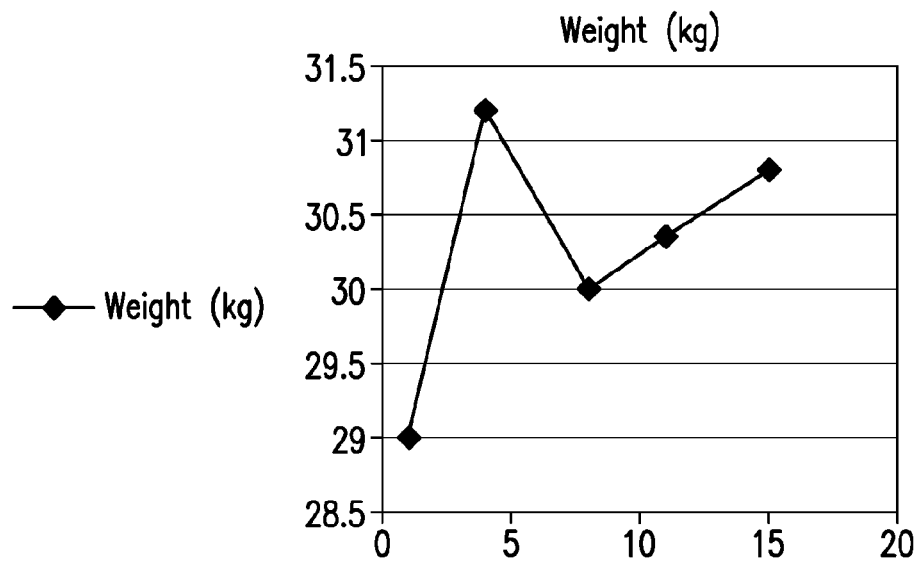
FIG. 6A is a graph depicting the weight of "Patient B" through treatment day 15.
FIG. 6B sets forth the actual weight of "Patient B" on treatment days 1, 4, 8, 11 and 15.
Figures 10A, 10B:
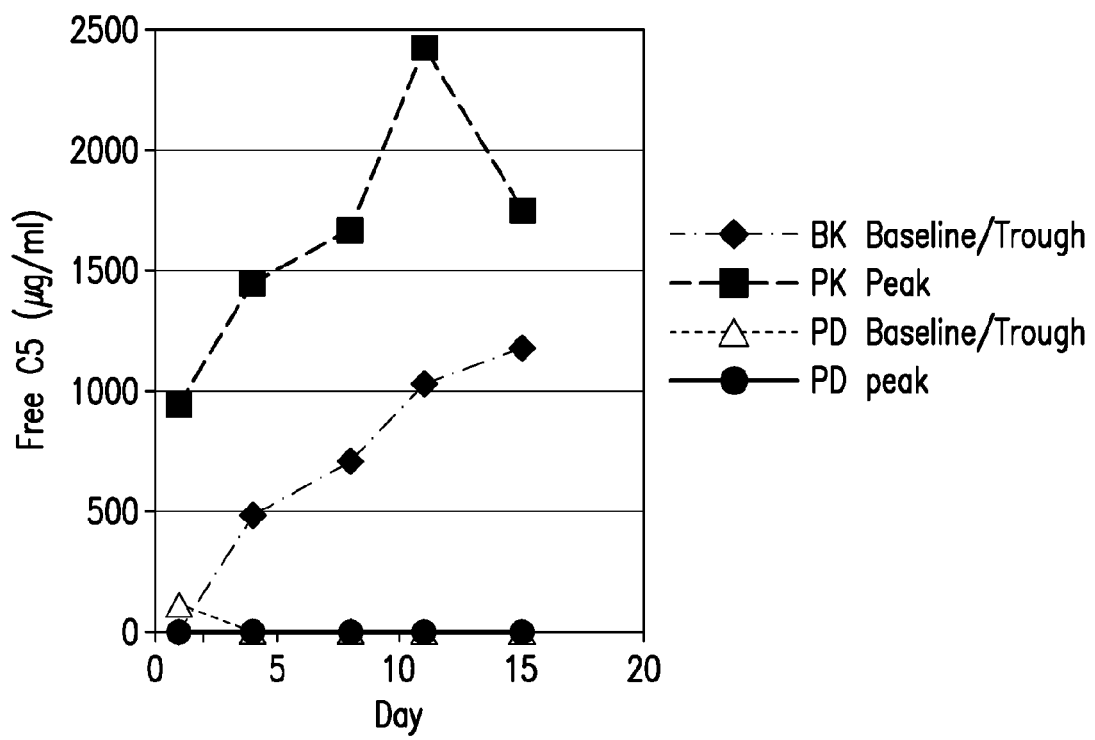
FIG. 10A is a graph depicting the pharmacokinetic (PK) and pharmacodynamic (PD) baseline/troughs in free C5 µg/mL and peaks for "Patient C" through treatment day 15.
FIG. 10B sets forth the raw PK and PD baseline/trough and peak values through treatment day 15.
Figures 11A, 11B:
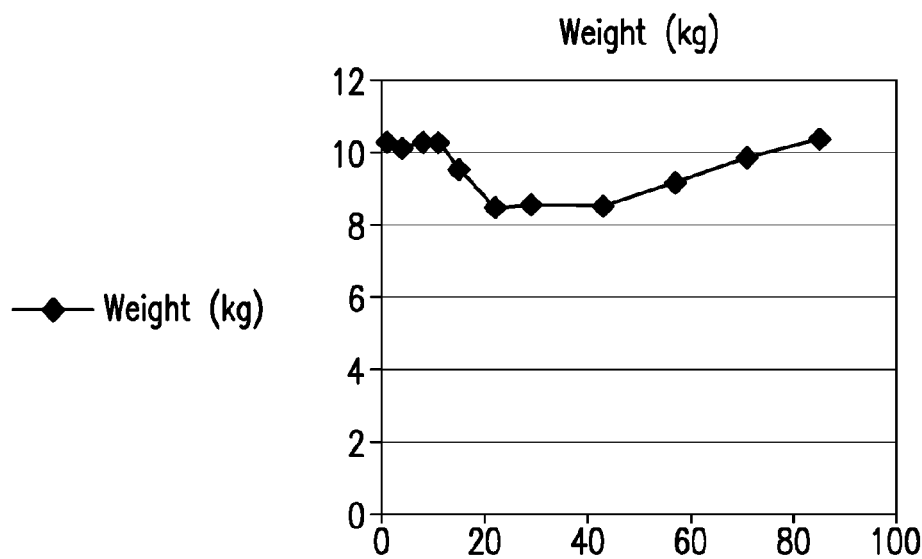
FIG. 11A is a graph depicting the weight of "Patient C" through treatment day 86.
FIG. 11B sets forth the actual weight of "Patient C" on treatment days 1, 4, 8, 11, 15, 22, 29, 43, 57, 71 and 85.

Basic laboratory and related parameters for each of the three patients are set forth in FIG. 1 ("Patient A"), FIG. 2 ("Patient B"), and FIG. 7 ("Patient C"). The weights for "Patient B" and "Patient C" over the course of treatment are set forth in FIGS. 6 and 11, respectively. PK and PD baseline/trough and peaks for "Patient B" and "Patient C" over the course of treatment until day 15 are set forth in FIGS. 5 and 10, respectively. Peak and trough timepoints for "Patient A" (days 29, 43, 57 and 71), "Patient B" (days 43, 57, 71so and 85), and "Patient C" (day 114) are shown in Table 7.

TABLE 7

Serum Samples for PK and PD of Primary Intestinal Lymphangiectasia Patients Receiving Eculizumab

| Patient ID | Timepoint | | Date | Time | #Aliquots | |
|---|---|---|---|---|---|---|
| C | Day 114 | Trough | 13 Mar. 2017 | 9:55 | 6 | |
| | | Peak | | 12:10 | 6 | Total 12 |
| | Day 43 | Trough | 12 Mar. 2017 | 11:25 | 6 | |
| | | Peak | | 13:30 | 6 | |
| | Day 57 | Trough | 26 Mar. 2017 | 10:00 | 6 | |
| B | | Peak | | 14:20 | 5 | |
| | Day 71 | Trough | 9 Apr. 2017 | 11:00 | 4 | |
| | | Peak | | 13:30 | 5 | |
| | Day 85 | Trough | 23 Apr. 2017 | 12:15 | 6 | |
| | | Peak | | 14:20 | 5 | Total 43 |
| A | Day 29 | Trough | 12 Mar. 2017 | 9:10 | 6 | |
| | | Peak | | 13:00 | 6 | |
| | Day 43 | Trough | 26 Mar. 2017 | 10:00 | 4 | |
| | | Peak | | 14:00 | 4 | |
| | Day 57 | Trough | 9 Apr. 2017 | 10:15 | 4 | |
| | | Peak | | 13:20 | 5 | |
| | Day 71 | Trough | 23 Apr. 2017 | 10:15 | 4 | |
| | | Peak | | 13:50 | 4 | Total 37 |
| | | | | | | Total 92 |

Figures 4A, 4B:
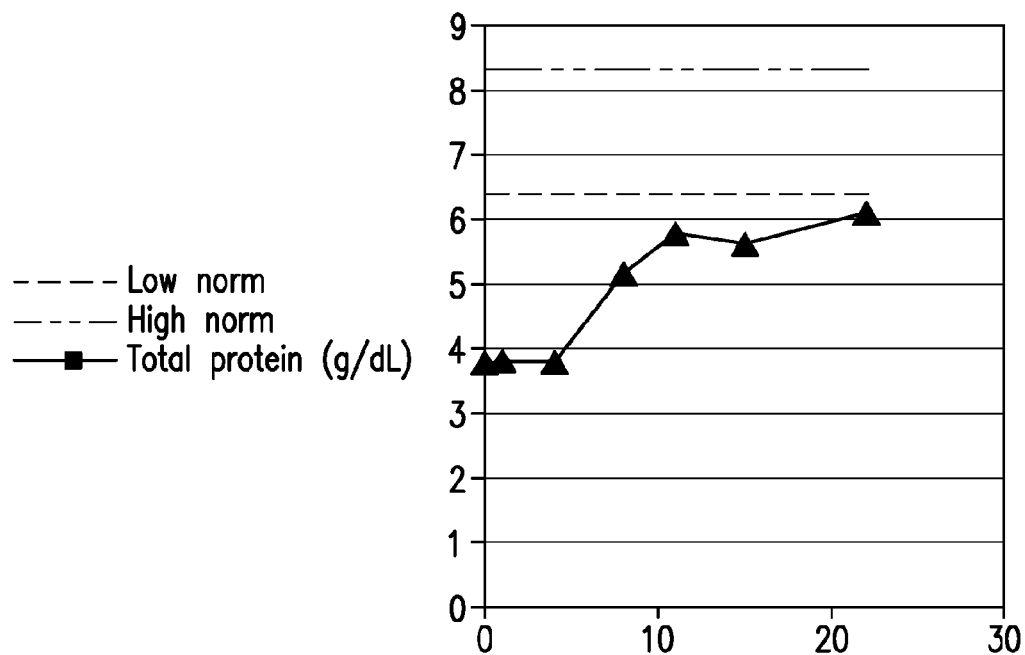
FIG. 4A is graph depicting total serum protein levels of "Patient B" (compared to low and high normal values) through treatment day 22.
FIG. 4B sets forth the raw total serum protein levels for "Patient B" (compared to low and high normal values) through treatment day 22.

As shown in FIG. 3, serum albumin levels for "Patient B" increased by about 1.7-fold compared to baseline after 20 days of treatment. As shown in FIG. 4, total serum protein levels for "Patient B" increased by about 1.5-fold compared to baseline after 20 days of treatment.

Figures 8A, 8B:
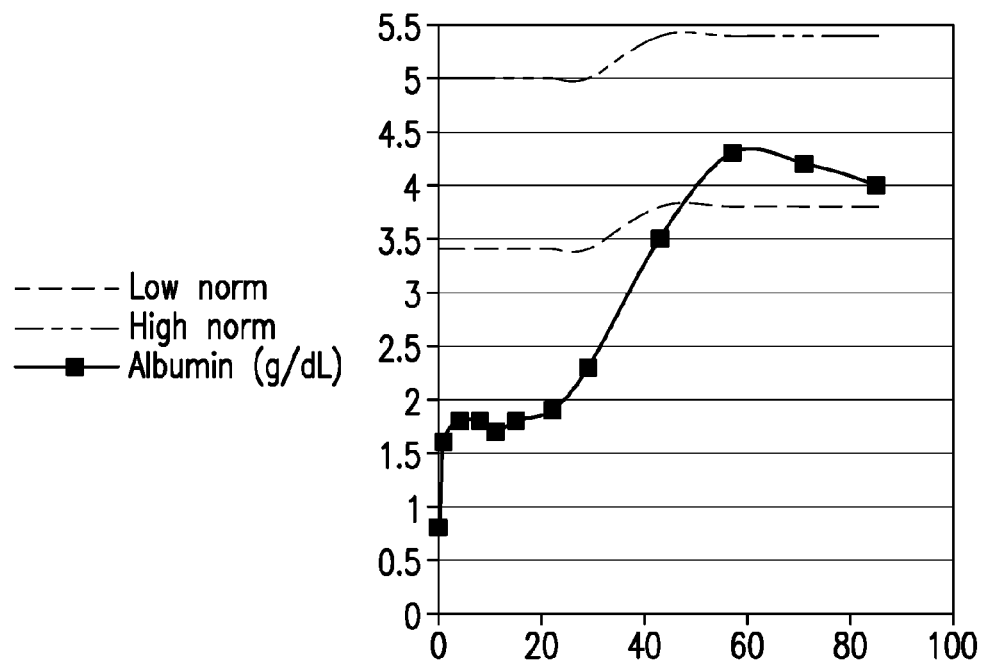
FIG. 8A is graph depicting serum albumin levels of "Patient C" (compared to low and high normal values) through treatment day 85.
FIG. 8B sets forth the raw serum albumin levels for "Patient C" (compared to low and high normal values) through treatment day 85.
Figures 9A, 9B:
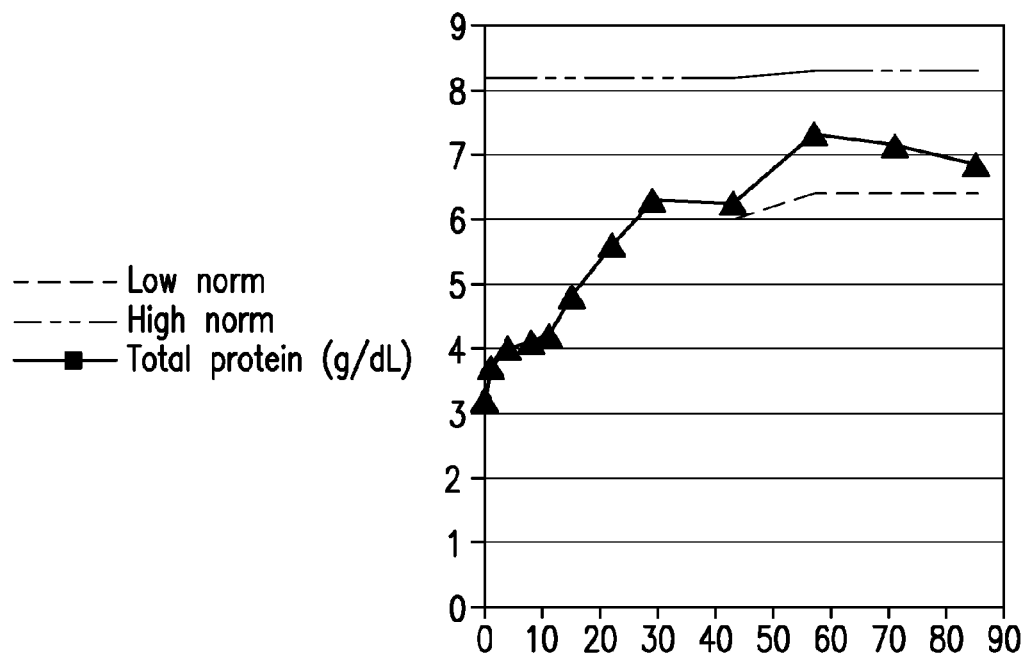
FIG. 9A is graph depicting total serum protein levels of "Patient C" (compared to low and high normal values) through treatment day 85.
FIG. 9B sets forth the raw total serum protein levels for "Patient C" (compared to low and high normal values) through treatment day 85.
Figure 12:
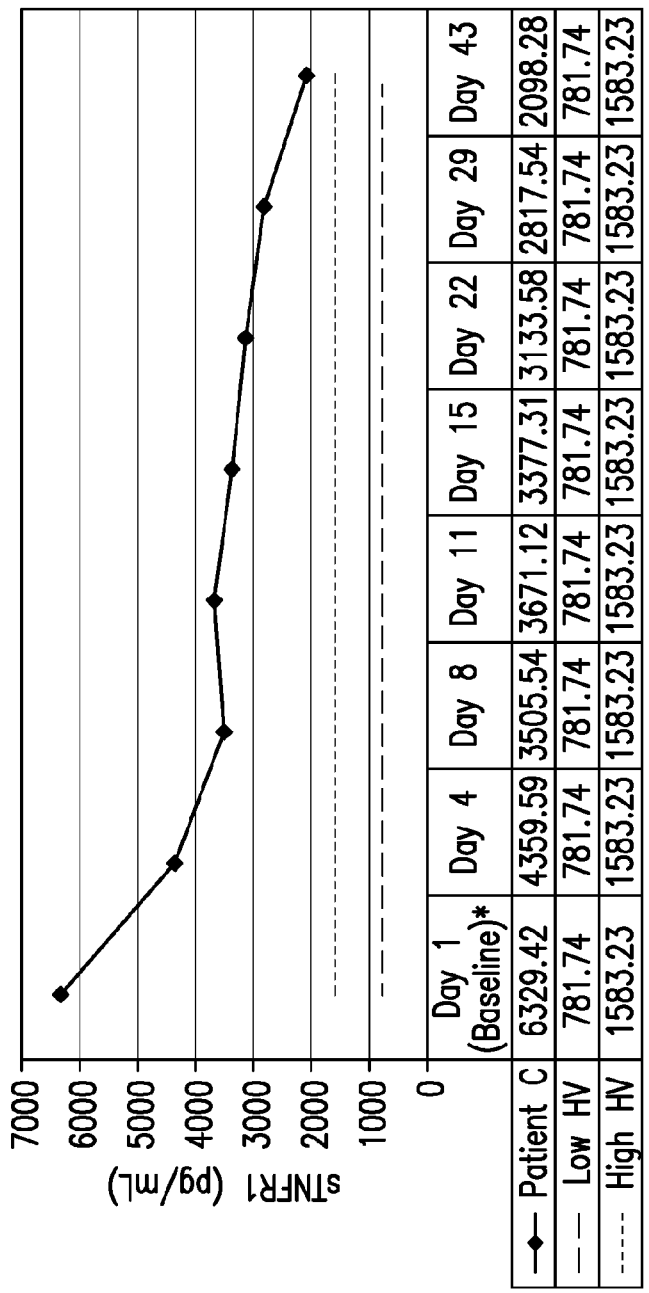
FIG. 12 is a graph depicting the serum TNFR1 levels for "Patient C" through treatment day 43 (compared to low and high normal values).

As shown in FIG. 8, serum albumin levels for "Patient C" increased by about 5-fold compared to baseline after 80 days of treatment. As shown in FIG. 9, total serum protein levels for "Patient C" increased by about 2.3-fold compared to baseline after 80 days of treatment. As shown in FIG. 12, soluble TNFR1 levels decreased by about 1.8-fold after 8 days of treatment and by about 3.25-fold after 43 days of treatment.

In sum, administration of eculizumab rapidly increased serum albumin and total serum protein levels and decreased soluble TNFR1 levels in pediatric patients with lymphangiectasia.

Example 3: Preliminary Results from Clinical Study in Patients with Protein-Losing Enteropathy Due to Inherited Complement Dysregulation A clinical study was conducted in a large consanguineous Muslim-Arab family with six patients suffering from PLE associated with PIL and hypercoagulability. Two of the patients died due to complications from the disease and three patients were enrolled in the clinical study. Genetic analysis identified CD55 loss, suggesting complement dysregulation contributes to disease pathophysiology. This was supported by complement testing and prompted therapy with eculizumab.

I. Study Design

Study Participants

Figure 13A:
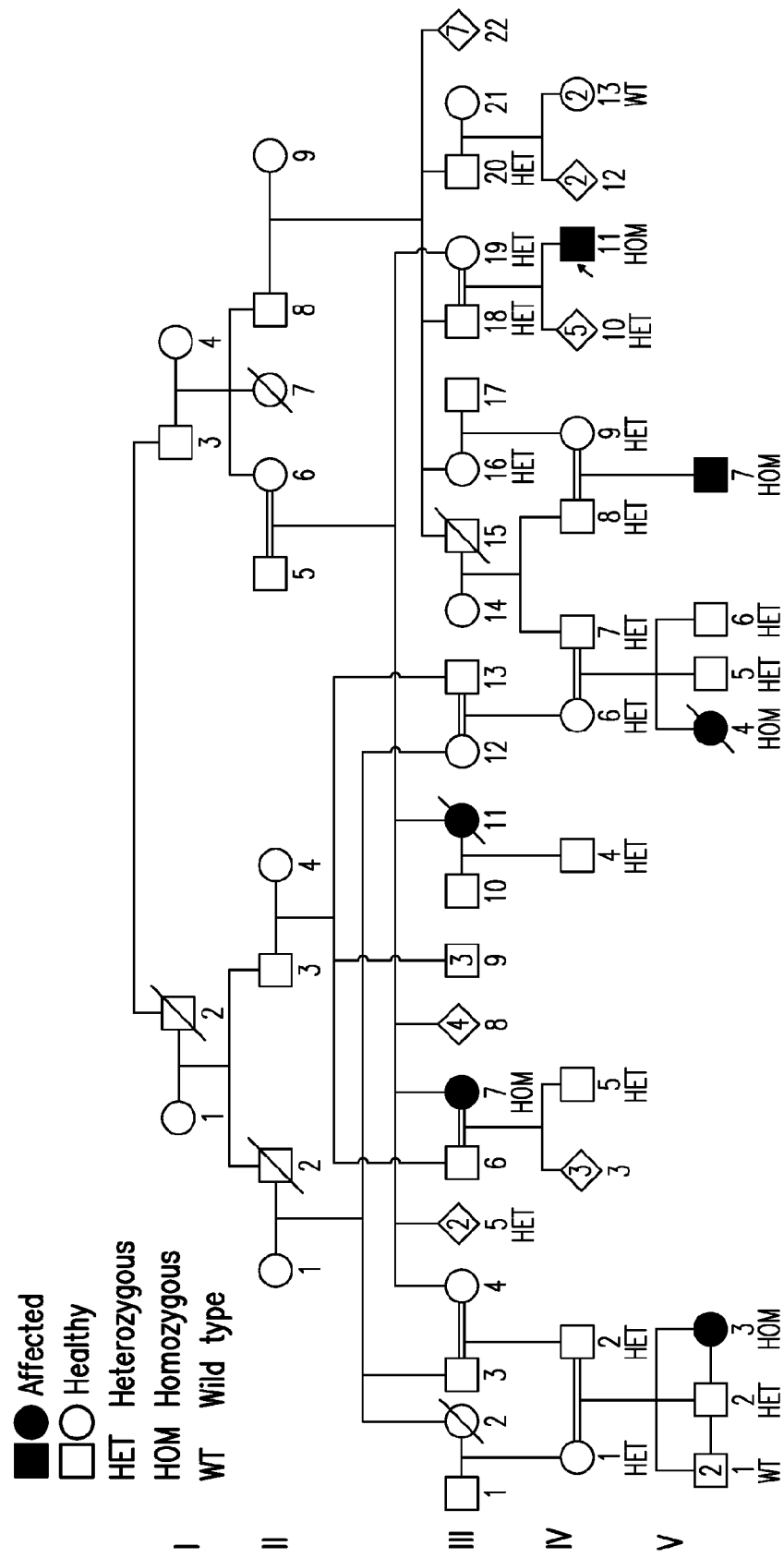
FIG. 13A shows a pedigree depicting co-segregation of the CD55 variant with PLE.

As shown in FIG. 13A, 32 members of an extended Muslim-Arab family were recruited following an institutional Helsinki Ethics Committee approval and informed consent. Phenotype was determined by a medical geneticist and a gastroenterologist for all patients, their parents and siblings. Medical records were considered where available.

Patient 1

Patient 1 (63 years old) is Patient 3's maternal aunt. She has seven healthy siblings and one affected sister (Patient 2). Their parents are third degree cousins. From the age of 3 years on, she was hospitalized multiple times due to abdominal pain, diarrhea and peripheral and facial edema. The symptoms reportedly improved at puberty. No medical records from her disease follow-ups were available. She suffered from occasional abdominal pain and diarrhea, but available laboratory workup appeared to be generally normal. At age 57 years, endoscopy revealed extensive ulceration of the colon mucosa with necrosis, acute inflammation, an inflammatory effusion mixed with fibrin and a deep mononuclear effusion consisting of lymphocytes and plasma cells. A diagnosis of inflammatory bowel disease was suggested at that time. She was not compliant with medical follow-ups or treatment. She was also diagnosed with asthma, type 2 diabetes mellitus and gastroesophageal reflux.

Patient 2

Patient 2 is a maternal aunt of Patient 3. She died at the age of 35 years from symptoms similar to the affected children in the extended family. She has one healthy son, who is heterozygous for the CD55 loss of function mutation.

Patient 3

Figure 13B:
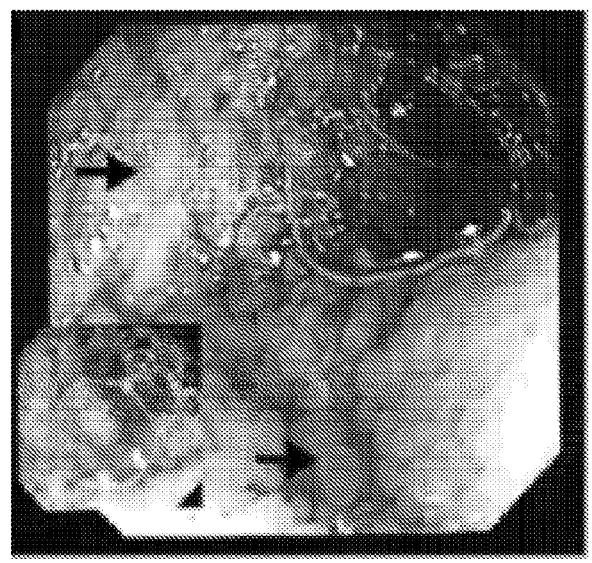
FIG. 13B and FIG. 13C are images of endoscopic and histological findings of intestinal lymphangiectasia in patient 3.
Figure 13C:
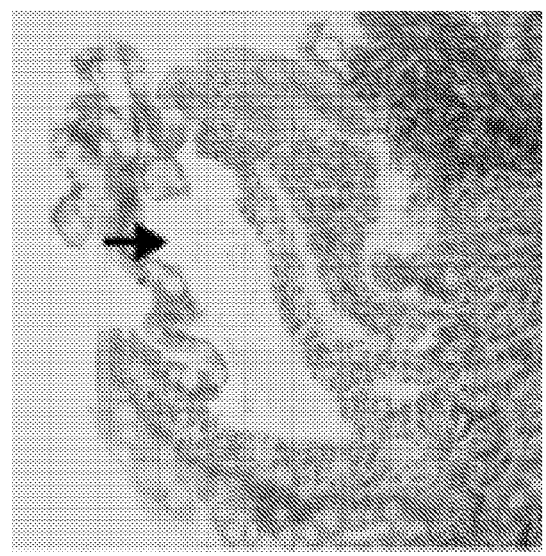

Patient 3 is a 20 year old affected son of first degree cousins. He has five healthy siblings. He presented at 2.5 years with severe abdominal pain and symptoms consistent with bowel obstruction due to intussusception. Following hospitalization, he was diagnosed with hypoalbuminemia and PLE due to PIL. The diagnosis was supported by laboratory, endoscopy, pathology and imaging findings. Specifically, FIG. 13B and FIG. 13C are images of endoscopic and histological findings of intestinal lymphangiectasia in patient 3. FIG. 13B depicts evidence of caviar-like villi (indicated by arrows) in the terminal ileum, and FIG. 13C shows dilated intestinal lymphatics (indicated by arrow), i.e. lymphangiectasia, in duodenal mucosa. In addition to the hypoalbuminemia (lowest value observed was 1.1 g/dL, normal range 3.5-5.2 g/dL), he had elevated fecal α1-antitrypsin (A1AT), and low lymphocytes and blood lipids counts. Rectal biopsy revealed edema of the lamina propria with no signs of inflammation or eosinophils. Biopsy from the jejunum was positive for increased mononuclear cells, mildly increased eosinophils, and moderate dilation of the lymphatic vessels in the submucosal layer. Duodenal biopsy showed mostly normal villous architecture. Few villi showed lymphangiectasias in the lamina propria. Abdominal magnetic resonance enterography (MRE) showed mesenterial congestion due to lymphatic dilation, consistent with PIL.

In the first years following diagnosis he was fed through a nasogastric feeding tube and later per gastrostomy with Pregestimil, which contains 55% fat consisting of middle chain triglycerides (MCT) and extensively hydrolyzed casein, and received supplementary fat-soluble vitamins (ADEK). He showed mild weight gain and height growth, but still suffered from recurrent disease exacerbations. Feeding trials with Monogen, which is high in MCTs (80% of fat), and afterward with Peptamen (70% of fat from MCT and partially hydrolyzed whey) did not improve growth, which was still non-optimal with recurrent abdominal exacerbations. An attempt of total parenteral nutrition (TPN) feeding resulted in weight gain. However, he still suffered intermittently from abdominal pain, severe diarrhea necessitating diapers, electrolyte disturbances, and recurrent bowel obstructions due to small intestine intussusceptions. He had severe scrotal edema and testicular torsion, leading to testicular atrophy. In addition, he had recurrent central line thrombosis with two events of superior vena cava (SVC) syndrome, even under anticoagulation treatment with enoxaparin. Laboratory investigation for hypercoagulability was normal, and enteral loss of anti-coagulation factors was proposed as the etiology for his hypercoagulable state.

Prior to eculizumab initiation, Patient 3 received Peptamen per-gastrostomy and an oral low fat diet, to which he was not completely adherent, and was a candidate for intestinal transplantation. His weight was stable with albumin~3 g/dL, but he still suffered from intermittent exacerbations, ascites and constant diarrhea requiring use of diapers. Due to persistent hypokalemia related to chronic diarrhea, he was treated with supplemental potassium chloride 6 doses of 25 mEq per day. He had poor hair growth and acquired ichthyosis due to lipid and vitamin malabsorption. His poor quality of life led to severe anxiety treated with olanzapine.

Patient 4

Patient 4 is 10 years old. She was born to first degree cousins, following an uneventful full-term pregnancy. She has three healthy brothers. Her development was normal until age 1 year 3 months, when she presented with diarrhea, severe hypoalbuminemia (lowest recorded albumin was 0.8 g/dL), anemia and a weight gain secondary to anasarca. Pathology findings showed nodular edematous gastric and duodenal mucosa. In light of familial history, PLE was suspected and she was put on a low fat diet and formula enriched with MCT. The diarrhea subsided and albumin levels slightly improved.

Throughout the years she was treated in several hospitals and had repeated events of bowel obstruction. One of these episodes resulted in emergency surgery, complicated by perforation, peritonitis, life threatening sepsis and acute respiratory distress syndrome (ARDS) that caused irreversible cognitive and psychomotor damage.

Prior to eculizumab initiation, she was fed per-gastrostomy with Peptamen Junior, with albumin levels at 1-2 g/dL. She had low adherence to medical treatment and dietary recommendations, and did not comply with scheduled follow-ups. She was hospitalized due to severe ascites, requiring repeat drainage and albumin supplementation, with peripheral edema leading to inability to walk. During the hospitalization, she developed bowel obstruction requiring emergency surgery, but due to severe adhesions and swelling, the anatomical structure of the intestines could not be determined, and she was left with multiple abdominal drains. Following the surgery, she suffered from constant severe abdominal pain treated with opioids, had no bowel movements, and was fed by TPN. Abdominal imaging with contrast medium failed to show multiple parts of her intestinal tract.

Patient 5

Patient 5 was born to first degree cousins and had two healthy brothers. She presented at age 10 months with diarrhea, recurrent bowel obstructions, severe hypoalbuminemia (lowest recorded albumin was 0.5 g/dL) and failure to thrive (FTT). PLE was suspected due to familial history. Biopsies from the small intestine revealed chronic mild inflammation, as well as two hyperplastic lymphatic aggregates in the duodenal lamina propria. However, dilation of the lymphatics was not observed. Capsule endoscopy revealed a protrusion into the small intestine, prompting computed tomography enterography (CTE). CTE was positive for nodular thickening of the proximal and distal small intestine walls, and a suspected intestinal intussusception. A low-fat MCT-rich diet was started, but Patient 5 did not demonstrate improvement in her albumin levels or in her growth. This was probably due to poor compliance. Moreover, she developed severe electrolyte deficiencies, including hypokalemia, hyponatremia and hypomagnesemia.

At 2.5 years she suffered from hepatic vein thrombosis with a clinical presentation of Budd Chiari syndrome. She was treated with enoxaparin and diuretics. A central line was inserted for TPN administration with no improvement in diarrhea or albumin levels. Furthermore, she had recurrent line infections and sepsis and subsequently SVC syndrome leading to severe respiratory insufficiency. A coagulation panel was positive only for a homozygous MTHFR (MIM #607093) C677T mutation and she received anticoagulation therapy. The line was removed and she was fed by a nasogastric tube, but her medical and dietary condition kept deteriorating. She had severe anasarca and acrodermatitis enteropathica-like rash, leading to failed venous access. She died at age 4 years, due to severe intestinal failure.

Patient 6

Patient 6 was born prematurely to first degree cousins at week 36 by Caesarean section due to polyhydramnios and breech position. Prenatal genetic evaluation was performed due to polyhydramnios and chromosomal microarray analysis (CMA) was normal. At birth, he weighed 2.4 kg (25-50$^{th}$ percentile) and exhibited pronounced hypotonia, hydrocephalus and respiratory distress of an unknown etiology. A metabolic workup was normal. A ventriculoperitoneal (VP) shunt was inserted and he was fed by gastrostomy. He displayed global developmental delay. Brain MRI revealed asymmetry of the skull, the hemispheres and the ventricles, periventricular white matter depletion, and thin corpus callosum. The neurological phenotype was not considered to be part of the familial PLE syndrome.

In view of the family history, Patient 6 was tested and found homozygous for the CD55 c.43del mutation. He was followed-up with by the pediatric gastroenterology unit, but initially exhibited no signs of PLE. At the age of 1 year and 11 months he was hospitalized with acute manifestation of severe diarrhea, hypoalbuminemia (lowest recorded albumin 0.6 g/dL), anasarca and FTT. No proteinuria was observed and elevated fecal A1AT pointed to the diagnoses of PLE. He was immediately put on Pregestimil diet per-gastrostomy, which improved the diarrhea and stabilized his albumin levels at ~1 g/dL. Abdominal ultrasonography was positive for thickened edematous and hyperemic intestines with moderate intraperitoneal fluid in the abdomen and pelvis. During hospitalization, an event of focal seizures led to diagnosis of right sagittal sinus vein thrombosis by brain CT. A coagulation panel revealed that he was positive for the heterozygous factor V Leiden mutation and mildly elevated factor VIII. He was treated with enoxaparin.

Prior to eculizumab initiation, his albumin levels were still very low and he suffered from diarrhea. Due to the severe malabsorption, he developed pronounced acrodermatitis enteroepathica-like rash with secondary fungal infection, which was treated with topical steroids and antifungals without success. He was hospitalized in a critical state, including hypoalbuminemia (1.5 g/dL), and severe anasarca. He received intraosseous albumin infusions and fluids containing electrolytes, with no improvement. His condition rapidly declined and he displayed hypothermia (34.8 C), low blood pressure (88/55) and Cheyne-Stokes respiration, necessitating oxygen supplementation with a non-rebreather mask. His blood-work was positive for respiratory acidosis (pH 7.17, normal 7.35-7.45; $pCO_2$ 88 mmHg, normal 35-45).

Genetic Analysis

DNA samples from Patients 3, 4 and 5 (Table 8) and one healthy mother underwent whole exome sequencing (WES) on the HiSeq2000 platform (Illumina, San Diego, Calif., USA) using the Nextera Rapid Capture Enrichment kit (Illumina). Reads were mapped against the reference genome (GRCh37/hg19) and variants were called on the Genoox data analysis platform Ltd. (Tel Aviv, Israel), which also served for data analysis.

The consanguinity and extended family structure, comprising six individuals diagnosed with PLE of variable severity, suggested autosomal recessive inheritance. Therefore, WES filtering criteria included rare (MAF<0.01 in control populations of European and Middle-Eastern descent) homozygous protein-altering variants (mis sense, nonsense, frameshift, splice-site) in the patients, which were heterozygous in the healthy mother. Variants were prioritized based on predicted functional consequences and relevance to phenotype by literature, OMIM and VarElect (Stelzer et al., *BMC Genomics.* 2016; 17(52):444). Sanger sequencing was used for variant validation and co-segregation. Primers were designed using ExonPrimer (https://ihg.gsf.de/ihg/ExonPrimer.html). Primers for the CD55 variant included ACGAGGCTTCTGCTTACTGC (forward; SEQ ID NO:36) and CAGAGACCGACTTGGACCTC (reverse, SEQ ID NO:37). Sequencing was performed on an ABI Prism 3500 Genetic Analyzer (Applied Biosystems), following manufacturer protocols. Sequencher 5.3 software (GeneCodes Corporation, Ann Arbor, Mich., USA) was used for variant analysis.

Protein Detection

Flow cytometry for CD55 was performed using PE-conjugated anti-CD55 (JS11KSC2.3, Beckman Coulter, Brea, Calif., USA) on the Navios flow cytometer (Beckman Coulter) on RBCs and granulocytes. Results were analyzed with FCS Express 6 Plus (De Novo Software, Glendale, Calif., USA).

In addition, CD55 antigens (Cromer blood typing) were assayed by hemagglutination, using ID-Card Coombs Anti-IgG (Bio-Rad, Hercules, Calif., USA) and human antibodies (anti-$Dr^a$, anti-$Es^a$, anti-$Cr^a$, anti-CROK) from the National Blood Group Reference Laboratory in-house rare anti-sera collection. Anti-$Es^a$, anti-$Cr^a$, and anti-CROK eluates were prepared by adsorption onto antigen-positive red blood cells (RBCs) and eluted using ELU KIT® (Immucor, Norcross, Ga., USA). Positive control red blood cells (RBCs) for the specific antigens and negative control αChymotrypsin-treated RBCs were included.

Complement Studies

RBCs and neutrophils were stained to evaluate iC3b (product of C3b cleavage) and MAC deposition. RBCs were stained immediately and neutrophils were isolated and allowed to age in the presence of 10% autologous fresh serum. Then 5 μL of fresh, citrate-anticoagulated blood was diluted with 1 mL PBS×1. A total of 100 μL of diluted blood was used for each stain. Neutrophils were isolated as previously described (Mevorach, D., *Mol. Immunol.,* 67:51-5, 2005). Next, 1 μg of either monoclonal anti-human SC5b-9 or iC3b antibodies (Neoantigen, Quidel, San Diego, Calif., USA) was added, and cells were incubated for 30 minutes on ice. After incubation, cells were washed and stained with 1:100 of R-Phycoerythrin-AffiniPure F(ab')2 fragment goat anti-mouse IgG (H+L) secondary antibody (Jackson ImmunoResearch Laboratories, Inc., West Grove Pa., USA). Cells were then incubated for an additional 20 minutes on ice, washed twice, and analyzed using the FACSCalibur flow-cytometer (Becton Dickenson, Franklin Lakes, N.J., USA).

Eculizumab Treatment Protocol and Monitoring

Compassionate off-label use of eculizumab was authorized by the Rambam Health Care Campus regulatory authorities, and administered following signed informed consent by the patients or their parents. All patients were vaccinated and received prophylactic antibiotics as customary in eculizumab treatment.

The treatment regimen was adjusted from the PNH/aHUS protocols to account for the enteric protein loss in these patients. The induction phase included two eculizumab infusions per week for two weeks, followed by three weekly doses. Thereafter, patients received infusion every two weeks for maintenance. Dosing was determined by patient weight: 600 mg per treatment for 10-30 kg weight, 900 mg for 30-40 kg weight, and 1200 mg for weight >40 kg.

Patients were carefully monitored each treatment for vital signs, weight, adverse reactions, and laboratory workup including complete chemistry panel, complete blood count (including smear for schistocytes), complement (C3, C4 free C5) and immunoglobulin levels, C-reactive protein, pro-thrombotic measures (fibrinogen, d-dimers), and hemolysis markers (LDH, haptoglobin). Response to treatment was evaluated by albumin and total protein levels, bowel movement frequency and consistency, weight, physician assessment, and patient/parent accounts of overall well-being.

II. Results

Clinical Summary

Comprehensive clinical descriptions for each patient are reported in Table 8. Disease onset was between ages 10 months to 3 years, presenting with generalized edema, severe hypoalbuminemia, diarrhea, distended abdomen and abdominal pain. Patients 2 and 5 died at ages 35 and 4 years, respectively, due to disease complications. PLE diagnosis was supported by laboratory findings of elevated fecal A1AT in Patients 3 and 6, and low lymphocyte counts in most patients. PIL characteristics were only demonstrated in one patient (Patient 3) through endoscopy, pathology and imaging studies showing swollen lymphatics, shown in FIGS. 13D and 13E, consistent with known literature on the complicated demonstration of PIL. Consistent with PLE diagnosis, a low-fat diet with MCT-rich formula and fat-soluble vitamin supplementation, mainly per gastrostomy or total parenteral nutrition (TPN), has been effective in the patients, when compliant.

Repeated thrombotic events were noted in three of the patients, including recurrent central-line thrombosis (Patients 3 and 5), Budd-Chiari (Patient 5), superior vena cava syndromes (Patients 3, 5 and 6), and sinus-vein thrombosis (Patient 6). Hypercoagulation and clotting panels did not yield a common cause (Table 8).

TABLE 8

Clinical findings in protein losing enteropathy patients with CD55 loss of function

| | 1 | 2 | 3 | 4 | 5 | 6 |
|---|---|---|---|---|---|---|
| Gender | F | F | M | F | F | M |
| Age at onset | 3 yr, improved at puberty | Early childhood | 2.5 yr | 1 yr 3 mo | 10 mo | 1 yr 11 mo |
| Current age | 63 yr | Died at 35 yr | 21 yr | 11 yr | Died at 4 yr | 3 yr |
| *Clinical presentation before eculizumab treatment* | | | | | | |
| Hypoalbuminemia | N/A | N/A | Severe (1.1-3.2 g/dL) | Severe (0.8-1.7 g/dL) | Severe (0.5-3.1 g/dL) | Severe (0.6-1.5 g/L) |
| Edema | Yes, improved | Peripheral and ascites | Peripheral and ascites | Peripheral and ascites | Anasarca | Anasarca |
| Diarrhea | Yes | Yes | Yes, constant (>30/day) | Yes* | Intermittently | Yes, >10/day |
| Thrombosis | No | No | SVC syndrome, recurrent | No | Budd-Chiari syndrome, SVC syndrome | Chronic sinus vein thrombosis, SVC syndrome |
| Dermatologic findings | N/A | N/A | Acquired ichthyosis, poor hair growth | Poor hair growth | Acrodermatitis enterohepatica | Acrodermatitis enterohepatica, poor hair growth |
| Other | Gastritis, T2DM, myopia, sensorineural hearing loss, asthma | N/A | Microcephaly, myopia, asthma, nail clubbing | Asthma, irreversible neurological damage due to severe sepsis | N/A | Polyhydramnios in pregnancy, hypotonia, respiratory insufficiency, hydrocephalus, brain MRI anomalies, GDD |
| Endoscopy | N/A | N/A | Caviar-like villi in terminal ileum, inflamed edematous intestinal and colon mucosa, vascular ectasias in colon | Nodular, ruffled and edematous duodenal mucosa | Normal | Mild duodenal edema, nodular duodenal onion |
| Pathology | Ulceration of colon mucosa with necrosis and acute inflammation | N/A | Moderate dilation of jejunal lymphatic vessels in the submucosal layer, edema of rectal lamina propria | Nodular edematous gastric and duodenal mucosa | Two hyperplastic lymphatic aggregates in the duodenal lamina propria | Duodenal mucosa with lymphoid follicle |
| Imaging | N/A | N/A | Mesenterial congestion and lymphatic dilation | Mesenterial lymphadenopathy | Thickened edematous intestinal wall, ascites | Thickened edematous and hyperemic intestines with moderate intraperitoneal fluid in the abdomen and pelvis |
| Coagulation panel | N/A | N/A | Mildly elevated factor VIII | Normal | HOM MTHFR C677T | HET factor V Leiden, mildly elevated factor VIII |
| *Eculizumab treatment outcomes* | | | | | | |
| Hypoalbuminemia | | | Resolved (>4 g/dL) | Mild (~3 g/dL) | | Resolved (>4 g/dL) |
| Diarrhea | | | Resolved (2-3/day) | Resolved* | | Resolved (3-4/day) |
| Dermatologic findings | | | Resolved | Resolved | | Resolved |

Abbreviations: F, female; GDD, global developmental delay; HOM, homozygous; HET, heterozygous; M, male; mo, months; N/A, not available; susp., suspected; SVC, superior vena cava; T2DM, type 2 diabetes mellitus; yr, years.
*Patient 4 suffered from diarrhea since disease onset. Before eculizumab treatment she underwent critical abdominal surgery due to abdominal obstruction, after which she had multiple abdominal drains and did not have bowel movements. Following eculizumab treatment, she started passing stool 1-2 times per day.

Patient 1 (63 years old at time of study) reported repeated hospitalizations for similar complaints, including recurrent peripheral and facial edema since three years of age, which improved at puberty. No medical records from her disease follow-up are available and she continues to suffer from occasional abdominal pain and diarrhea.

Homozygous Frameshift Variant in CD55 Identified in PLE Patients

Figure 13D:
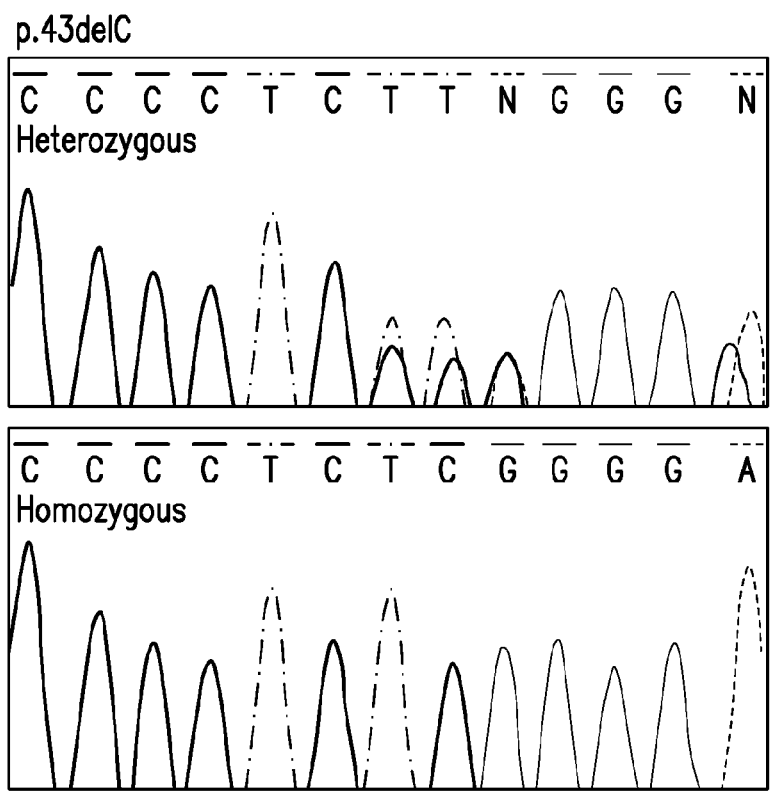
FIG. 13D shows sequence chromatograms of a patient (homozygous) and a healthy parent (heterozygous), depicting the CD55 NM_001114752.1: c.43del variant.

WES bioinformatic analyses failed to identify rare deleterious variations in lymphatics-related genes, while unbiased analysis revealed a homozygous frameshift variant in the first exon of CD55. The variant, NM_001114752.1:c.43del (p.Leu15Serfs*46), was validated with Sanger sequencing and co-segregated with the disease in the extended family (n=32), as shown in FIG. 13D. It was absent from public variant databases, including the Greater Middle-East Variome Project, as well as an in-house database of approximately 650 control chromosomes of diverse Israeli ethnicities (Scott, E et al., *Nat. Genet.*, 48:1071-6, 2016).

Lack of CD55 Expression in PLE Patients

Figure 13E:
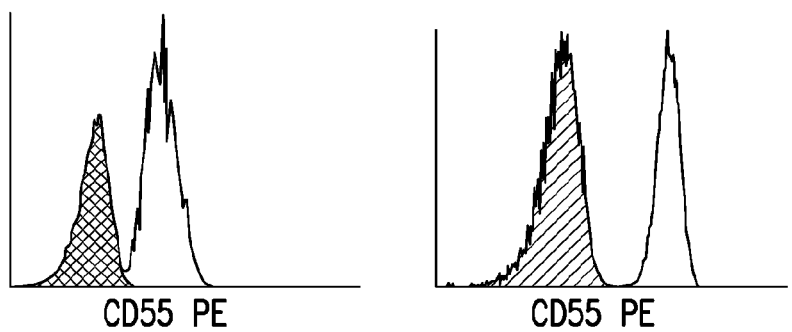
FIG. 13E shows flow cytometry analysis of CD55 revealing no binding to CD55 antigens on red blood cells of Patient 6 (black) and on neutrophils of Patients 4 and 6 (overlay histogram, black and grey) compared to normal controls (white).

No binding to CD55 antigens was detected by flow cytometry on patients' RBCs (Patients 3, 4 and 6) and granulocytes (Patients 4 and 6) compared to controls, as shown FIG. 13E). Likewise, hemagglutination tests revealed Patients 3 and 5 RBCs were type CROM:−1 [Cr(a−)], CROM:−5 [Dr(a−)], CROM:−6 [Es(a−)], CROK-negative, suggestive of the rare Cromer Inab (CD55-null) phenotype.

Complement Activation

Figure 15A:
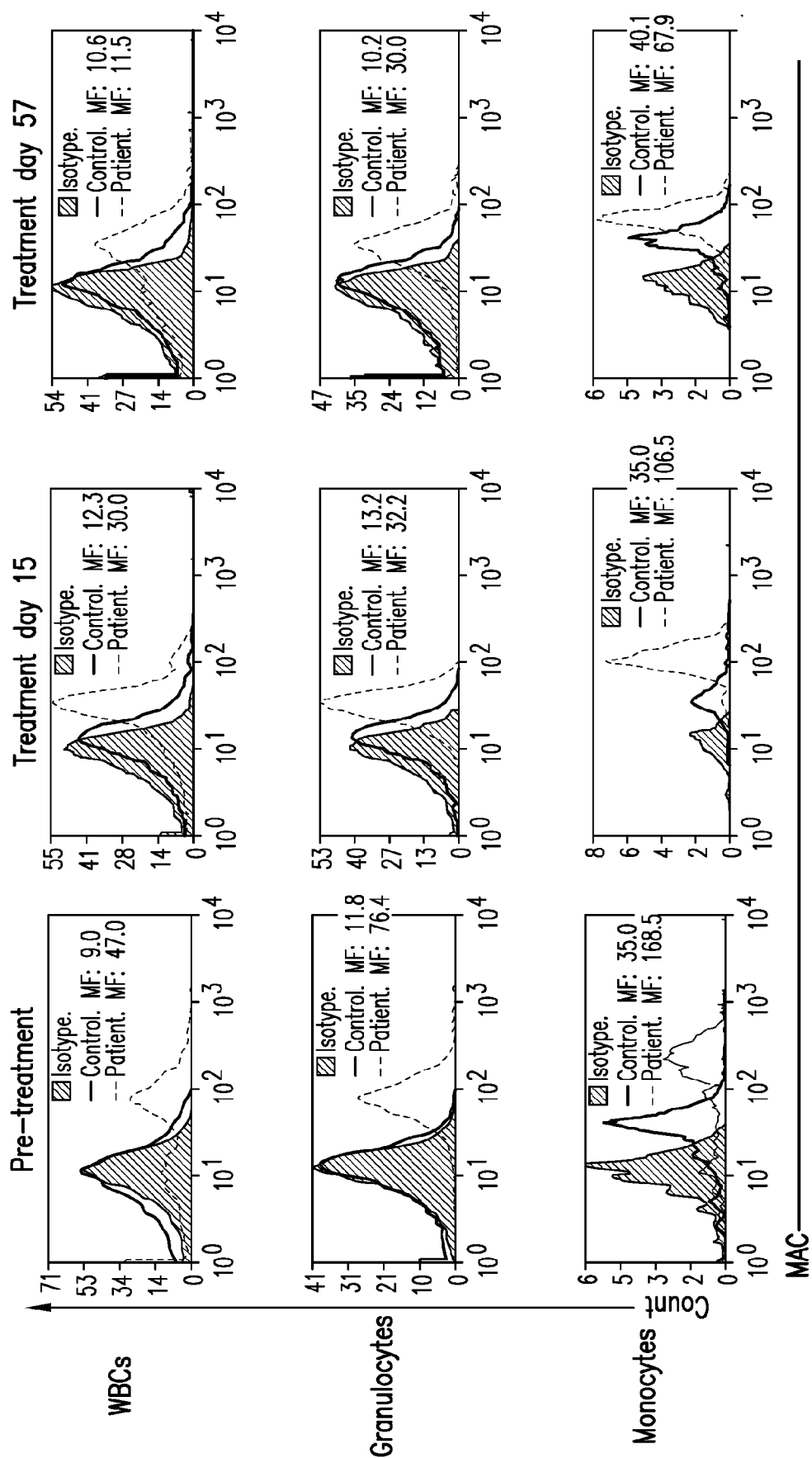
FIG. 15A depicts flow cytometry of MAC on total WBCs, granulocytes, and monocytes in Patient 4 and age-matched controls pre-treatment, after 15 days of treatment, and after 59 days of treatment.
Figure 15B:
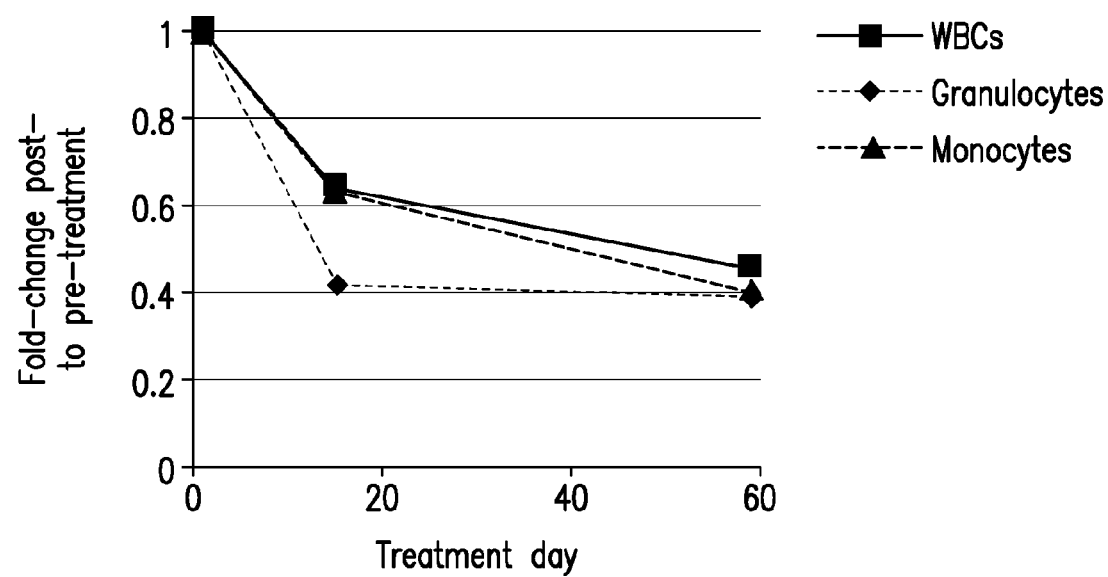
FIG. 15B demonstrates the significant reduction in MAC-depositions on cells compared to pre-treatment values.
Figure 16:
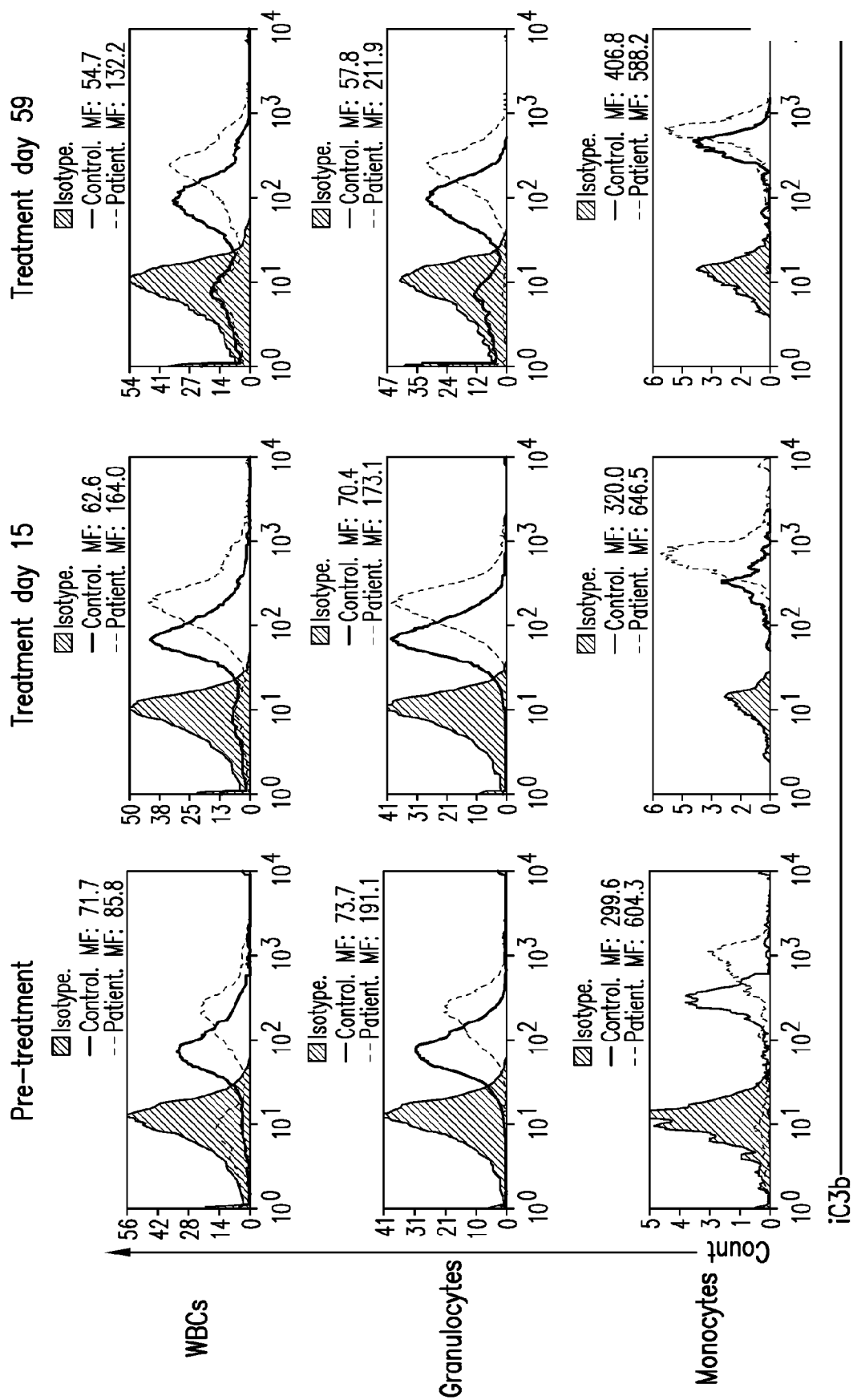
FIG. 16 shows flow cytometry of iC3b on total WBCs, granulocytes, and monocytes in Patient 4 and age-matched controls pre-treatment, after 15 days of treatment, and after 59 days of treatment.

Both MAC and iC3b were significantly elevated ($p<0.001$) in patients compared to age-matched controls, as shown in FIGS. 15 and 16, respectively.

Clinical Response to Eculizumab Therapy

Positive response to eculizumab was observed in all three treated patients after a single treatment. Free C5 levels reduced from 110 μg/mL to below the limit of quantitation following the first dose administration.

Figure 14A:
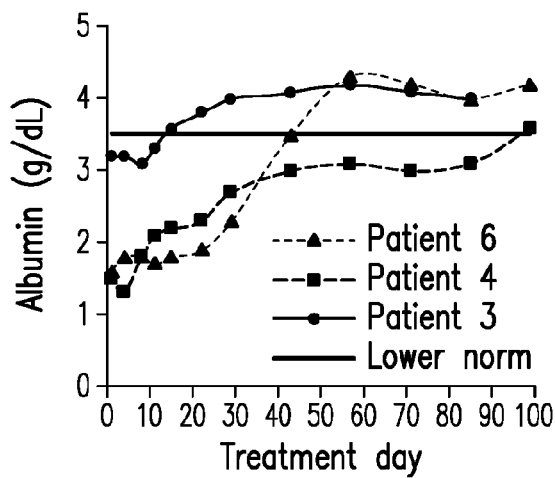
FIGS. 14A and 14B depict improvement in serum albumin and total protein concentrations from baseline and throughout 100 days of eculizumab treatment.
Figure 14B:
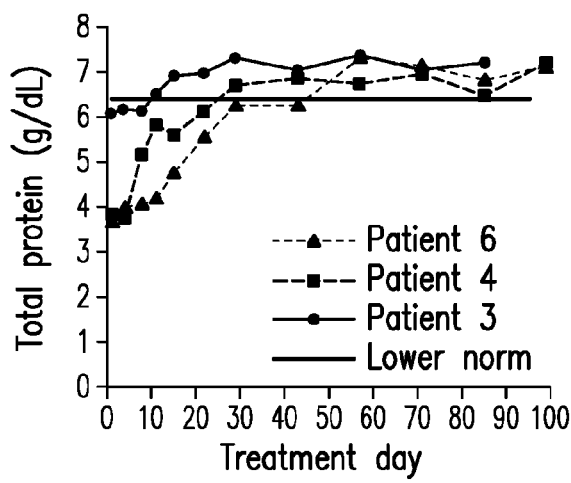
Figure 14C:
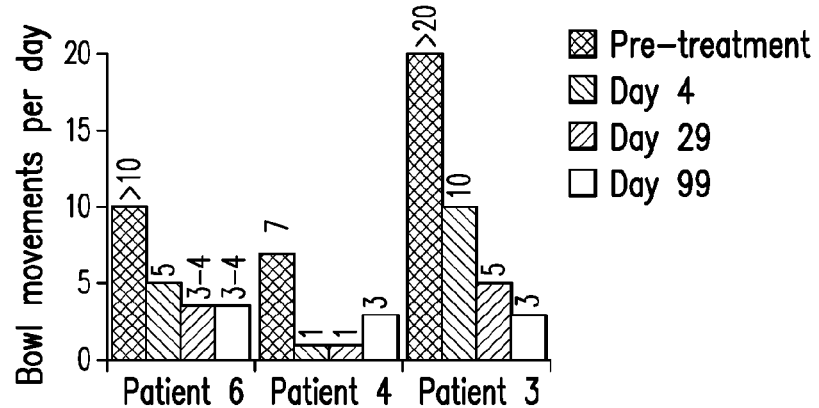
FIG. 14C reveals a striking decrease in the number of bowel movements per day following a single eculizumab dose and up to 100 days of eculizumab treatment. The decrease in number was accompanied with improvement in stool consistency.
Figure 17K:
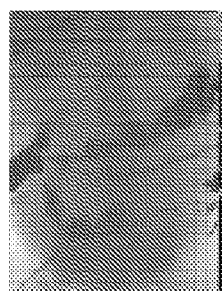
Figure 17L:
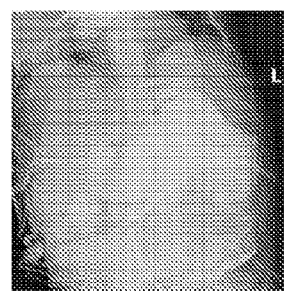

Approval for compassionate therapy was obtained first to Patient 6, a 2.5 year-old boy, who was hospitalized in critical state. He was hypothermic, hypotensive, and exhibited Cheyne-Stokes respiration, necessitating oxygen supplementation with a non-rebreather mask. Blood tests revealed severe hypoalbuminemia (1.5 g/dL) unresponsive to intravenous albumin, $pCO_2$ retention (88 mmHg, normal 35-45), and respiratory acidosis (pH=7.17, normal 7.35-7.45). He had severe anasarca (extreme generalized edema) and a very pronounced rash consistent with acrodermatitis enterohepatica due to vitamin deficiencies (Table 8; FIG. 17 (panels A-E)). Since disease onset, he had watery diarrhea >10 times per day and required furosemide for adequate urine production. After eculizumab initiation, his condition stabilized within 24 hours, with normalized vital signs and external oxygenation with nasal cannula. The acidosis was rapidly resolved ($pCO_2$=42 mmHg, pH=7.46). His urination improved and he lost 1.5 kg of weight in fluids within two weeks, essentially resolving the severe anasarca. His rash remarkably improved with supplemental therapy with steroid and antifungal creams and several doses of intravenous vitamins, as shown in FIG. 17 (panels A-E). He was discharged from the hospital after 17 treatment days. Currently, his bowel movements reduced to 3-4 times per day, as shown in FIG. 14, and he is smiling and interacting. His albumin and total protein levels normalized within a month and have been stable thereafter.

Figure 18A:
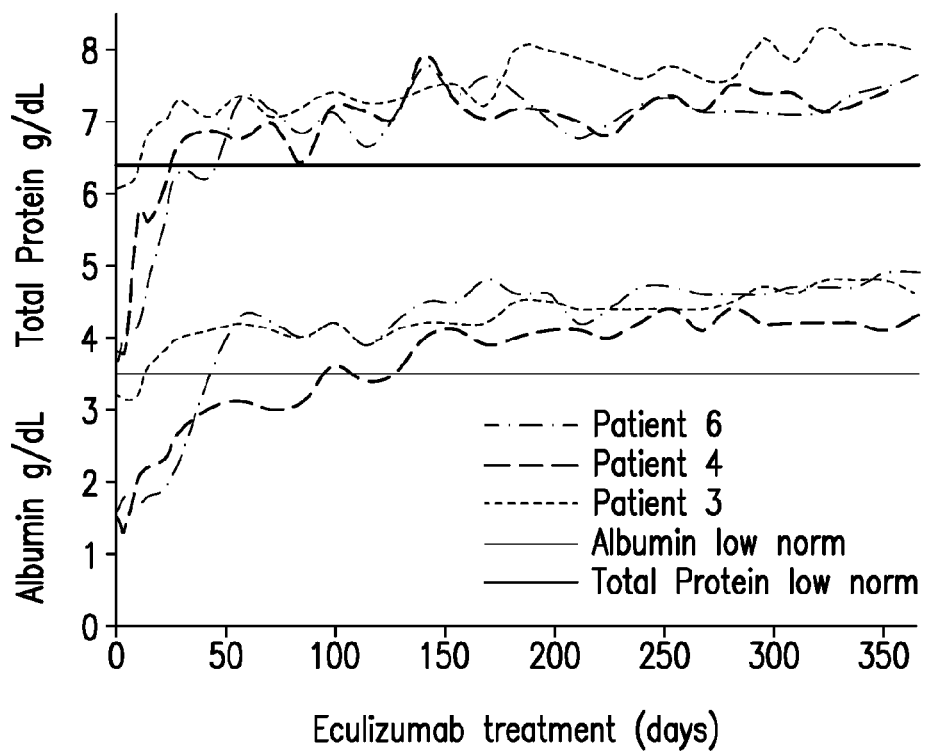
FIG. 18A depicts albumin (g/dL) and total protein (g/dL) levels post-treatment with eculizumab for patients 6, 4 and 3, as well as total protein low norm (top line) and albumin low norm (bottom line).

Following the dramatic therapy results of Patient 6, approval was obtained for compassionate therapy for two other patients. Patient 4, a 10 year-old girl, was hospitalized with malnourishment, hypoalbuminemia 1.7 g/dL unresponsive to intravenous albumin, repeat episodes of dehydration, significant ascites, abdominal pain, and edematous legs causing inability to walk. She had an abdominal obstruction and underwent surgery, leaving multiple stomas and abdominal drains. Prior to eculizumab treatment, she was in constant severe abdominal pain requiring opioid treatment. Abdominal imaging with contrast medium failed to demonstrate multiple parts of her intestinal tract, as seen in FIG. 17 (panel K). Following the first dose, her mother noted alleviation of the abdominal pain and she has stopped receiving pain medication. Within several days her appetite returned, she started passing stool, and her albumin returned to stable levels (~3 g/dL) with total protein within normal range, as shown in FIG. 14. Repeat imaging after 65 days on eculizumab revealed vast improvement in her abdominal status, shown in FIG. 17 (panel L), and she underwent surgery, which allowed saving enough intestines (approximately 140 cm) for maintaining quality of life. Intestinal biopsy taken during the corrective surgery did not reveal the lymphangiectasias observed in biopsies taken prior to eculizumab treatment. She was discharged after a six month hospitalization with normalized albumin and total protein levels, which remain stable (see FIG. 18A). In addition, she regained control of her bowel movements, which reduced to 2-3 times per days with normal consistency. She weaned off gastrostomy feeding, and the tube was removed.

Patient 3, a 20 year-old man, was suffering from repeat intussusceptions and abdominal pain episodes, ascites, and secondary bilateral inguinal hernia, as well as hypokalemia requiring significant potassium supplementation. He was a candidate for bowel transplantation and also suffered from acquired ichthyosis due to reduced lipid and vitamin absorption (FIG. 17 (panels F-J)). Although his albumin level was 3.2 g/dL (not as significantly low as the other patients), he reported constant uncontrolled diarrhea requiring a diaper, which hindered quality of life and affected his mood requiring treatment with antidepressants. He reported feeling better after the first eculizumab infusion. Within a week, he stopped wearing a diaper due to reduced frequency and normal consistency of bowel movements (FIG. 14). His ascites slowly improved, as well as the ichthyosis, as shown in FIG. 17 (panels H-J), and he gained 3 cm in height within 43 days of treatment. His albumin and total protein levels normalized within two weeks, as reported in Table 8 and FIG. 14. His ascites, ichthyosis and nail clubbing completely resolved. He stopped taking potassium supplements and his potassium levels remained stable. He no longer requires chronic medication and dietary supplementation, and his gastrostomy was removed. He reports eating a normal diet, including fatty food, without PLE exacerbations. His body mass index (BMI) improved from 15.9 to 21.1, and he grew 6.5 cm in height within one year (see FIG. 18B). At age 21 years, Patient 3, who was previously withdrawn, displays motivation, vitality, and has finally achieved a level of independence commensurate with his age-matched peers. He depends less on his mother's assistance in everyday chores, reports having a good mood without antidepressants, and shows motivation to become more independent.

The positive clinical response to eculizumab, as observed in all three treated patients after the first treatment, was accompanied by continuous improvement in serum albumin and total protein, and decreased complement activation. The acute disease manifestations resolved, including rapid stabilization of the critical condition of Patient 6 and a marked reduction in the frequency of bowel movements in all three patients. The first sign of attenuated protein loss was normalization of total protein levels within 2-4 weeks; serum albumin levels normalized shortly thereafter. Moreover, dietary restrictions were lifted and patients were able to go back to their daily routines without major complications.

Free C5 levels decreased to below the limit of detection following the first dose, and MAC deposition on WBCs declined (FIG. 15). In Patient 4, MAC deposition was reduced from 5.2-fold (compared to control) to 2.1-fold in WBCs (p<0.01), from 6.5-fold to 3-fold in granulocytes (p<0.01), and from 4.5-fold to 1.7-fold in monocytes (p<0.01). Overall, 60% decrease in MAC deposition was observed on treatment day 59 compared to pre-treatment levels (FIG. 15). Deposition of iC3b was increased in WBCs and granuloctyes (p<0.05) (FIG. 16). Patient 3 showed similar pattern, and Patient 6, whose MAC and iC3b depositions were studied only post-treatment, showed similar post-treatment depositions as the others.

No serious adverse events were observed during eculizumab treatment. Patient 3 reported headache and dizziness after the second dose, which was not repeated otherwise. Despite being vaccinated prior to eculizumab initiation and prophylactic antibiotics, Patient 6 had *Haemophilus influenzae* type b pneumonia, which resolved after intravenous antibiotics. Patient 4 developed mild thrombocytopenia of ~160×10³/μL (normal: 200-370) after five months of treatment, and currently remains stable. She had an episode of elevated liver enzyme functions, which resolved spontaneously with normal ultrasonography and negative viral workup. Interestingly, all three patients experienced a 1.5-2.5 g/dL drop in hemoglobin levels following the first dose, which improved thereafter with no need for further treatment. No signs of hemolysis were observed, including normal haptoglobin levels.

III. Discussion

The patients in this study suffer from a novel disorder of PLE associated with PIL and hypercoagulability known as CD55-null PLE (CHAPLE) syndrome, which is caused by bi-allelic CD55 loss-of-function. Since disease onset, all known therapeutic trials failed, including somatostatins and corticosteroids, and patients had to adhere to a low-fat diet and MCT-rich supplements that bypass absorption through the intestinal lymphatics with limited effect. Multiple hospitalizations due to disease exacerbations and complications have been recorded, causing both physical and emotional burden to the patients and their families. The emotional stress was further exacerbated by mortality from disease complications in the extended family.

CD55 encodes a glycophosphatidylinositol (GPI)-linked membrane protein, widely expressed in many tissues, including blood, endothelial cells and the gastrointestinal tract (Lin, F. et al., *Immunology*, 104:215-25, 2001). CD55 harbors the Cromer blood group antigens and regulates complement activation by preventing formation of new C3/C5 convertases and accelerating decay of existing ones, thus inhibiting C3 and C5 cleavage and activation and protecting cells against complement-induced self-injury. Additional non-complement-dependent functions of CG55 include T-cell immunity regulation and a role in leukocyte cell adhesion through binding to CD97 (Karpus, O. et al., *J. Immunol.*, 190:3740-8, 2013; Fang, C. et al., *Blood*, 118: 1008-14, 2011).

Congenital CD55 deficiency is very rare. Only nine individuals with Cromer Inab (CD55-null) phenotype have been described to date (Yazer, M. et al., *Transfusion*, 46:1537-42, 2006). Interestingly, four of these individuals exhibited gastrointestinal phenotypes, including PLE, Crohn's disease and capillary angioma of the small intestine. Phenotypic heterogeneity is apparent both among the current family members and published CD55-null individuals, including asymptomatic or minimal symptoms among homozygotes, suggesting the effect of unknown modifiers.

The poor clinical history of the studied patients, combined with observed loss of CD55 and evident elevated levels of iC3b (product of C3b cleavage) and MAC, emphasized the need for a tailored intervention. Considering the complement-mediated pathogenicity pathway, treatment with eculizumab was initiated, similar to syndromes such as atypical hemolytic uremic syndrome (aHUS), paroxysmal nocturnal hemoglobinuria (PNH) and recurrent demyelinating neuropathy due to malfunctioning CD59 (Mevorach, D., *Mol. Immunol.*, 67:51-5, 2015; Nevo, Y. et al., *Blood*, 121:129-35, 2013; Nester, C & Thomas, C., *Hematology*, 2012:617-25, 2012).

Figure 18B:
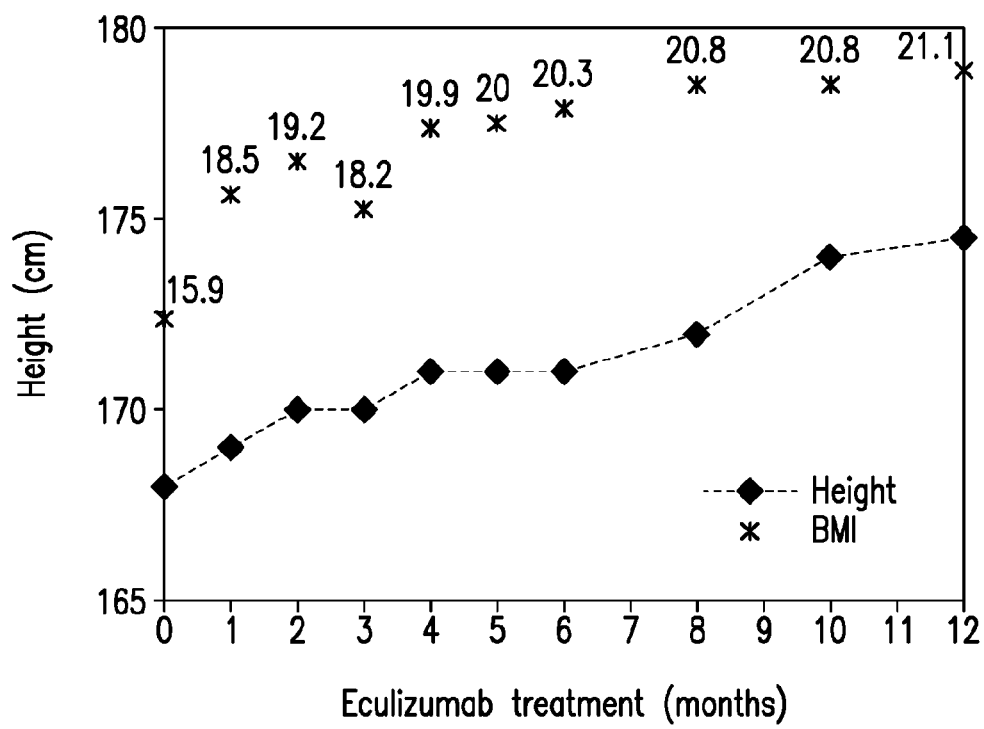
FIG. 18B depicts the height and body mass index (BMI) improvements for Patient 3 after treatment with eculizumab.

Treating CHAPLE syndrome patients with eculizumab led to dramatic clinical and laboratory responses, essentially restoring the quality of life of the patients and their parents. Within a month of treatment, signs of acute enteric protein loss were ameliorated, as marked by resolution of constant diarrhea in Patients 3 and 6, and elevation in total protein and albumin levels in all three patients. Moreover, the patients were able to abandon the low-fat diet without recurrence of PLE symptoms. This shows great promise for similar patients in their ability to maintain a normal life. The outcomes of the nutritional improvement included resolution of edema and severe dermatologic conditions, as well as new hair growth observed in all three patients. An unexpected treatment outcome for Patient 3 was his 6.5 cm growth in height at age 20 years, within 12 months of treatment (FIG. 18B). This is consistent with the known continued growth into adulthood of young patients with severe chronic early-onset disorders, such as Gaucher disease.

Previous studies in CD55-null mice with dextran sulfate sodium (DSS)-induced colitis demonstrated a more severe phenotype compared to wild type controls, whereas CD55 upregulation was observed in patients with gastrointestinal inflammation or metaplasia (Lin, F. et al., *J. Immunol.*, 172:3836-41, 2004; Berstad, A. & Brandtzaeg, P., *Gut*, 42:522-9, 1998; Mikesch, J. et al., *Biochim. Biophys. Acta*, 1766:42-52, 2006). These findings are in-line with the suggested immune-regulatory and tissue-protection roles of CD55. Yet, the exact mechanism causing protein loss and fat malabsorption is currently unclear. The role of C3 in lipid metabolism may be of interest in this respect, as one of its cleavage products is C3a-desArg (deactivated C3a), a lipogenic hormone involved in free fatty-acids transport, and triglyceride synthesis and clearance (Barbu, A. et al., *Mol. Immunol.*, 67:101-7, 2015; Murray, I. et al., *Endocrinology*, 141:1041-9, 2000). Lack of CD55 could lead to C3a-desArg over-production, raising triglycerides turnover and over-assembly of chylomicrons, thus posing heavier loads on the intestinal lymphatics. The substantial response to eculizumab indicates that MAC is possibly involved in the pathogenesis of PLE in the reported family, leading to intestinal tissue damage.

The recurring thrombotic events observed in three of the patients may be attributed to enteric loss of anticoagulation factors, and hypoalbuminemia causing secondary hepatic synthesis of procoagulants. However, CD55-null PLE patients may suffer from pro-thrombotic complement dysregulation leading to microvascular damage and hypercoagulable state, similar to other disorders of complement dysregulation (Meri, S., *Eur. J. Intern. Med.*, 24:496-502, 2013).

In conclusion, the CD55-null genotype segregating with PLE and hypercoagulability in this extended family indicates complement dysregulation is essential in the pathogenesis of CD55-related PLE. The beneficial effect of eculizumab, an inhibitor of the terminal complement pathway, provides support to the link between certain forms of PLE and complement activation.

| SEQUENCE SUMMARY |
| --- |
| SEQ ID NO: 1<br>GYIFSNYWIQ |
| SEQ ID NO: 2<br>EILPGSGSTEYTENFKD |
| SEQ ID NO: 3<br>YFFGSSPNWYFDV |
| SEQ ID NO: 4<br>GASENIYGALN |
| SEQ ID NO: 5<br>GATNLAD |
| SEQ ID NO: 6<br>QNVLNTPLT |
| SEQ ID NO: 7<br>QVQLVQSGAEVKKPGASVKVSCKASGYIFSNYWIQWVRQAPGQGLEWM<br>GEILPGSGSTEYTENFKDRVTMTRDTSTSTVYMELSSLRSEDTAVYYCA<br>RYFFGSSPNWYFDVWGQGTLVTVSS |
| SEQ ID NO: 8<br>DIQMTQSPSSLSASVGDRVTITCGASENIYGALNWYQQKPGKAPKLLIY<br>GATNLADGVPSRFSGSGSGTDFTLTISSLQPEDFATYYCQNVLNTPLTF<br>GQGTKVEIK |
| SEQ ID NO: 9<br>ASTKGPSVFPLAPCSRSTSESTAALGCLVKDYFPEPVTVSWNSGALTSG<br>VHTFPAVLQSSGLYSLSSVVTVPSSNFGTQTYTCNVDHKPSNTKVDKTV<br>ERKCCVECPPCPAPPVAGPSVFLEPPKPKDTLMISRTPEVTCVVVDVSQ<br>EDPEVQFNWYVDGVEVHNAKTKPREEQFNSTYRVVSVLTVLHQDWLNGK<br>EYKCKVSNKGLPSSIEKTISKAKGQPREPQVYTLPPSQEEMTKNQVSLT<br>CLVKGFYPSDIAVEWESNGQPENNYKTTPPVLDSDGSFELYSRLTVDKS<br>RWQEGNVESCSVMHEALHNHYTQKSLSLSLGK |
| SEQ ID NO: 10<br>QVQLVQSGAEVKKPGASVKVSCKASGYIFSNYWIQWVRQAPGQGLEWM<br>GEILPGSGSTEYTENFKDRVTMTRDTSTSTVYMELSSLRSEDTAVYYCA<br>RYFFGSSPNWYFDVWGQGTLVTVSS*ASTKGPSVFPLAPCSRSTSESTAA<br>LGCLVKDYFPEPVTVSWNSGALTSGVHTFPAVLQSSGLYSLSSVVTVPS<br>SNEGTQTYTCNVDHKPSNTKVDKTVERKCCVECPPCPAPPVAGPSVFLF<br>PPKPKDTLMISRTPEVTCVVVDVSQEDPEVQFNWYVDGVEVHNAKTKPR<br>EEQFNSTYRVVSVLTVLHQDWLNGKEYKCKVSNKGLPSSIEKTISKAKG<br>QPREPQVYTLPPSQEEMTKNQVSLTCLVKGFYPSDIAVEWESNGQPENN<br>YKTTPPVLDSDGSFFLYSRLTVDKSRWQEGNVFSCSVMHEALHNHYTQK<br>SLSLSLGK* |
| SEQ ID NO: 11<br>DIQMTQSPSSLSASVGDRVTITCGASENIYGALNWYQQKPGKAPKLLIY<br>GATNLADGVPSRFSGSGSGTDFTLTISSLQPEDFATYYCQNVLNTPLTF<br>GQGTKVEIK*RTVAAPSVFIFPPSDEQLKSGTASVVCLLNNFYPREAKVQ<br>WKVDNALQSGNSQESVTEQDSKDSTYSLSSTLTLSKADYEKHKVYACEV<br>THQGLSSPVTKSFNRGEC* |
| SEQ ID NO: 12<br>SYAIS |
| SEQ ID NO: 13<br>GIGPFFGTANYAQKFQG |
| SEQ ID NO: 14<br>DTPYFDY |
| SEQ ID NO: 15<br>SGDSIPNYYVY |
| SEQ ID NO: 16<br>DDSNRPS |
| SEQ ID NO: 17<br>QSFDSSLNAEV |
| SEQ ID NO: 18<br>QVQLVQSGAEVKKPGSSVKVSCKASGGTFSSYAISVWRQAPGQGLEWMG<br>GIGPFFGTANYAQKFQGRVTITADESTSTAYMELSSLRSEDTAVYYCAR<br>DTPYFDYWGQGTLVTVSS |
| SEQ ID NO: 19<br>DIELTQPPSVSVAPGQTARISCSGDSIPNYYVYWYQQKPGQAPVLVIYD<br>DSNRPSGIPERFSGSNSGNTATLTISGTQAEDEADYYCQSFDSSLNAEV<br>FGGGTKLTVL |
| SEQ ID NO: 20<br>NYIS |
| SEQ ID NO: 21<br>IIDPDDSYTEYSPSFQG |
| SEQ ID NO: 22<br>YEYGGFDI |
| SEQ ID NO: 23<br>SGDNIGNSYVH |
| SEQ ID NO: 24<br>KDNDRPS |
| SEQ ID NO: 25<br>GTYDIESYV |
| SEQ ID NO: 26<br>EVQLVQSGAEVKKPGESLKISCKGSGYSFTNYISWVRQMPGKGLEWMGI<br>IDPDDSYTEYSPSFQGQVTI SADKSISTAYLQWSSLKASDTAMYYCAR<br>YEYGGFDIWGQGTLVTVSS |
| SEQ ID NO: 27<br>SYELTQPPSVSVAPGQTARISCSGDNIGNSYVHWYQQKPGQAPVLVIYK<br>DNDRPSGIPERFSGSNSGNT ATLTISGTQAEDEADYYCGTYDIESYVF<br>GGGTKLTVL |
| SEQ ID NO: 28<br>SSYYVA |
| SEQ ID NO: 29<br>AIYTGSGATYKASWAKG |
| SEQ ID NO: 30<br>DGGYDYPTHAMHY |
| SEQ ID NO: 31<br>QASQNIGSSLA |
| SEQ ID NO: 32<br>GASKTHS |
| SEQ ID NO: 33<br>QSTKVGSSYGNH |

SEQUENCE SUMMARY

SEQ ID NO: 34
QVQLVESGGGLVQPGGSLRLSCAASGFTSHSSYYVAWVRQAPGKGLEWV
GAIYTGSGATYKASWAKGRFTISKDTSKNQVVLTMTNMDPVDTATYYCA
SDGGYDYPTHAMHYWGQGTLVTVSS

SEQUENCE SUMMARY

SEQ ID NO: 35
DVVMTQSPSSLSASVGDRVTITCQASQNIGSSLAWYQQKPGQAPRLLIY
GASKTHSGVPSRFSGSGSGTDFTLTISSLQPEDVATYYCQSTKVGSSYG
NHFGGGTKVEIK

The invention claimed is:

1. A method of treating a human patient with a protein-losing enteropathy, the method comprising administering to the patient during an administration cycle an effective amount of an anti-C5 antibody, or antigen binding fragment thereof, comprising CDR1, CDR2 and CDR3 heavy chain sequences as set forth in SEQ ID NOs:1, 2 and 3, respectively, and CDR1, CDR2 and CDR3 light chain sequences as set forth in SEQ ID NOs:4, 5 and 6, respectively, wherein the anti-C5 antibody, or antigen binding fragment thereof, is administered at a dose of:
   i. 600 mg to a patient weighing 10 kg to <20 kg twice per week during weeks 1 and 2 of the administration cycle and once during week 3, followed by 300 mg or 600 mg once per week during weeks 4 and 5 and every two weeks thereafter;
   ii. 600 mg to a patient weighing 20 kg to <30 kg twice per week during weeks 1 and 2 of the administration cycle, followed by 600 mg once per week during weeks 3, 4 and 5 and every two weeks thereafter;
   iii. 900 mg to a patient weighing 30 kg to <40 kg twice per week during weeks 1 and 2 of the administration cycle, followed by 900 mg once per week during weeks 3, 4 and 5 and every two weeks thereafter; or
   iv. 1200 mg to a patient weighing ≥40 kg twice per week during weeks 1 and 2 of the administration cycle, followed by 1200 mg once per week during weeks 3, 4 and 5 and every two weeks thereafter.

2. A method of treating a human patient with lymphangiectasia, the method comprising administering to the patient during an administration cycle an effective amount of an anti-C5 antibody, or antigen binding fragment thereof, comprising CDR1, CDR2 and CDR3 heavy chain sequences as set forth in SEQ ID NOs:1, 2 and 3, respectively, and CDR1, CDR2 and CDR3 light chain sequences as set forth in SEQ ID NOs:4, 5 and 6, respectively, wherein the anti-C5 antibody, or antigen binding fragment thereof, is administered at a dose of:
   i. 600 mg to a patient weighing 10 kg to <20 kg twice per week during weeks 1 and 2 of the administration cycle and once during week 3, followed by 300 mg or 600 mg once per week during weeks 4 and 5 and every two weeks thereafter;
   ii. 600 mg to a patient weighing 20 kg to <30 kg twice per week during weeks 1 and 2 of the administration cycle, followed by 600 mg once per week during weeks 3, 4 and 5 and every two weeks thereafter;
   iii. 900 mg to a patient weighing 30 kg to <40 kg twice per week during weeks 1 and 2 of the administration cycle, followed by 900 mg once per week during weeks 3, 4 and 5 and every two weeks thereafter; or iv. 1200 mg to a patient weighing ≥40 kg twice per week during weeks 1 and 2 of the administration cycle, followed by 1200 mg once per week during weeks 3, 4 and 5 and every two weeks thereafter.

3. The method of claim 1, wherein the anti-C5 antibody, or antigen binding fragment thereof, is administered to a patient weighing 10 kg to <20 kg at a dose of 600 mg twice per week during weeks 1 and 2 of the administration cycle and once during week 3, followed by 300 mg or 600 mg once per week during weeks 4 and 5 and every two weeks thereafter.

4. The method of claim 1, wherein the anti-C5 antibody, or antigen binding fragment thereof, is administered to a patient weighing 20 kg to <30 kg at a dose of 600 mg twice per week during weeks 1 and 2 of the administration cycle, followed by 600 mg once per week during weeks 3, 4 and 5 and every two weeks thereafter.

5. The method of claim 1, wherein the anti-C5 antibody, or antigen binding fragment thereof, is administered to a patient weighing 30 kg to <40 kg at a dose of 900 mg twice per week during weeks 1 and 2 of the administration cycle, followed by 900 mg once per week during weeks 3, 4 and 5 and every two weeks thereafter.

6. The method of claim 1, wherein the anti-C5 antibody, or antigen binding fragment thereof, is administered to a patient weighing ≥40 kg at a dose of 1200 mg twice per week during weeks 1 and 2 of the administration cycle, followed by 1200 mg once per week during weeks 3, 4 and 5 and every two weeks thereafter.

7. The method of claim 1, wherein the anti-C5 antibody, or antigen binding fragment thereof, comprises heavy and/or light chain variable region sequences as set forth in SEQ ID NOs:7 and 8.

8. The method of claim 1, wherein the anti-C5 antibody comprises heavy and/or light chain sequences as set forth in SEQ ID NOs:10 and 11.

9. The method of claim 1, wherein the treatment maintains a serum trough concentration of the anti-C5 antibody, or antigen binding fragment thereof, of 100 µg/mL or greater during the administration cycle.

10. The method of claim 1, wherein the treatment maintains a serum trough concentration of the anti-C5 antibody, or antigen binding fragment thereof, of 200 µg/mL or greater during the administration cycle.

11. The method of claim 1, wherein the anti-C5 antibody, or antigen binding fragment thereof, is formulated for intravenous administration.

12. The method of claim 1, wherein the treatment:
(a) produces a shift toward normal levels of serum albumin;
(b) results in at least a 1.7-fold increase in serum albumin levels from baseline within 20 days;
(c) results in at least a 5-fold increase in serum albumin levels from baseline within 80 days;
(d) produces a shift toward normal total protein serum levels;
(e) results in at least a 1.5-fold increase in total protein serum levels from baseline within 20 days;
(f) results in at least a 2.26-fold increase in total protein serum levels from baseline within 80 days;
(g) results in at least a 1.8-fold decrease in serum TNFR1 levels from baseline within 8 days; and/or
(h) results in at least a 3.25-fold decrease in serum TNFR1 levels from baseline within 43 days.

13. The method of claim 1, wherein the treatment produces at least one therapeutic effect selected from the group consisting of: a reduction or cessation in protein loss, edema, diarrhea, ascites, pleural effusion, pericarditis, lymphedema, abdominal pain, fatigue, weight loss and vitamin deficiency.

14. The method of claim 1, wherein the patient is <18 years of age.

15. The method of claim 1, wherein the administration cycle is a total of 27 weeks of treatment.

16. The method of claim 1, wherein the anti-C5 antibody, or antigen binding fragment thereof, is administered at a dose of 300 mg, 600 mg, 900 mg or 1200 mg or every two weeks after the administration cycle for up to two years.

17. The method of claim 1, wherein the method thereby treats protein-losing enteropathy.

* * * * *

UNITED STATES PATENT AND TRADEMARK OFFICE
CERTIFICATE OF CORRECTION

PATENT NO. : 11,459,382 B2  
APPLICATION NO. : 16/614582  
DATED : October 4, 2022  
INVENTOR(S) : Orly Eshach Adiv et al.

Page 1 of 1

It is certified that error appears in the above-identified patent and that said Letters Patent is hereby corrected as shown below:

On the Title Page

In item (56), 2nd Column, under "Other Publications", Line 14, delete "Nutrirtion" and insert -- Nutrition --.

In the Drawings

On figure sheet 2 of 35, in Figure 1B, Line 2, delete "Createnine" and insert -- Creatinine --.

On figure sheet 6 of 35, in Figure 2B, Line 2, delete "Createnine" and insert -- Creatinine --.

On figure sheet 16 of 35, in Figure 7D, delete "From Fig.7A" and insert -- From Fig.7C --.

In the Specification

In Column 9, Line 54, delete "enteroepathica-" and insert -- enteropathica- --.

In Column 18, Line 63, delete "on" and insert -- one --.

In Column 19, Line 16, delete "on" and insert -- one --.

In Column 19, Line 41, delete "on" and insert -- one --.

In Column 36, Line 59, delete "enteroepathica-" and insert -- enteropathica- --.

In Column 37, Line 9, delete "(IIlumina," and insert -- (Illumina, --.

In Column 37, Line 25, delete "(52):" and insert -- (S2): --.

In Column 43, Line 23, delete "granuloctyes" and insert -- granulocytes --.

Signed and Sealed this  
Twenty-second Day of November, 2022

Katherine Kelly Vidal  
*Director of the United States Patent and Trademark Office*

SEQUENCE LISTING

<160> NUMBER OF SEQ ID NOS: 37

<210> SEQ ID NO 1
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Gly Tyr Ile Phe Ser Asn Tyr Trp Ile Gln
1               5                   10

<210> SEQ ID NO 2
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Glu Ile Leu Pro Gly Ser Gly Ser Thr Glu Tyr Thr Glu Asn Phe Lys
1               5                   10                  15

Asp

<210> SEQ ID NO 3
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Tyr Phe Phe Gly Ser Ser Pro Asn Trp Tyr Phe Asp Val
1               5                   10

<210> SEQ ID NO 4
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gly Ala Ser Glu Asn Ile Tyr Gly Ala Leu Asn
1               5                   10

<210> SEQ ID NO 5

```
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Gly Ala Thr Asn Leu Ala Asp
1               5

<210> SEQ ID NO 6
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gln Asn Val Leu Asn Thr Pro Leu Thr
1               5

<210> SEQ ID NO 7
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly Ser Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser
        115                 120

<210> SEQ ID NO 8
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Asp Ile Gln Met Thr Gln Ser Pro Ser Ser Leu Ser Ala Ser Val Gly
1               5                   10                  15
```

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys
            100                 105

<210> SEQ ID NO 9
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
            275                 280                 285

Leu Thr Val Asp Lys Ser Arg Trp Gln Glu Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Leu Gly Lys
                325

<210> SEQ ID NO 10
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly Ser Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

```
Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 11
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 12
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Ser Tyr Ala Ile Ser
1               5

<210> SEQ ID NO 13
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Gly Ile Gly Pro Phe Phe Gly Thr Ala Asn Tyr Ala Gln Lys Phe Gln
1               5                   10                  15

Gly

<210> SEQ ID NO 14
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Asp Thr Pro Tyr Phe Asp Tyr
1               5

<210> SEQ ID NO 15
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Ser Gly Asp Ser Ile Pro Asn Tyr Tyr Val Tyr
1               5                   10

<210> SEQ ID NO 16
<211> LENGTH: 7
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 16

Asp Asp Ser Asn Arg Pro Ser
1               5

<210> SEQ ID NO 17
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Gln Ser Phe Asp Ser Ser Leu Asn Ala Glu Val
1               5                   10

<210> SEQ ID NO 18
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Val Trp Arg Gln Ala Pro Gly Gln Gly Leu Glu Trp Met
        35                  40                  45

Gly Gly Ile Gly Pro Phe Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Thr Pro Tyr Phe Asp Tyr Trp Gly Gln Gly Thr Leu Val
            100                 105                 110

Thr Val Ser Ser
        115

<210> SEQ ID NO 19
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Pro Asn Tyr Tyr Val
            20                  25                  30

Tyr Trp Tyr Gln Gln Lys Pro Gly Gln Ala Pro Val Leu Val Ile Tyr
        35                  40                  45
```

Asp Asp Ser Asn Arg Pro Ser Gly Ile Pro Glu Arg Phe Ser Gly Ser
            50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Ser Phe Asp Ser Ser Leu Asn Ala
                85                  90                  95

Glu Val Phe Gly Gly Gly Thr Lys Leu Thr Val Leu
            100                 105

<210> SEQ ID NO 20
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Asn Tyr Ile Ser
 1

<210> SEQ ID NO 21
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Ile Ile Asp Pro Asp Asp Ser Tyr Thr Glu Tyr Ser Pro Ser Phe Gln
 1               5                  10                  15

Gly

<210> SEQ ID NO 22
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Tyr Glu Tyr Gly Gly Phe Asp Ile
 1               5

<210> SEQ ID NO 23
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Ser Gly Asp Asn Ile Gly Asn Ser Tyr Val His
 1               5                  10

<210> SEQ ID NO 24
<211> LENGTH: 7
<212> TYPE: PRT

<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Lys Asp Asn Asp Arg Pro Ser
1               5

<210> SEQ ID NO 25
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Gly Thr Tyr Asp Ile Glu Ser Tyr Val
1               5

<210> SEQ ID NO 26
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Ile Ser Trp Val Arg Gln Met Pro Gly Lys Gly Leu Glu Trp Met Gly
        35                  40                  45

Ile Ile Asp Pro Asp Asp Ser Tyr Thr Glu Tyr Ser Pro Ser Phe Gln
    50                  55                  60

Gly Gln Val Thr Ile Ser Ala Asp Lys Ser Ile Ser Thr Ala Tyr Leu
65                  70                  75                  80

Gln Trp Ser Ser Leu Lys Ala Ser Asp Thr Ala Met Tyr Tyr Cys Ala
                85                  90                  95

Arg Tyr Glu Tyr Gly Gly Phe Asp Ile Trp Gly Gln Gly Thr Leu Val
            100                 105                 110

Thr Val Ser Ser
        115

<210> SEQ ID NO 27
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Ser Tyr Glu Leu Thr Gln Pro Pro Ser Val Ser Val Ala Pro Gly Gln
1               5                   10                  15

Thr Ala Arg Ile Ser Cys Ser Gly Asp Asn Ile Gly Asn Ser Tyr Val
            20                  25                  30

```
His Trp Tyr Gln Gln Lys Pro Gly Gln Ala Pro Val Leu Val Ile Tyr
            35                  40                  45

Lys Asp Asn Asp Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gly Thr Tyr Asp Ile Glu Ser Tyr Val
                 85                  90                  95

Phe Gly Gly Gly Thr Lys Leu Thr Val Leu
            100                 105
```

```
<210> SEQ ID NO 28
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Ser Ser Tyr Tyr Val Ala
1               5

<210> SEQ ID NO 29
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Ala Ile Tyr Thr Gly Ser Gly Ala Thr Tyr Lys Ala Ser Trp Ala Lys
1               5                   10                  15

Gly

<210> SEQ ID NO 30
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Asp Gly Gly Tyr Asp Tyr Pro Thr His Ala Met His Tyr
1               5                   10

<210> SEQ ID NO 31
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Gln Ala Ser Gln Asn Ile Gly Ser Ser Leu Ala
1               5                   10
```

-continued

```
<210> SEQ ID NO 32
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Gly Ala Ser Lys Thr His Ser
1               5

<210> SEQ ID NO 33
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Gln Ser Thr Lys Val Gly Ser Ser Tyr Gly Asn His
1               5                   10

<210> SEQ ID NO 34
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ser His Ser Ser
            20                  25                  30

Tyr Tyr Val Ala Trp Val Arg Gln Ala Pro Gly Lys Gly Leu Glu Trp
        35                  40                  45

Val Gly Ala Ile Tyr Thr Gly Ser Gly Ala Thr Tyr Lys Ala Ser Trp
    50                  55                  60

Ala Lys Gly Arg Phe Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Ser Asp Gly Gly Tyr Asp Tyr Pro Thr His Ala Met His Tyr
            100                 105                 110

Trp Gly Gln Gly Thr Leu Val Thr Val Ser Ser
        115                 120

<210> SEQ ID NO 35
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Asp Val Val Met Thr Gln Ser Pro Ser Ser Leu Ser Ala Ser Val Gly
1               5                   10                  15
```

```
Asp Arg Val Thr Ile Thr Cys Gln Ala Ser Gln Asn Ile Gly Ser Ser
            20                  25                  30

Leu Ala Trp Tyr Gln Gln Lys Pro Gly Gln Ala Pro Arg Leu Leu Ile
        35                  40                  45

Tyr Gly Ala Ser Lys Thr His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Ser Thr Lys Val Gly Ser Ser
                85                  90                  95

Tyr Gly Asn His Phe Gly Gly Gly Thr Lys Val Glu Ile Lys
            100                 105                 110

<210> SEQ ID NO 36
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 36
acgaggcttc tgcttactgc                                          20

<210> SEQ ID NO 37
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 37
cagagaccga cttggacctc                                          20
```